US008283351B2

(12) United States Patent
Russell et al.

(10) Patent No.: US 8,283,351 B2
(45) Date of Patent: Oct. 9, 2012

(54) CYCLIC AND ACYCLIC HYDRAZINE DERIVATIVES COMPOSITIONS INCLUDING THEM AND USES THEREOF

(75) Inventors: Michael Geoffrey Neil Russell, Saffron Walden (GB); Huw David Vater, Saffron Walden (GB); Jacqueline Anne Macritchie, Saffron Walden (GB); Kevin James Doyle, Saffron Walden (GB); David Brown, San Francisco, CA (US); Joanne Peach, Saffron Walden (GB)

(73) Assignee: Institute for OneWorld Health, South San Francisco, CA (US)

( * ) Notice: Subject to any disclaimer, the term of this patent is extended or adjusted under 35 U.S.C. 154(b) by 990 days.

(21) Appl. No.: 12/058,371

(22) Filed: Mar. 28, 2008

(65) Prior Publication Data

US 2008/0269206 A1   Oct. 30, 2008

Related U.S. Application Data

(60) Provisional application No. 60/909,643, filed on Apr. 2, 2007.

(51) Int. Cl.
A01N 43/56 (2006.01)
A61K 31/415 (2006.01)
C07D 401/00 (2006.01)

(52) U.S. Cl. .................. 514/252.01; 514/247; 514/403; 514/406; 544/224; 544/238; 518/264.1

(58) Field of Classification Search .............. 544/224, 544/238; 548/264.1; 514/247, 252.01, 403, 514/406
See application file for complete search history.

(56) References Cited

U.S. PATENT DOCUMENTS

| 4,052,395 | A | * | 10/1977 | Jojima et al. ............. 514/247 |
| 4,279,908 | A | * | 7/1981 | Jojima et al. ............. 514/236.5 |
| 4,397,854 | A | * | 8/1983 | Sircar ..................... 514/247 |
| 4,436,736 | A | | 3/1984 | Hodakowski et al. |
| 4,448,783 | A | | 5/1984 | Siegel |
| 4,721,711 | A | | 1/1988 | Chambon et al. |
| 5,100,647 | A | | 3/1992 | Agus et al. |
| 5,234,922 | A | | 8/1993 | Welsh et al. |
| 5,639,661 | A | | 6/1997 | Welsh et al. |
| 5,670,526 | A | | 9/1997 | Dodd et al. |
| 6,096,770 | A | | 8/2000 | Lennox et al. |
| 6,172,108 | B1 | | 1/2001 | Vega et al. |
| 6,281,240 | B1 | | 8/2001 | Schultz |
| 6,331,555 | B1 | | 12/2001 | Hirth et al. |
| 6,545,002 | B1 | | 4/2003 | Linden et al. |
| 6,630,482 | B1 | | 10/2003 | Becq et al. |
| 6,852,504 | B2 | | 2/2005 | Klaubert et al. |
| 6,960,605 | B2 | | 11/2005 | Wagle et al. |
| 6,992,096 | B2 | | 1/2006 | Karp et al. |
| 7,160,729 | B2 | | 1/2007 | Schillers et al. |
| 7,235,573 | B2 | | 6/2007 | Verkman et al. |
| 7,304,090 | B2 | | 12/2007 | Sheppard et al. |
| 7,414,037 | B2 | | 8/2008 | Verkman et al. |
| 2003/0008288 | A1 | | 1/2003 | Germino et al. |
| 2004/0034075 | A1 | | 2/2004 | Smith et al. |
| 2004/0063695 | A1 | | 4/2004 | Verkman et al. |
| 2004/0235800 | A1 | | 11/2004 | Verkman et al. |
| 2005/0113423 | A1 | | 5/2005 | VanGoor et al. |
| 2005/0130970 | A1 | | 6/2005 | Miller et al. |
| 2005/0239740 | A1 | | 10/2005 | Verkman et al. |
| 2006/0079515 | A1 | | 4/2006 | Frost |

(Continued)

FOREIGN PATENT DOCUMENTS

AU   3277162   4/2004

(Continued)

OTHER PUBLICATIONS

Wikipedia, Isomers, http://en.wikipedia.org/wiki/Isomer, downloaded Nov. 26, 2010.*
Xu, et al., J. Polym. Sci., Part A: Polym. Chem. (2006), vol. Date 2007, 45(2), 262-268.*
Lee, et al., J. Kor. Chem. Soc. 2006, vol. 50, No. 5, 420-423.*
Haider, et al., Sci. Synth. (2004), 16, 125-249.*
Feng, et al., Synth. Commun. (2003), 33(7), 1155-1161.*
Baraldi, et al., Synthesis (1994), (11), 1158-62.*
Xu, et al., J. Chin. Pharm. Sci. (1992), 1(2), 27-34.*
Coates, et al., Synthesis (1993), (3), 334-42.*

(Continued)

Primary Examiner — Paul V. Ward
(74) Attorney, Agent, or Firm — Foley & Lardner LLP; Antoinette F. Konski; Photon Rao

(57) ABSTRACT

The present invention relates to compositions and methods for treating a disease in an animal, which disease is responsive to inhibiting of the functional cystic fibrosis transmembrane conductance regulator (CFTR) polypeptide by administering to a mammal in need thereof an effective amount of a cyclic or acyclic hydrazine derivative including those of formulas II or III:

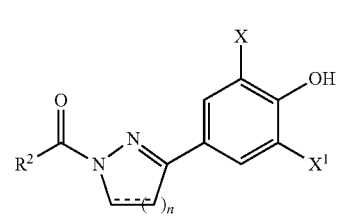

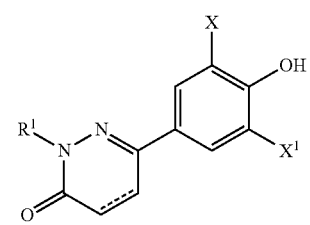

or compositions thereof, thereby treating the disease. The present invention particularly, relates to a method of treating diarrhea and polycystic kidney disease.

5 Claims, No Drawings

U.S. PATENT DOCUMENTS

| | | | |
|---|---|---|---|
| 2006/0088828 | A1 | 4/2006 | Harris et al. |
| 2007/0015780 | A1 | 1/2007 | Picker et al. |
| 2007/0161687 | A1 | 7/2007 | Karp et al. |
| 2007/0244159 | A1 | 10/2007 | Hadida Ruah et al. |
| 2007/0259854 | A1 | 11/2007 | Murakami et al. |
| 2007/0265316 | A1 | 11/2007 | Verkman |
| 2008/0025921 | A1 | 1/2008 | Caplan et al. |
| 2008/0051410 | A1 | 2/2008 | Watterson et al. |
| 2008/0064666 | A1 | 3/2008 | Verkman |
| 2008/0071095 | A1 | 3/2008 | Hadida-Ruah et al. |
| 2008/0171793 | A1 | 7/2008 | Verkman et al. |
| 2008/0269206 | A1 | 10/2008 | Russell et al. |
| 2008/0293717 | A1 | 11/2008 | Ugashe et al. |
| 2008/0319008 | A1 | 12/2008 | Verkman et al. |
| 2009/0048207 | A1 | 2/2009 | Verkman et al. |
| 2009/0253799 | A1 | 10/2009 | Verkman et al. |
| 2009/0263853 | A1 | 10/2009 | Gardener et al. |
| 2009/0264433 | A1 | 10/2009 | Russell et al. |
| 2009/0264441 | A1 | 10/2009 | Jones |
| 2009/0264471 | A1 | 10/2009 | Russell et al. |
| 2009/0264481 | A1 | 10/2009 | Jones et al. |
| 2009/0264486 | A1 | 10/2009 | Jones et al. |
| 2009/0270398 | A1 | 10/2009 | Russell et al. |
| 2009/0318429 | A1 | 12/2009 | Doyle et al. |
| 2010/0144733 | A1 | 6/2010 | Doyle et al. |

FOREIGN PATENT DOCUMENTS

| | | |
|---|---|---|
| CA | 2500498 | 4/2004 |
| DE | 19831803 | 4/1999 |
| EP | 0764685 | 3/1997 |
| EP | 0 952 159 A2 | 10/1999 |
| GB | 1334400 | 10/1973 |
| GB | 1446980 | 8/1976 |
| GB | 2107074 | 4/1983 |
| JP | 53012879 * | 2/1978 |
| JP | 59162541 | 9/1984 |
| WO | WO 99/65867 | 12/1999 |
| WO | WO 01/30333 | 5/2001 |
| WO | WO 02/32864 | 4/2002 |
| WO | WO 03/078386 | 9/2003 |
| WO | WO-03/105840 | 12/2003 |
| WO | WO-2004/028480 | 4/2004 |
| WO | WO-2004/028535 | 4/2004 |
| WO | WO 2004/103371 | 12/2004 |
| WO | WO-2004/110352 | 12/2004 |
| WO | WO-2005/007123 | 1/2005 |
| WO | WO 2005/037779 | 4/2005 |
| WO | WO 2005/094374 | 10/2005 |
| WO | WO-2005/120497 | 12/2005 |
| WO | WO 2007130383 * | 4/2006 |
| WO | WO-2006/101740 | 9/2006 |
| WO | WO-2006/102483 | 9/2006 |

OTHER PUBLICATIONS

Xu, et al., Yaoxue Xuebao (1991), 26(9), 656-60.*
Coates, et al., Heterocycles (1989), 29(6), 1077-90.*
Singh, Heterocycles (1984), 22(8), 1801-4.*
Abdel-Rahman, et al., Heteroatom Chem., vol. 16, No. 1, 2005, 20-27.*
Wermuth, et al., J. Med. Chem. (1989), 32(3), 528-37.*
U.S. Appl. No. 12/426,483, filed Apr. 20, 2009, Doyle, K.
U.S. Appl. No. 12/590,977, filed Nov. 16, 2009, Doyle et al.
Akiba, et al., "A Novel Small Molecule CFTR Inhibitor Attenuates HCO3 Secretion and Duodenal Ulcer Formation in Rats", Am J. Physiol Gatrointest. Liver Physiol. (2005), 289: G753-G759.
Brown, et al., "Chemical chaperones correct the mutant phenotype of the DF508 cystic fibrosis transmembrane conductance regulator protein," Cell Stress and Chaperones, (1996) 1(2):117-125.
Carone, et al., "Biology of Disease," Lab. Inv. (1994), 70:437-448.
Davis, et al., "Proprietary Oral Glucose/Electrolyte Solution for Diarrhea," Lancet (1982) 2(8313):1456.
Fang, et al, "Contribution of CFTR to apical-basolateral fluid transport in cultured human alveolar epithelial type II cells," Amer J.of Physiol.—Lung Cellular and Molecular Physiol.,290(5):pL1044 (2006).
Fang, et al., "Contribution of CFTR to apical-basolateral fluid transport in cultured human alveolar epithelial type II cells," Amer J.of Physiol.—Lung Cellular and Molecular Physiol., 290(2):pL242-L249 (2006).
Field, et al., "Intestinal Electrolyte Transport and Diarrheal Disease," N. Eng. J. Med. (1989), 321:879-883.
Fischer, et al., "A Novel Extract SB-300 from the Stem Bark Latex of Croton Lechleri Inhibits CFTR-Mediated Chloride Secretion in Human Colonic Epithelial Cells," Journal of Ethnopharmacology 93 (2004) 351 13357.
Friedman, J., "Cystic Diseases of the Kidney, " in Principles and Practice of Medical Genetics ( A. Emery and D. Rimoin, Eds.) (1983), pp. 1002-1010, Churchill Livingston, Edinburgh, U.K.
Gabow & Grantham, "Polycystic Kidney Disease," in Diseases of the Kidney (R. Schrier & C. Gottschalk, Eds.) (1997), pp: 521-560, Little Brown, Boston.
Gabow, P. A., "Autosomal dominant polycystic kidney disease—more than a renal disease," Am. J. Kidney Dis. (1990), 16:403-413.
Galietta, et al., "Novel CFTR Chloride Channel Activators Identified by Screening of Combinatorial Libraries Based on Flavone and Benzoquinolizinium Lead Compounds," Journal of Biological Chemistry (2001) 276(23):19723-19728.
Gretz, et al., "Rat Models of Autosomal Dominant Polycystic Kidney Disease," Nephrology Dialysis Transplantation (1996), 11:46-51.
Haggie, et al., "Increased Diffusional Mobility of CFTR at the Plasma Membrane after Deletion of its C-terminal PDZ Binding Motif," J. of Biological Chemistry, (2004) 279(7):5494-5500.
Haggie, et al., "Mobility of ΔF508-CFTR in the Endoplasmic Reticulum," Biophysical Journal, (2002) 82(1 Part 2):626a.
Hasegawa, et al., "A multifunctional aqueous channel formed by CFTR," Science (Washington DC), (1992) 258:1477-1479.
Jayaraman, et al., "Noninvasive in vivo fluorescence measurement of airway-surface liquid depth, salt concentration, and pH," Journal of Clinical Investigation, (2001) 107(3):317-324.
Jayaraman, et al., "Submucosal gland secretions in airways from cystic fibrosis patients have normal (Na+) and pH but elevated viscosity," Proceedings of the National Academy of Sciences of the United States of America, (2001) 98(14):8119-8123.
Kaspareit-Rittinghausen, et al., "A New Rat Model for Polycystic Kidney Disease of Humans," Transpl. Proc. (1990), 22:2582-2583.
Kim, et al. "Pharmacophore-based Virtual Screening: the Discovery of Novel Methionyl-tRNA Synthetase Inhibitors" (2006) Bioorg. Med. Chem. Lett. 16(18): 4898-4907.
Kunzelmann, et al., "Electrolyte Transport in the Mammalian Colon: Mechanisms and Implications for Disease," Physiol Rev. (2002) 82(1):245-289.
Levin, et al., "CFTR-regulated chloride transport at the ocular surface in living mice measured by potential differences," IOVS, (2005) 46(4):1428-1434.
Levin, et al., "Potential difference measurements of ocular surface Na absorption analyzed using an electrokinetic model," IOVS, (2006) 47(1):306-316.
Lohi, et al., "Upregulation of CFTR Expression but not SLC26A3 and SLC9A3 in Ulcerative Colitis,:" Am. J. Physiol. Gastrointest. Liver Physiol. (2002), 283(3):G567-75).
Muanprasat, et al., "Identification of New Small Molecule Inhibitors of Cystic Fibrosis Transmembrane Conductance Regulator Protein: In Vitro and in Vivo Studies," Biol. Pharm. Bull. (2007) 30(3):502-507.
Nakanishi, et al., "Role of CFTR in Autosomal Recessive Polycystic Kidney Disease," J. Am. Soc. Nethprol. (2001), 12:719-725.
Neville, et al., "Evidence for phosphorylation of serine 753 in CFTR using a novel metal-ion affinity resin and matrix-assisted laser desorption mass spectrometry," Protein Science, (1997) 6(11):2436-2445.
Neville, et al., "Expression and characterization of the NBD1-R domain region of CFTR: Evidence for subunit-subunit interactions,"Biochemistry, (1998) 37(8):2401-2409.
Pedemonte, et al., "Phenylglycine and sulfonamide correctors of defective ΔF508 and G551D cystic fibrosis transmembrane conductance regulator chloride-channel gating," Molecular Pharmacology, (2005) 67(5):1797-1807.

Reenstra, et al., "Protein Kinase A Dependent Membrane Protein Phosphorylation and Chloride Conductance in Endosomal Vesicles from Kidney Cortex," Biochemistry, (1992) 31(1):175-181.

Salinas, et al., "CFTR Involvement in Nasal Potential Differences in Mice and Pigs Studied Using a Thiazolidinone CFTR Inhibitor," American J. of Physiology—Lung Cellular and Molecular Physiology, (2004) 287(5):pL936-L943.

Schafer, et al., "Characterization of the Han:SPRD Rat Model for Heriditary Polycystic Kidney Disease," Kidney Int. (1994), 46:134-152.

Sheppard, et al., "Expression of Cystic Fibrosis Transmembrane Conductance Regulator in a Model Epithelium," Am. Physiol. Society (1994), 266 (Lung Cell. Mol. Physiol. 10):L405-L413.

Sheppard, D., "CFTR Channel Pharmacology: Novel Pore Blockers Identified by High-throughput Screening," J. Gen. Physiol. (2004) 109-113.

Song, et al., Hyperacidity of secreted fluid form submucosal glands in early cystic fibrosis, American J. of Physiol.—Cell Physiol., (2006) 290(3):C741-C749.

Springsteel, et al., "Benzoflavone Activators of the Cystic Fibrosis Transmembrane Conductance Regulator: Towards a Pharmacophore Model for the Nucleotide-binding Domain," Bioorganic and Medicinal Chemistry, (2003) 11(18):4113-4120.

Striker & Striker "Renal Cysts in Polycystic Kidney Disease," Am. J. Nephrol. (1986), 6:161-164.

Suen et al., "Sulfamoyl-4-oxoquinoline-3-carboxamides: Novel potentiators of defective Delta F508-cystic fibrosis transmembrane conductance regulator chloride channel gating," Bioorganic & Medicinal Chemistry Letters, (2006) 16(3):537-540.

Taddei, et al., "Altered Channel Gating Mechanism for CFTR Inhibition by a High-affinity Thiazolidinone Blocker," FEBS Letters, (2004) 558(1-3):52-56.

Thiagarajah, et al., "Prevention of Cholera and $E$-$coli$ Toxin-induced Intestinal ion and Fluid Secretion by a Small Molecule CFTR Inhibitor," FASEB Journal, (2003) 17(4-5):Abstract No. 600.14.

Thiagarajah, et al. "CFTR Pharmacology and its Role in Intestinal Fluid Secretion," Current Opinion in Pharmacology (2003) 3:594-599.

Van Goor, et al., "Rescue of ΔF508-CFTR Trafficking and Gating in Human Cystic Fibrosis Airway Primary Cultures by Small Molecules," Am. J. Physiol. Lung Cell Mol. Physiol. (2006) 290:L1117-L1130.

Verkman, et al., "Drug Discovery in Academia," American Journal of Physiology, (2004) 286(3 Part1):C465-C474.

Verkman, et al., "Lung disease in cystic fibrosis: Is airway surface liquid composition abnormal?" American Journal of Physiology, (2001) 281(2 Part 1):L306-L308.

Verkman, et al., "Sodium and chloride transport at the mouse ocular surface measured by open-circuit potential differences, and analyzed using an electrokinetic model of ocular surface ion transport," IOVS, (2005) 46(Suppl.S):2196.

Verkman, et al., "CFTR Chloride Channel Drug Discovery—Inhibitors as Antidiarrheals and Activators for Therapy of Cystic Fibrosis," Current Pharmaceutical Design, (2006) 12:2235:2247.

Wang, et al. "Effects of a new cystic fibrosis transmembrane conductance regulator inhibitor on Cl-conductance in human sweat ducts," Exp. Physiol. (2004) 89(4):417-425.

Welling & Grantham, "Cystic and developmental diseases of the kidney. Nomenclature and Pathogenysis of Renal Cysts," 5th Ed., edited by Brenner BM, Philadelphia, Saunders, (1996) 1828-1863.

Wilson, P. "Polycystic Kidney Disease," N. Eng. J. Med. (2004), 350:151-164.

Yang, et al. "Nanomolar Affinity Small Molecule Correctors of Defective ΔF508-CFTR Chloride Channel Gating," J. Biolog. Chem. (2003) 278(37): 35079-35085.

Aminabhavi et al. "Synthesis and Characterization of Biologically Active Oraganosilicon and Organotin Complexes of Phenylglycyl Hydrazones," (1987) lnorg. Chim. Acta. 135: 139-143.

Brock et al. "Selective Open-Channel Block of Shaker (Kv1) Potassium Channels by N-nitrosodithiothreitol (SNDTT)," (2001) J. Gen. Physiol. 118: 113-133.

Cai et al. "Strategies to Investigate the Mechanism of Action of CFTR Modulators," (2004) J. Cyst. Fibrosis 3: 141-147.

Chao et al. "Activation of Intestinal CFTR Cl⁻ Channel by Heat-Stable Enterotoxin and Guanylin via cAMP-Dependent Protein Kinase," (1994) The EMBO Journal 13: 1065-1072.

Dawson et al. "CFTR: Mechanism of Anion Conduction," (1999) Physiol. Rev. 79: S47-S75.

Edwards et al. "Induction of a glibenclamide-sensitive K-current by modification of a delayed rectifier channel in rat portal vein and insulinoma cells," (1993) Br. J. Pharmacol. 110: 1280-1281.

Kim et al. "Pharmacophore-based Virtual Screening: the Discovery of Novel Methionyl-tRNA Synthetase Inhibitors" (2006) Bioorg. Med. Chem. Lett. 16(18): 4898-4907.

Ma et al. "High-Affinity Activators of Cystic Fibrosis Transmembrane Conductance Regulator (CFTR) Chloride Conductance Identified by High-Throughput Screening," (2002) J. Biolog. Chem. 277: 37235-37241.

Ma et al. "Thiazolidinone CFTR Inhibitor Identified by High-Throughput Screening Blocks Cholera Toxin-Induced Intestinal Fluid Secretion," (2002) J. Clin. Invest. 110: 1651-1658.

McCarty "Permeation Through the CFTR Chloride Channel," (2000) J. Exp. Biol. 203: 1947-1962.

Misra et al. "Possible Antituberculous Compounds. PartXV. N-2-Thiazolyl-glycines, 1-Acyl-4-aryl Semicarbazides, 1-Acyl-4-aryl Thio-semicarbazides, and N'-(N-Arylglycyl)-$N^2$-(Arylidene or Alkylidene)hydrazines" (1963) J. Indian Chem. Soc. 40(9): 799-802.

Muanprasat et al. "Discovery of Glycine Hydrazide Pore-occluding CFTR Inhibitors: Mechanism, Structure—Activity Analysis, and In Vivo Efficacy," (2004) J. Gen. Physiol. 124: 125-137.

Pedemonte et al. "Small-Molecule Correctors of Defective ΔF508-CFTR Cellular Processing Identified by High-Throughput Screening," (2005) J. Clin. Invest. 115: 2564-2571.

Ramamurthy et al. "Synthesis and Antitubercular Activity of N-(2-Naphthyl)glycine Hydrazide Analogues," (1989) J. Med. Chem. 32: 2421-2426.

Salinas et al. "Submucosal Gland Dysfunction as a Primary Defect in Cystic Fibrosis," (2005) Faseb J. 19: 431-433.

Schultz et al. "Pharmacology of CFTR Chloride Channel Activity," (1999) Physiol. Rev. 79: S109-S144.

Sheppard et al. "Mechanism of Glibenclamide Inhibition of Cystic Fibrosis Transmembrane Conductance Regulator Cl⁻ Channels Expressed in a Murine Cell Line," (1997) J. Physiol. 503: 333-346.

Sonawane et al. "In Vivo Pharmacology and Antidiarrheal Efficacy of a Thiazolidinone CFTR Inhibitor in Rodents," (2005) J. Pharm Sci. 94: 134-143.

Sonawane et al. "Luminally Active, Nonabsorbable CFTR Inhibitors as Potential Therapy to Reduce Intestinal Fluid Loss in Cholera" (2006) FASEB Journal 20(1): 130-132.

St. Aubin et al. "Identification of a Second Blocker Binding Site at the Cytoplasmic Mouth of the Cystic Fibrosis Transmembrane Conductance Regulator Chloride Channel Pore," (2007) Molecular Pharmacology Fast Forward, published Feb. 9, 2007.

Thiagarajah et al. "New Drug Targets for Cholera Therapy," (2005) Trends in Pharmacological Sciences 26: 172-175.

Verma et al. "Syntheses and Anti-inflammatory Activities of Substituted Arylamino-[N-benzylidene)acetohydrazides and Derivatives," (1984) Arch. Pharm. 317: 890-894.

Wang et al. "Predominant Constitutive CFTR Conductance in Small Airways " (2005) Respiratory Research 6: 7.

Yang et al. "Nanomolar Affinity Small Molecule Correctors of Defective ΔF508-CFTR Chloride Channel Gating," (2003) J. Biolog. Chem. 278: 35079-35085.

Zhou et al. "Probing an Open CFTR Pore with Organic Anion Blockers," (2002) J. Gen. Physiol. 120: 647-662.

Office Action for U.S. Appl. No. 12/426,481, dated May 12, 2010.
Office Action for U.S. Appl. No. 12/426,483, dated Jul. 15, 2010.
Office Action for U.S. Appl. No. 12/426,860, dated Jan. 28, 2011.
Patani et al., Chem Rev, 1996, vol. 96 (8), especially p. 3147.
Restriction Requirement for U.S. Appl. No. 12/426,459, dated Aug. 4, 2010.
Restriction Requirement for U.S. Appl. No. 12/426,860, dated Dec. 14, 2010.

\* cited by examiner

CYCLIC AND ACYCLIC HYDRAZINE DERIVATIVES COMPOSITIONS INCLUDING THEM AND USES THEREOF

CROSS-REFERENCE TO RELATED APPLICATIONS

This application claims the benefit under 35 U.S.C. §119(e) of provisional patent application Ser. No. 60/909,643, filed on Apr. 2, 2007, which is incorporated herein by reference in its entirety.

FIELD OF THE INVENTION

This application and invention disclose hydrazone-containing compounds that inhibit the transport of ions (e.g., chloride ions) across cell membranes expressing the cystic fibrosis transmembrane conductance regulator (CFTR) protein. The structures of these CFTR inhibitory compounds and derivatives thereof, as well as pharmaceutical formulations and methods of use are described in more detail below.

BACKGROUND

Diarrhea is commonly caused by infection by a variety of bacteria, parasites and viruses and is a fundamental threat to regions lacking potable water. Preventing exposure to the pathogens responsible for diarrhea is the only way to avert infection. Unfortunately, this requires massive improvement in both sanitation and nutritional status in developing countries, which is unlikely to occur in the short term. Thus, it is a continuing threat to the third world and especially the health of children who may lack a robust immune response. Second only to respiratory infection, diarrheal disease is responsible for approximately two million deaths in children under five years of age annually. Many who do survive have lasting health problems due to the effects of recurrent infections and malnutrition. Diarrheal diseases also are the major cause of childhood hospitalization, primarily for dehydration. Each year in developing countries, roughly four billion episodes of acute diarrhea, or approximately 3.2 episodes per child, occur among children under five years of age. See, in general, Diarrheal Diseases Fact Sheet, available at www.oneworldhealth.org.

Diarrheal episodes can be either acute or persistent (lasting two weeks or more). Of all childhood infectious diseases, diarrheal diseases are thought to have the greatest effect on growth, by reducing appetite, altering feeding patterns, and decreasing absorption of nutrients. The number of diarrheal episodes in the first two years of life has been shown not only to affect growth but also fitness, cognitive function, and school performance.

The primary cause of death from diarrhea is dehydration. As dehydration worsens, symptoms progress from thirst, restlessness, decreased skin turgor and sunken eyes to diminished consciousness, rapid and feeble pulse and low or undetectable blood pressure. Diarrhea also often arises as a result of coinfection with other diseases such as malaria and HIV and is frequently a comorbidity factor associated with deaths due to these diseases.

It is well established that the cystic fibrosis transmembrane conductance regulator (CFTR) protein plays a pivotal role in enterotoxin-mediated secretory diarrheal disease and dehydration which occurs as a consequence of body fluid loss following electrolyte transport across the epithelial cells lining the gastrointestinal tract. Kunzelmann and Mall, (2002) Physiological Rev. 82(1):245-289. CFTR is a 1480 amino acid protein that is a member of the ATP binding cassette (ABC) transporter family. The CFTR cAMP-activated Cl$^-$ channel is expressed primarily in the apical or luminal surface of epithelial cells in mammalian intestine, lungs, proximal tubules (and cortex and medulla) of kidney, pancreas, testes, sweat glands and cardiac tissue where it functions as the principal pathway for secretion of Cl(−)/HCO$_3$(−) and Na(+)/H(+). See Field et al. (1974) N. Engl. J. Med. 71:3299-3303 and Field et al. (1989) N. Eng. J. Med. 321:879-883.

In secretory diarrhea, intestinal colonization by pathogenic microorganisms alter ion transport, disrupt tight cell junctions and activate an inflammatory response. Enterotoxins produced by Enterotoxigenic *Escherichia coli* (ETEC) and *Vibrio cholerae* bind to receptors on the luminal surface of enterocytes and generates intracellular second messengers that lead to upregulation of CFTR and secretion of negatively charged ions (e.g. chloride) across the intestinal epithelia which creates the driving force for sodium and water secretion. Kunzelmann (2002) supra. Luminal CFTR therefore plays the central role in secretory diarrhea and the excessive loss of water which leads to severe dehydration and rapid progression to death if untreated. Blocking ion transport across luminal CFTR channels has been proposed as one way to treat secretary diarrhea and other disease etiologically related to ion transport across CFTR channels.

Mutations in CFTR protein, e.g., Δ508, are responsible for cystic fibrosis (CF), one of the most common serious inherited diseases amongst Caucasians, affecting approximately 1 in 2,500 individuals. Pedemonte et al. (2005) J. Clin. Invest. 115(9):2564-2571. In the United States and in the majority of European countries, the incidence of carriers of the CF gene is 1 in 20 to 1 in 30. CF can affect many organs including sweat glands (high sweat electrolyte with depletion in a hot environment), intestinal glands (meconium ileus), biliary tree (biliary cirrhosis), pancreas (CF patients can be pancreatic insufficient and may require enzyme supplements in the diet) and bronchial glands (chronic bronchopulmonary infection with emphysema). Hormones, such as a β-adrenergic agonist, or a toxin, such as cholera toxin, lead to an increase in cAMP, activation of cAMP-dependent protein kinase, and phosphorylation of the CFTR Cl$^-$ channel, which causes the channel to open. An increase in cell Ca$^{2+}$ can also activate different apical membrane channels. Phosphorylation by protein kinase C can either open or shut Cl$^-$ channels in the apical membrane.

The transport of fluids mediated by CFTR also has been linked to Polycystic Kidney Disease (PKD). Autosomal Dominant Polycystic Kidney Disease (ADPKD) is the most common genetic renal disorder occurring in 1:1000 individuals and is characterized by focal cyst formation in all tubular segments. Friedman, J. Cystic Diseases of the Kidney, in PRINCIPLES AND PRACTICE OF MEDICAL GENETICS (A. Emery and D. Rimoin, Eds.) pp. 1002-1010, Churchill Livingston, Edinburgh, U.K. (1983); Striker & Striker (1986) Am. J. Nephrol. 6:161-164. Extrarenal manifestations include hepatic and pancreatic cysts as well as cardiovascular complications. Gabow & Grantham (1997) Polycystic Kidney Disease, in DISEASES OF THE KIDNEY (R. Schrier & C. Gottschalk, Eds.), pp. 521-560, Little Brown, Boston; Welling & Grantham (1996) Cystic Diseases of the Kidney, in RENAL PATHOLOGY (C. Tisch & B. Brenner, Eds.) pp: 1828-1863, Lippincott, Philadelphia. Studies suggest that increased cAMP-mediated chloride secretion provides the electrochemical driving force, which mediates fluid secretion in cystic epithelia. Nakanishi et al. (2001) J. Am. Soc. Nethprol. 12:719-725. PKD is a leading cause of end-stage renal failure and a common indication for dialysis or renal transplantation. PKD may arise sporadically as a developmental abnormality or may be acquired in adult life, but most forms are hereditary. Among the acquired forms, simple cysts can develop in kidney as a consequence of aging, dialysis, drugs and hormones. Rapaport (2007) QJM 100:1-9 and Wilson (2004) N. Eng. J. Med. 350:151-164.

CFTR inhibitors have been discovered, although they have a weak potency and lack CFTR specificity. The oral hypoglycemic agent glibenclamide inhibits CFTR Cl⁻ conductance from the intracellular side by an open channel blocking mechanism (Sheppard & Robinson (1997) J. Physiol. 503: 333-346; Zhou et al. (2002) J. Gen. Physiol. 120:647-662) at high micromolar concentrations where it affects Cl⁻ and other cation channels. Rabe et al. (1995) Br. J. Pharmacol. 110: 1280-1281 and Schultz et al. (1999) Physiol. Rev. 79:S109-S144. Other non-selective anion transport inhibitors including diphenylamine-2-carboxylate (DPC), 5-nitro-2(3-phenylpropyl-amino)benzoate (NPPB), flufenamic acid and niflumic acid also inhibit CFTR by occluding the pore at an intracellular site. Dawson et al. (1999) Physiol. Rev. 79:S47-S75; McCarty (2000) J. Exp. Biol. 203:1947-1962, Cai et al. (2004) J. Cyst. Fibrosis 3:141-147. Hence, high-affinity CFTR inhibitors can have clinical applications in the therapy of secretory diarrheas, cystic kidney disease, and other associated disorder reported to be mediated by functional CFTR.

SUMMARY OF THE INVENTION

This invention is directed to one or more of compounds, compositions and methods which are useful in treating diarrhea. In one aspect of the invention, there is provided a compound of the formula I:

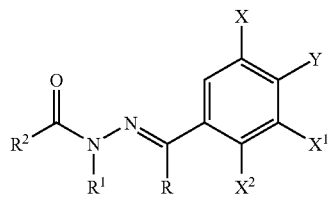

wherein:
R is selected from the group consisting of hydrogen, alkyl and substituted alkyl;
$R^1$ is selected from the group consisting of hydrogen, alkyl, substituted alkyl, aryl, substituted aryl, alkenyl, substituted alkenyl, alkynyl, substituted alkynyl, cycloalkyl, substituted cycloalkyl, heterocyclic, substituted heterocyclic, heteroaryl and substituted heteroaryl;
or R and $R^1$ together with the atoms bound thereto, form a heterocycle or substituted heterocycle;
$R^2$ is selected from the group consisting of alkyl, substituted alkyl, aryl, substituted aryl, cycloalkyl, substituted cycloalkyl, heterocyclic, substituted heterocyclic, heteroaryl and substituted heteroaryl;
or R and $R^2$ together with the atoms bound thereto, form a heterocycle or substituted heterocycle;
or $R^1$ and $R^2$ together with the atoms bound thereto, form a heterocycle or substituted heterocycle;
X and $X^1$ are independently selected from the group consisting of hydrogen, halo, hydroxyl, nitro, alkyl, substituted alkyl, aryl, substituted aryl, alkoxy, substituted alkoxy, cycloalkyl, substituted cycloalkyl, heterocyclic, substituted heterocyclic, heteroaryl, substituted heteroaryl, carboxyl, and carboxyl ester;
$X^2$ is selected from the group consisting of hydrogen, halo and hydroxyl; and
Y is selected from the group consisting of hydrogen, halo, hydroxyl, alkoxy and substituted alkoxy;
or either of X or $X^1$ and Y together with the atoms bound thereto, form an aryl, substituted aryl, heteroaryl or substituted heteroaryl; or
a pharmaceutically acceptable salt, isomer, prodrug, or tautomer thereof;
wherein said compound exhibits an $IC_{50}$ of less than 30 µM or a greater than 35% inhibition at 50 µM in a T84 assay, provided that the compound does not have an $IC_{50}$ greater than 30 µM, or a greater than 30% inhibition at 20 µM in a FRT assay;
with the provisos that:
(1) $R^2$ is not —$CR^{20}$H (substituted amino), wherein $R^{20}$ is hydrogen, methyl, substituted alkyl or substituted phenyl; and said substituted amino does not include substituted amino wherein the nitrogen is a ring atom in a heterocycle, substituted heterocycle, heteroaryl or substituted heteroaryl; and
(2) the compound is not

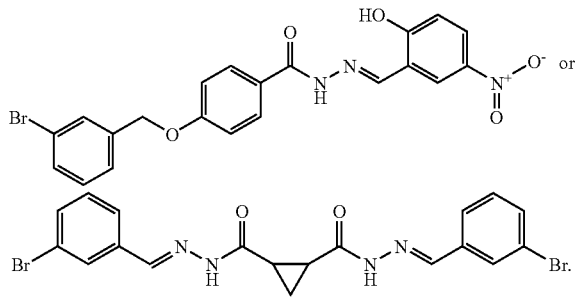

In another embodiment, the compounds of formula I exhibit at least 30% inhibition of maximally stimulated CFTR iodide influx as determined by measurement of a relative YFP fluorescence versus time when tested at 20 µM in the assay described herein.

In another embodiment, the compounds of formula I exhibit an $IC_{50}$ of less than 30 µM when tested in the T84 assay described herein. Or alternatively, the compounds of formula I exhibit at least 35% inhibition at 50 µM when tested in the T84 assay described herein, provided that the compound does not have an $IC_{50}$ greater than 30 µM.

Another aspect of this invention relates to a method for treating diarrhea in an animal in need thereof by administering to the animal an effective amount of one or more of the compounds defined herein (including those compounds set forth in Tables 1-6 or encompassed by formulas I-VI) or compositions thereof, thereby treating diarrhea.

Still another aspect of this invention relates to a method for treating polycystic kidney disease (PKD) in an animal in need thereof, by administering to the animal an effective amount of one or more of the compounds defined herein (including those compounds set forth in Tables 1-6 or encompassed by formulas I-VI) or compositions thereof, thereby treating PKD.

Another aspect of the present invention relates to a method of treating a disease in an animal, which disease is responsive to inhibiting of functional CFTR protein by administering to an animal in need thereof an effective amount of a compound defined herein (including those compounds set forth in Tables 1-6 or encompassed by formulas I-VI) or compositions thereof, thereby treating the disease.

Yet another aspect of the present invention relates to a method for inhibiting the transport of a halide ion across a mammalian cell membrane expressing functional CFTR protein comprising contacting the CFTR protein with an effective amount of compound defined herein (including those compounds set forth in Tables 1-6 or encompassed by formulas I-VI) or compositions thereof, thereby inhibiting the transport of the halide ion by the CFTR protein.

DETAILED DESCRIPTION OF THE INVENTION

The invention is based on hydrazone-containing compounds that are CFTR inhibitors. The structure of these CFTR inhibitory compounds and derivatives thereof, as well as pharmaceutical formulations and methods of use, are described in more detail below.

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

A. Definitions

The practice of the present invention will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The terms "polypeptide" and "protein" are synonymously used in their broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

A polynucleotide or polynucleotide region (or a polypeptide or polypeptide region) has a certain percentage (for example, 80%, 85%, 90%, or 95%) of "sequence identity" to another sequence when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2$C≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thio substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thio substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$— or —$CH(CH_3)CH_2$—), butylene (—$CH_2CH_2CH_2CH_2$—), isobutylene (—$CH_2CH(CH_3)CH_2$—), sec-butylene (—$CH_2CH_2CH(CH_3)$—) H—) and the like. "Straight chain $C_1$-$C_6$ alkylene" refers to unbranched alkylene groups having from 1 to 6 carbons. "Straight chain $C_2$-$C_6$ alkylene" refers to unbranched alkylene groups having from 2 to 6 carbons.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups. It is to be noted that when the alkylene is substituted by an oxo group, 2 hydrogens attached to the same carbon of the alkylene group are replaced by "=O".

"$C_1$-$C_5$ heteroalkylene" refers to straight chain $C_2$-$C_6$ alkylene groups where one or two —$CH_2$— groups are replaced with —S—, —S(O)—, —S(O)$_2$—, or —O— to give a heteroalkylene having one to five carbons provided that the heteroalkylene does not contain an —O—O—, —S—O—, —O—S—, or —S—S— group wherein the sulfur atom(s) are optionally oxidized to form S(O) or S(O)$_2$.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{47}C(O)$alkyl, —$NR^{47}C(O)$ substituted alkyl, —$NR^{47}C(O)$cycloalkyl, —$NR^{47}C(O)$ substituted cycloalkyl, —$NR^{47}C(O)$cycloalkenyl, —$NR^{47}C(O)$ substituted cycloalkenyl, —$NR^{47}C(O)$alkenyl, —$NR^{47}C(O)$ substituted alkenyl, —$NR^{47}C(O)$alkynyl, —$NR^{47}C(O)$ substituted alkynyl, —$NR^{47}C(O)$aryl, —$NR^{47}C(O)$ substituted aryl, —$NR^{47}C(O)$heteroaryl, —$NR^{47}C(O)$ substituted heteroaryl, —$NR^{47}C(O)$heterocyclic, and —$NR^{47}C(O)$ substituted heterocyclic wherein $R^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cylcoalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —$C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —$C(S)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{47}C(O)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —$NR^{47}C(S)NR^{50}R^{51}$ where R is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where R$^{47}$ is hydrogen or alkyl and R$^{50}$ and R$^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where R$^{50}$, R$^{51}$, and R$^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{50}$ and R$^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR$^{47}$C(O)O-alkyl, —NR$^{47}$C(O)O-substituted alkyl, —NR$^{47}$C(O)O-alkenyl, —NR$^{47}$C(O)O-substituted alkenyl, —NR$^{47}$C(O)O-alkynyl, —NR$^{47}$C(O)O-substituted alkynyl, —NR$^{47}$C(O)O-aryl, —NR$^{47}$C(O)O-substituted aryl, —NR$^{47}$C(O)O-cycloalkyl, —NR$^{47}$C(O)O-substituted cycloalkyl, —NR$^{47}$C(O)O-cycloalkenyl, —NR$^{47}$C(O)O-substituted cycloalkenyl, —NR$^{47}$C(O)O-heteroaryl, —NR$^{47}$C(O)O-substituted heteroaryl, —NR$^{47}$C(O)O-heterocyclic, and —NR$^{47}$C(O)O-substituted heterocyclic wherein R$^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Cycloalkylene" and "substituted cycloalkylene" refer to divalent cycloalkyl and substituted cycloalkyl groups as defined above. Preferred cycloalkylene and substituted cycloalkylene groups have three to six carbon atoms.

"Heterocycloalkylene" and "substituted heterocycloalkylene" refer to cycloalkylene and substituted cycloalkylene groups as defined above having from 1 to 4 ring heteroatoms selected from the group consisting of nitrogen, sulfur, or oxygen.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{53}$C(=NR$^{53}$)N(R$^{53}$)$_2$ where each R$^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R$^{53}$ groups attached to a common guanidino nitrogen atom are optionally joined together with the nitrogen bound thereto to form a heterocyclic or substituted heterocyclic group, provided that at least one R$^{53}$ is not hydrogen, and wherein said substituents are as defined herein.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Haloalkoxy" refers to alkoxy groups substituted with 1 to 5, 1 to 3, or 1 to 2 halo groups, wherein alkoxy and halo are as defined herein.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O—).

"Spirocycloalkyl" and "spiro ring systems" refers to divalent cyclic groups from 3 to 10 carbon atoms having a cycloalkyl ring with a spiro union (the union formed by a single atom which is the only common member of the rings) as exemplified by the following structure:

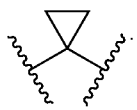

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-SO$_2$—, phenyl-SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Isomer" refers to tautomerism, conformational isomerism, geometric isomerism, stereoisomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers, diasteromers, and mixtures thereof, such as racemic mixtures. As another example, the compounds and prodrugs of the invention may exist in several tautomeric forms, including the enol form, the keto form, and mixtures thereof.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Prodrug" refers to art recognized modifications to one or more functional groups which functional groups are metabolized in vivo to provide a compound of this invention or an active metabolite thereof. Such functional groups are well known in the art including acyl groups for hydroxyl and/or amino substitution, esters of mono-, di- and tri-phosphates wherein one or more of the pendent hydroxyl groups have been converted to an alkoxy, a substituted alkoxy, an aryloxy or a substituted aryloxy group, and the like.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "HANDBOOK OF PHARMACEUTICALLY ACCEPTABLE SALTS", (2002), Verlag Helvetica Chimica Acta, Zürich, Switzerland), for an extensive discussion of pharmaceutical salts, their selection, preparation, and use.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers or other compounds arrived at by defining substituents with further substituents to themselves (e.g., substituted aryl having a substituted aryl group or another group as a substituent which is itself substituted with a substituted aryl group or another group, which is further substituted by a substituted aryl group or another group etc.) are not intended for inclusion herein. In such cases, the maximum number of such substitutions is four. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. Studies in animal models generally may be used for guidance regarding effective dosages for treatment of diseases such as diarrhea and PKD. In general, one will desire to administer an amount of the compound that is effective to achieve a serum level commensurate with the concentrations found to be effective in vitro. Thus, where a compound is found to demonstrate in vitro activity, for example as noted in the Tables discussed below one can extrapolate to an effective dosage for administration in vivo. These considerations, as well as effective formulations and administration procedures are well known in the art and are described in standard textbooks. Consistent with this definition and as used herein, the term "therapeutically effective amount"is an amount sufficient to treat a specified disorder or disease or alternatively to obtain a pharmacological response such as inhibiting function CFTR.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

B. Compounds of the Invention

The present invention relates to hydrazone-containing compounds which are CFTR inhibitors. In one aspect, the invention relates to a compound of formula I:

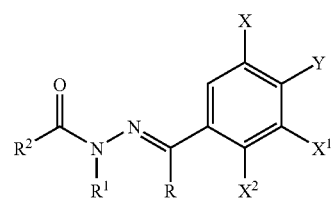

wherein:
R is selected from the group consisting of hydrogen, alkyl and substituted alkyl;
$R^1$ is selected from the group consisting of hydrogen, alkyl, substituted alkyl, aryl, substituted aryl, alkenyl, substituted alkenyl, alkynyl, substituted alkynyl, cycloalkyl, substituted cycloalkyl, heterocyclic, substituted heterocyclic, heteroaryl and substituted heteroaryl;
or R and $R^1$ together with the atoms bound thereto, form a heterocycle or substituted heterocycle;
$R^2$ is selected from the group consisting of alkyl, substituted alkyl, aryl, substituted aryl, cycloalkyl, substituted cycloalkyl, heterocyclic, substituted heterocyclic, heteroaryl and substituted heteroaryl;
or R and $R^2$ together with the atoms bound thereto, form a heterocycle or substituted heterocycle;
or $R^1$ and $R^2$ together with the atoms bound thereto, form a heterocycle or substituted heterocycle;
X and $X^1$ are independently selected from the group consisting of hydrogen, halo, hydroxyl, nitro, alkyl, substituted alkyl, aryl, substituted aryl, alkoxy, substituted alkoxy, cycloalkyl, substituted cycloalkyl, heterocyclic, substituted heterocyclic, heteroaryl, substituted heteroaryl, carboxyl, and carboxyl ester;
$X^2$ is selected from the group consisting of hydrogen, halo and hydroxyl; and
Y is selected from the group consisting of hydrogen, halo, hydroxyl, alkoxy and substituted alkoxy;
or either of X or $X^1$ and Y together with the atoms bound thereto, form an aryl, substituted aryl, heteroaryl or substituted heteroaryl; or
a pharmaceutically acceptable salt, isomer, prodrug, or tautomer thereof;
wherein said compound exhibits an $IC_{50}$ of less than 30 μM or a greater than 35% inhibition at 50 μM in a T84 assay, provided that the compound does not have an $IC_{50}$ greater than 30 μM, or a greater than 30% inhibition at 20 μM in a FRT assay;

with the provisos that:
(1) $R^2$ is not —$CR^{20}H$ (substituted amino), wherein $R^{20}$ is hydrogen, methyl, substituted alkyl or substituted phenyl; and said substituted amino does not include substituted amino wherein the nitrogen is a ring atom in a heterocycle, substituted heterocycle, heteroaryl or substituted heteroaryl; and
(2) the compound is not

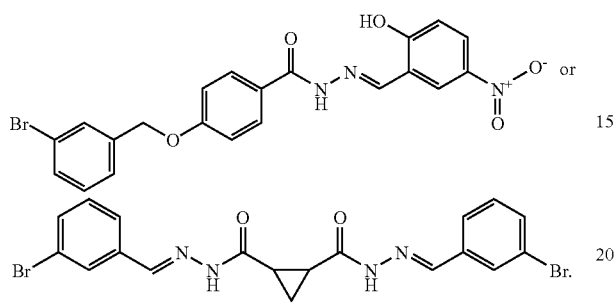

In another embodiment, the compounds of formula I exhibit at least 30% inhibition of maximally stimulated CFTR iodide influx as determined by measurement of a relative YFP fluorescence versus time when tested at 20 μM in the assay described herein.

In another embodiment, the compounds of formula I exhibit an $IC_{50}$ of less than 30 μM when tested in the T84 assay described herein. Or alternatively, the compounds of formula I exhibit at least 35% inhibition at 50 μM when tested in the T84 assay described herein, provided that the compound does not have an $IC_{50}$ greater than 30 μM.

In a certain embodiment, R is selected from the group consisting of hydrogen and methyl and $R^1$ is selected from the group consisting of hydrogen, alkyl, substituted alkyl, alkenyl and substituted alkenyl.

In a certain embodiment, X and $X^1$ are halo; Y is hydroxyl; and $X^2$ is hydrogen.

In a another embodiment, R and $R^1$ together with the atoms bound thereto, form a heterocycle or substituted heterocycle.

In a certain embodiment, the invention relates to a compound of formula I represented by formula II:

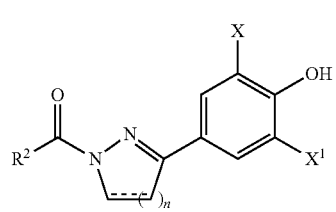

wherein:
X and $X^1$ are independently selected from the group consisting of hydrogen and halo;
---is a single or double bond;
n is 1 or 2; and
when ---is a double bond, n is 1; and when ---is a single bond, n is 1 or 2.

In a yet another embodiment, R and $R^2$ together with the atoms bound thereto, form a heterocycle or substituted heterocycle.

In a certain embodiment, the invention relates to a compound of formula I represented by formula III:

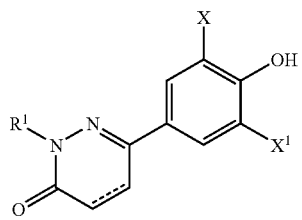

wherein:
X and $X^1$ are halo; and
---is a single or double bond.
In a certain embodiment,

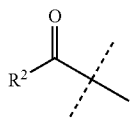

is represented by

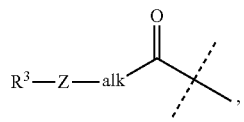

wherein:
$R^3$ is selected from the group consisting of hydrogen, alkyl, substituted alkyl, aryl, substituted aryl, cycloalkyl, substituted cycloalkyl, heterocyclic, substituted heterocyclic, heteroaryl and substituted heteroaryl;
Z is selected from the group consisting of a direct bond, O, S and $SO_2$; and
alk is selected from the group consisting of alkylene, substituted alkylene, cycloalkylene, substituted cycloalkylene, heterocycloalkylene or substituted heterocycloalkylene.

In a certain embodiment, the invention relates to a compound of formula I represented by formula IV:

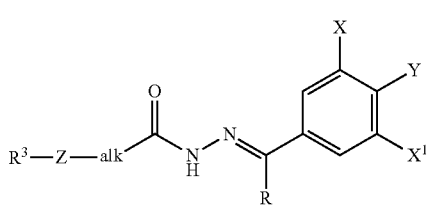

wherein:
R is selected from the group consisting of hydrogen, alkyl and substituted alkyl;
$R^3$ is selected from the group consisting of hydrogen, alkyl, substituted alkyl, aryl, substituted aryl, cycloalkyl, substituted cycloalkyl, heterocyclic, substituted heterocyclic, heteroaryl and substituted heteroaryl;
Y is selected from the group consisting of hydrogen, fluoro and hydroxyl;
or either of X or $X^1$ and Y together with the atoms bound thereto, form an aryl, substituted aryl, heteroaryl or substituted heteroaryl;

Z is selected from the group consisting of a direct bond, O, S and $SO_2$; and alk is selected from the group consisting of alkylene, substituted alkylene, cycloalkylene, substituted cycloalkylene, heterocycloalkylene or substituted heterocycloalkylene.

In a certain embodiment, alk is methylene.

In a certain embodiment, R is selected from the group consisting of hydrogen and methyl.

In a certain embodiment, X and $X^1$ are halo; Y is hydroxyl; $X^2$ is hydrogen; and R is selected from the group consisting of hydrogen and methyl.

In a certain embodiment, the invention relates to a compound of formula I represented by formula V:

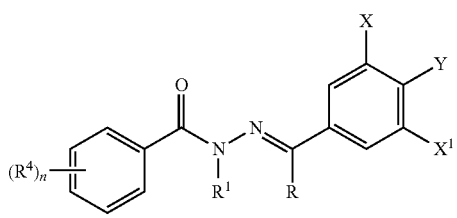

V wherein:

R is selected from the group consisting of hydrogen, alkyl and substituted alkyl;

$R^1$ is selected from the group consisting of hydrogen, alkyl, substituted alkyl, alkenyl and substituted alkenyl;

each $R^4$ is independently selected from the group consisting of hydrogen, halo, alkyl, substituted alkyl, alkoxy, substituted alkoxy, aryl, substituted aryl, cycloalkyl, substituted cycloalkyl, heterocyclic, substituted heterocyclic, heteroaryl, substituted heteroaryl, aryloxy, substituted aryloxy, cycloalkyloxy, substituted cycloalkyloxy and aminocarbonyl; or wherein two $R^4$ together with the atoms bound thereto, form an aryl, substituted aryl, cycloalkyl, substituted cycloalkyl, heterocyclic, substituted heterocyclic, heteroaryl or substituted heteroaryl; and n is 0, 1, 2 or 3.

In a certain embodiment, R is selected from the group consisting of hydrogen and methyl and $R^1$ is hydrogen.

In a certain embodiment, X and $X^1$ are halo; Y is hydroxyl; $X^2$ is hydrogen; and R is selected from the group consisting of hydrogen and methyl.

In a certain embodiment, the invention relates to a compound of formula I represented by formula VI:

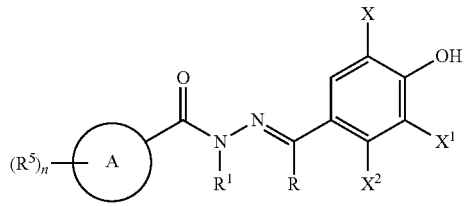

VI wherein:

A is heteroaryl or substituted heteroaryl;

$R^1$ is selected from the group consisting of hydrogen, alkyl, substituted alkyl, alkenyl and substituted alkenyl;

each $R^5$ is independently selected from the group consisting of hydrogen, halo, alkyl, substituted alkyl, alkoxy, substituted alkoxy, aryl, substituted aryl, cycloalkyl, substituted cycloalkyl, heterocyclic, substituted heterocyclic, heteroaryl, substituted heteroaryl, aryloxy, substituted aryloxy, cycloalkyloxy, substituted cycloalkyloxy and aminocarbonyl; or wherein two $R^5$ are taken together to form an aryl, substituted aryl, cycloalkyl, substituted cycloalkyl, heterocyclic, substituted heterocyclic, heteroaryl or substituted heteroaryl;

n is 0, 1, 2 or 3; and $X^2$ is selected from the group consisting of hydrogen and hydroxyl.

In a certain embodiment, R and $R^1$ are hydrogen.

In a certain embodiment, X and $X^1$ are halo and $X^2$ is hydrogen.

It will be appreciated by one of skill in the art that the embodiments summarized above may be used together in any suitable combination to generate additional embodiments not expressly recited above, and that such embodiments are considered to be part of the present invention.

Those of skill in the art will appreciate that the compounds described herein may include functional groups that can be masked with progroups to create prodrugs. Such prodrugs are usually, but need not be, pharmacologically inactive until converted into their active drug form. The compounds described in this invention may include promoieties that are hydrolyzable or otherwise cleavable under conditions of use. For example, ester groups commonly undergo acid-catalyzed hydrolysis to yield the parent carboxylic acid when exposed to the acidic conditions of the stomach or base-catalyzed hydrolysis when exposed to the basic conditions of the intestine or blood. Thus, when administered to a subject orally, compounds that include ester moieties can be considered prodrugs of their corresponding carboxylic acid, regardless of whether the ester form is pharmacologically active.

Prodrugs designed to cleave chemically in the stomach to the active compounds can employ progroups including such esters. Alternatively, the progroups can be designed to metabolize in the presence of enzymes such as esterases, amidases, lipolases, and phosphatases, including ATPases and kinase, etc. Progroups including linkages capable of metabolizing in vivo are well known and include, by way of example and not limitation, ethers, thioethers, silylethers, silylthioethers, esters, thioesters, carbonates, thiocarbonates, carbamates, thiocarbamates, ureas, thioureas, and carboxamides.

In the prodrugs, any available functional moiety can be masked with a progroup to yield a prodrug. Functional groups within the compounds of the invention that can be masked with progroups include, but are not limited to, amines (primary and secondary), hydroxyls, sulfanyls (thiols), and carboxyls. A wide variety of progroups suitable for masking functional groups in active compounds to yield prodrugs are well-known in the art. For example, a hydroxyl functional group can be masked as a sulfonate, ester, or carbonate promoiety, which can be hydrolyzed in vivo to provide the hydroxyl group. An amino functional group can be masked as an amide, carbamate, imine, urea, phosphenyl, phosphoryl, or sulfenyl promoiety, which can be hydrolyzed in vivo to provide the amino group. A carboxyl group can be masked as an ester (including silyl esters and thioesters), amide, or hydrazone promoiety, which can be hydrolyzed in vivo to provide the carboxyl group. Other specific examples of suitable progroups and their respective promoieties will be apparent to those of skill in the art. All of these progroups, alone or in combinations, can be included in the prodrugs.

As noted above, the identity of the progroup is not critical, provided that it can be metabolized under the desired conditions of use, for example, under the acidic conditions found in the stomach and/or by enzymes found in vivo, to yield a biologically active group, e.g., the compounds as described herein. Thus, skilled artisans will appreciate that the progroup can comprise virtually any known or later-discovered hydroxyl, amine or thiol protecting group. Non-limiting examples of suitable protecting groups can be found, for example, in PROTECTIVE GROUPS IN ORGANIC SYNTHESIS, Greene & Wuts, 2nd Ed., John Wiley & Sons, New York, 1991.

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, and targeting-specific transporters. Groups capable of imparting prodrugs with these characteristics are well-known and are described, for example, in Ettmayer et al. (2004), J. Med. Chem. 47(10):2393-2404. All of the various groups described in these references can be utilized in the prodrugs described herein.

As noted above, progroup(s) may also be selected to increase the water solubility of the prodrug as compared to the active drug. Thus, the progroup(s) may include or can be a group(s) suitable for imparting drug molecules with improved water solubility. Such groups are well-known and include, by way of example and not limitation, hydrophilic groups such as alkyl, aryl, and arylalkyl, or cycloheteroalkyl groups substituted with one or more of an amine, alcohol, a carboxylic acid, a phosphorous acid, a sulfoxide, a sugar, an amino acid, a thiol, a polyol, an ether, a thioether, and a quaternary amine salt. Numerous references teach the use and synthesis of prodrugs, including, for example, Ettmayer et al., supra and Bungaard et al. (1989) J. Med. Chem. 32(12): 2503-2507.

One of ordinary skill in the art will appreciate that many of the compounds of the invention and prodrugs thereof, may exhibit the phenomena of tautomerism, conformational isomerism, geometric isomerism, and/or optical isomerism. For example, the compounds and prodrugs of the invention may include one or more chiral centers and/or double bonds and as a consequence may exist as stereoisomers, such as double-bond isomers (i.e., geometric isomers), enantiomers, diasteromers, and mixtures thereof, such as racemic mixtures. As another example, the compounds and prodrugs of the invention may exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it should be understood that the invention encompasses any tautomeric, conformational isomeric, optical isomeric, and/or geometric isomeric forms of the compounds or prodrugs having one or more of the utilities described herein, as well as mixtures of these various different isomeric forms.

Depending upon the nature of the various substituents, the compounds and prodrugs of the invention can be in the form of salts. Such salts include salts suitable for pharmaceutical uses ("pharmaceutically-acceptable salts"), salts suitable for veterinary uses, etc. Such salts can be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenyl-propionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or coordinates with an organic base (e.g., ethanolamine, diethanolamine, triethanolamine, N-methylglucamine, morpholine, piperidine, dimethylamine, diethylamine, triethylamine, and ammonia).

In one embodiment, this invention provides a compound, isomer, tautomer, prodrug, or pharmaceutically acceptable salt thereof, selected from Tables 1-6, provided that the compound is not (E)-2-(4-chlorophenylamino)-N'-(3,5-dibromo-4-hydroxybenzylidene)acetohydrazide.

TABLE 1

| Comp. | Structure | R³ | Z' | alk | R | X | X¹ | Y | Name |
|---|---|---|---|---|---|---|---|---|---|
| 1 | 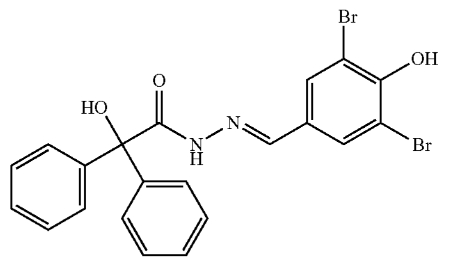 | H | O | C(C₆H₅)₂ | H | Br | Br | OH | (E)-N'-(3,5-dibromo-4-hydroxybenzylidene)-2-hydroxy-2,2-diphenylacetohydrazide |
| 2 | 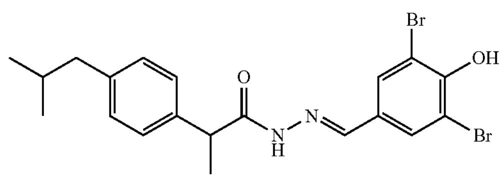 | 4-isobutyl-phenyl | — | CH(CH₃) | H | Br | Br | OH | (E)-N'-(3,5-dibromo-4-hydroxybenzylidene)-2-(4-isobutylphenyl)propanehydrazide |
| 4 | 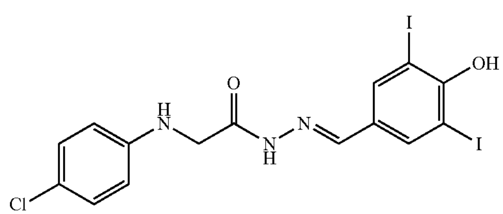 | 4-chlorophenyl | NH | CH₂ | H | I | I | OH | (E)-2-(4-chlorophenylamino)-N'-(3,5-diiodo-4-hydroxybenzylidene)acetohydrazide |

TABLE 1-continued

III

R³—Z'—alk—C(=O)—NH—N=C(R)—[3,5-X,X¹-4-Y-phenyl]

| Comp. | Structure | R³ | Z' | alk | R | X | X¹ | Y | Name |
|---|---|---|---|---|---|---|---|---|---|
| 6 | 3,5-dibromo-4-hydroxyphenyl-CH=N-NH-C(=O)-CH(CH₃)-O-(2,4-dichlorophenyl) | 2,4-dichlorophenyl | O | CH(CH₃) | H | Br | Br | OH | (E)-N'-(3,5-dibromo-4-hydroxybenzylidene)-2-(2,4-dichlorophenoxy)propanehydrazide |
| 10 | 3,5-dibromo-4-hydroxyphenyl-CH=N-NH-C(=O)-CH₂-NH-(3,4-dichlorophenyl) | 3,4-dichlorophenyl | NH | CH₂ | H | Br | Br | OH | (E)-N'-(3,5-dibromo-4-hydroxybenzylidene)-2-(3,4-dichlorophenylamino)acetohydrazide |
| 11 | 3,5-dibromo-4-hydroxyphenyl-CH=N-NH-C(=O)-CH₂-O-(4-(1H-pyrrol-1-yl)phenyl) | 4-(1H-pyrrol-1-yl)phenyl | O | CH₂ | H | Br | Br | OH | (E)-2-(4-(1H-pyrrol-1-yl)phenoxy)-N'-(3,5-dibromo-4-hydroxybenzylidene)acetohydrazide |

TABLE 1-continued

III

| Comp. | Structure | R³ | Z' | alk | R | X | X¹ | Y | Name |
|---|---|---|---|---|---|---|---|---|---|
| 12 | 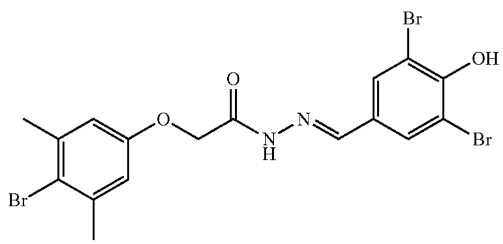 | 4-bromo-3,5-dimethylphenyl | O | CH₂ | H | Br | Br | OH | (E)-2-(4-bromo-3,5-dimethylphenoxy)-N'-(3,5-dibromo-4-hydroxybenzylidene)acetohydrazide |
| 13 | 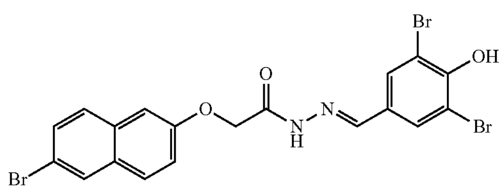 | 6-bromonaphthalen-2-yl | O | CH₂ | H | Br | Br | OH | (E)-2-(6-bromonaphthalen-2-yloxy)-N'-(3,5-dibromo-4-hydroxybenzylidene)acetohydrazide |
| 22 | 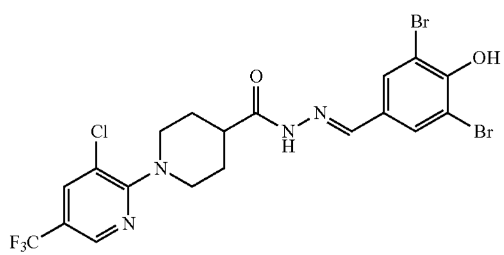 | 3-chloro-5-(trifluoromethyl)pyridin-2-yl | — | (piperidine) | H | Br | Br | OH | (E)-1-(3-chloro-5-(trifluoromethyl)pyridin-2-yl)-N'-(3,5-dibromo-4-hydroxybenzylidene)piperidine-4-carbohydrazide |

TABLE 1-continued

III

| Comp. | Structure | R³ | Z' | alk | R | X | X¹ | Y | Name |
|---|---|---|---|---|---|---|---|---|---|
| 23 | 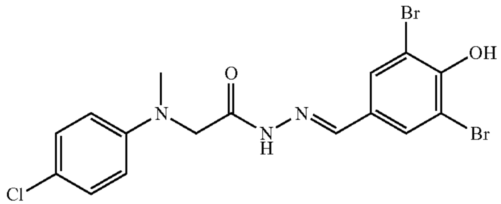 | 4-chlorophenyl | N(CH₃) | CH₂ | H | Br | Br | OH | (E)-2-((4-chlorophenyl)(methyl)amino)-N'-(3,5-dibromo-4-hydroxybenzylidene)acetohydrazide |
| 29 | 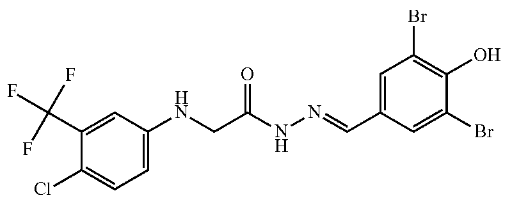 | 4-chloro-3-(trifluoromethyl)phenyl | NH | CH₂ | H | Br | Br | OH | (E)-2-(4-chloro-3-(trifluoromethyl)phenylamino)-N'-(3,5-dibromo-4-hydroxybenzylidene)acetohydrazide |
| 30 | 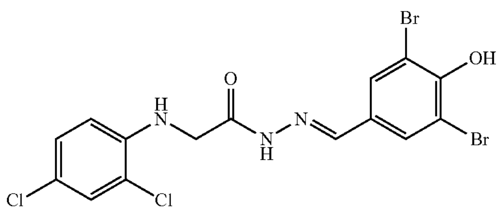 | 2,4-dichlorophenyl | NH | CH₂ | H | Br | Br | OH | (E)-N'-(3,5-dibromo-4-hydroxybenzylidene)-2-(2,4-dichlorophenylamino)acetohydrazide |

TABLE 1-continued

III

| Comp. | Structure | $R^3$ | $Z'$ | alk | R | X | $X^1$ | Y | Name |
|---|---|---|---|---|---|---|---|---|---|
| 33 | 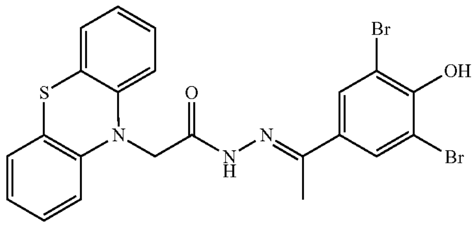 | 10H-phenothiazin-10-yl | — | $CH_2$ | $CH_3$ | Br | Br | OH | (E)-N'-(1-(3,5-dibromo-4-hydroxyphenyl)ethylidene)-2-(10H-phenothiazin-10-yl)acetohydrazide |
| 34 | 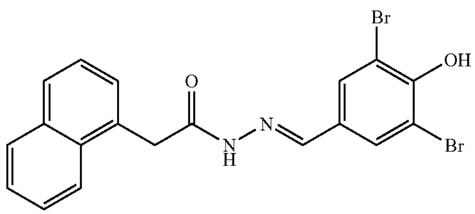 | naphthalen-1-yl | — | $CH_2$ | H | Br | Br | OH | (E)-N'-(3,5-dibromo-4-hydroxybenzylidene)-2-(naphthalen-1-yl)acetohydrazide |
| 40 | 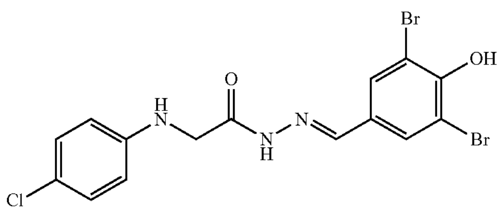 | 4-chlorophenyl | NH | $CH_2$ | H | Br | Br | OH | (E)-2-(4-chlorophenylamino)-N'-(3,5-dibromo-4-hydroxybenzylidene)acetohydrazide |

TABLE 1-continued

| Comp. | Structure | R³ | Z' | alk | R | X | X¹ | Y | Name |
|---|---|---|---|---|---|---|---|---|---|
| 43 | 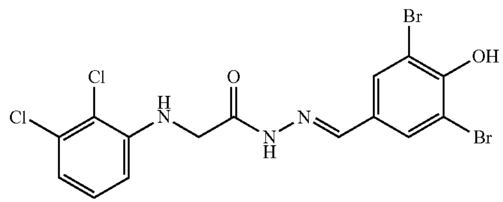 | 2,3-dichlorophenyl | NH | CH₂ | H | Br | Br | OH | (E)-N'-(3,5-dibromo-4-hydroxybenzylidene)-2-(2,3-dichlorophenylamino)acetohydrazide |
| 47 | 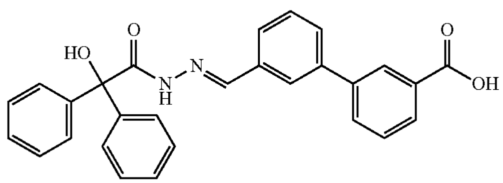 | H | O | C(C₆H₅)₂ | H | H | 3-(hydroxyoxo-methyl)phenyl | H | (E)-3'-((2-(2-hydroxy-2,2-diphenyl-acetyl)hydrazono)methyl)biphenyl-3-carboxylic acid |
| 48 | 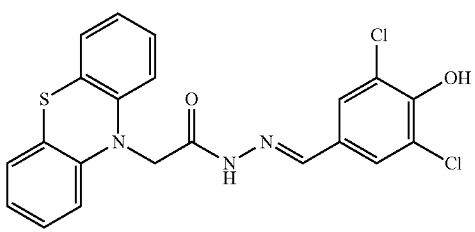 | 10H-phenothiazin-10-yl | — | CH₂ | H | Cl | Cl | OH | (E)-N'-(3,5-dichloro-4-hydroxybenzylidene)-2-(10H-phenothiazin-10-yl)acetohydrazide |

TABLE 1-continued

| Comp. | Structure | R³ | Z' | alk | R | X | X¹ | Y | Name |
|---|---|---|---|---|---|---|---|---|---|
| 50 | 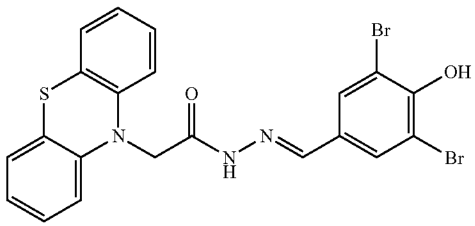 | 10H-phenothiazin-10-yl | — | CH₂ | H | Br | Br | OH | (E)-N'-(3,5-dibromo-4-hydroxybenzylidene)-2-(10H-phenothiazin-10-yl)acetohydrazide |
| 56 | 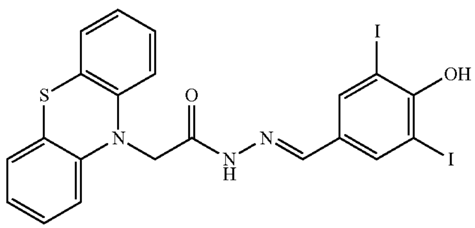 | 10H-phenothiazin-10-yl | — | CH₂ | H | I | I | OH | (E)-N'-(4-hydroxy-3,5-diiodobenzylidene)-2-(10H-phenothiazin-10-yl)acetohydrazide |
| 57 | 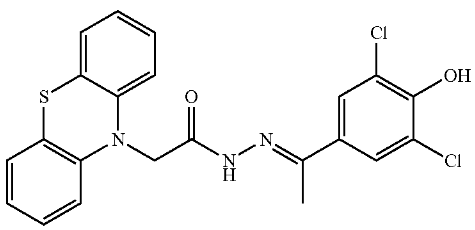 | 10H-phenothiazin-10-yl | — | CH₂ | CH₃ | Cl | Cl | OH | (E)-N'-(1-(3,5-dichloro-4-hydroxyphenyl)ethylidene)-2-(10H-phenothiazin-10-yl)acetohydrazide |

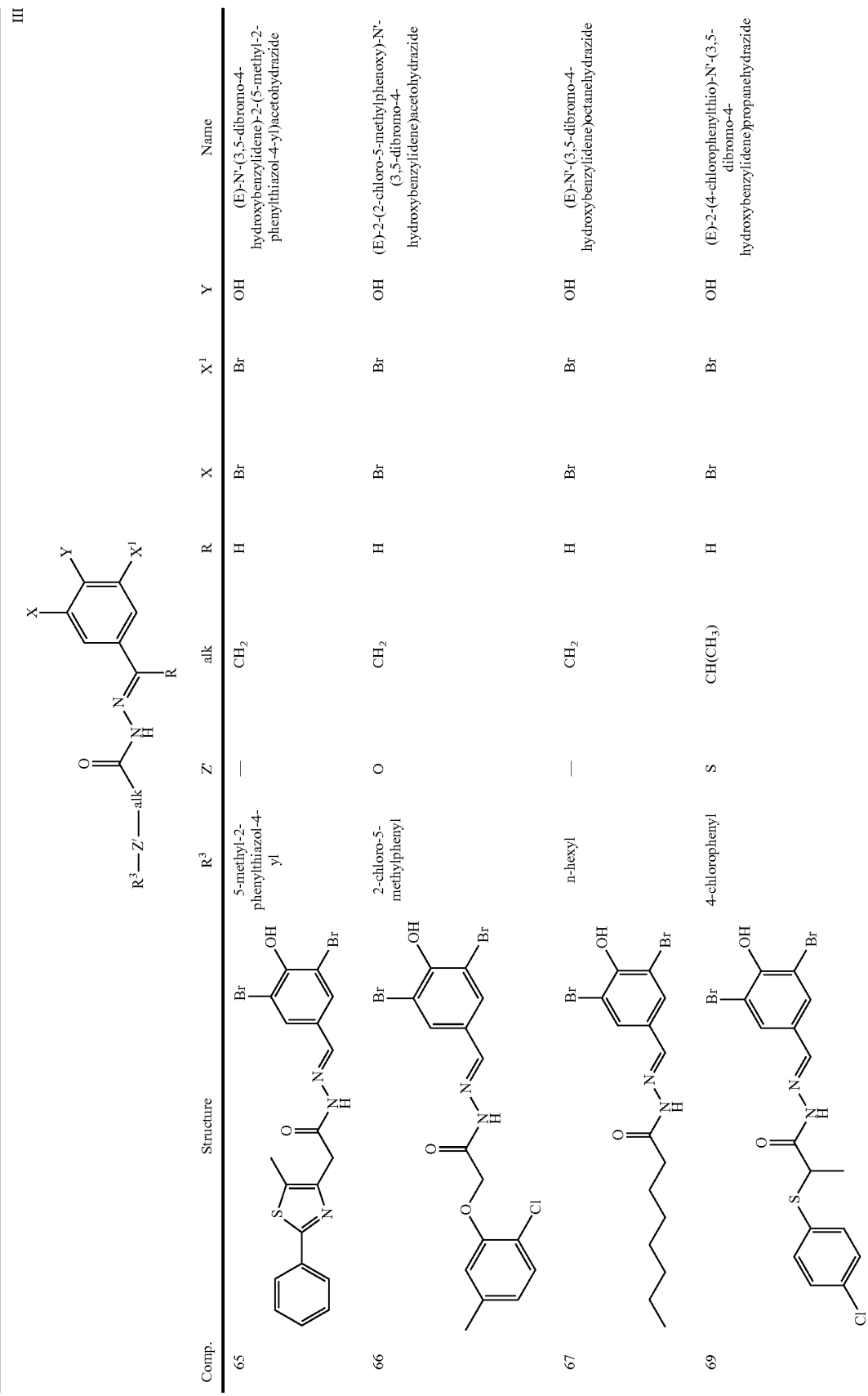

TABLE 1-continued

III

R³—Z'—alk—C(=O)—NH—N=C(R)—[phenyl with X, Y, X¹]

| Comp. | Structure | R³ | Z' | alk | R | X | X¹ | Y | Name |
|---|---|---|---|---|---|---|---|---|---|
| 77 | 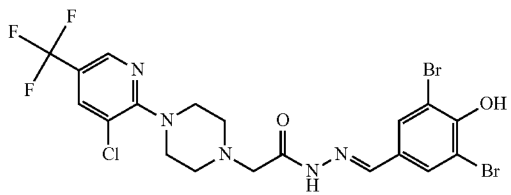 | 1-(3-chloro-5-(trifluoromethyl)pyridine-2-yl)piperazin-4-yl | — | CH₂ | H | Br | Br | OH | (E)-2-(4-(3-chloro-5-(trifluoromethyl)pyridin-2-yl)piperazin-1-yl)-N'-(3,5-dibromo-4-hydroxybenzylidene)acetohydrazide |
| 79 | 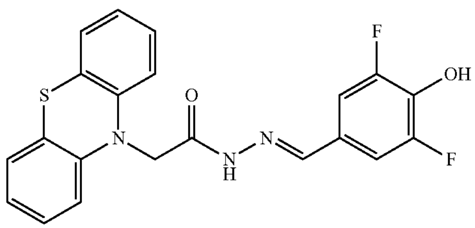 | 10H-phenothiazin-10-yl | — | CH₂ | H | F | F | OH | (E)-N'-(3,5-difluoro-4-hydroxybenzylidene)-2-(10H-phenothiazin-10-yl)acetohydrazide |
| 88 | 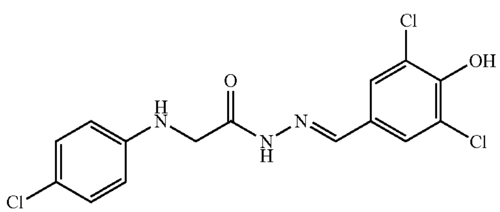 | 4-chlorophenyl | NH | CH₂ | H | Cl | Cl | OH | (E)-2-(4-chlorophenylamino)-N'-(3,5-dichloro-4-hydroxybenzylidene)acetohydrazide |

TABLE 1-continued

| Comp. | Structure | R³ | Z' | alk | R | X | X¹ | Y | Name |
|---|---|---|---|---|---|---|---|---|---|
| 90 | (3,5-dibromo-4-hydroxybenzylidene hydrazide with 4-iodophenylamino acetyl) | 4-iodophenyl | NH | CH₂ | H | Br | Br | OH | (E)-N'-(3,5-dibromo-4-hydroxybenzylidene)-2-(4-iodophenylamino)acetohydrazide |
| 96 | (3,5-dibromo-4-hydroxybenzylidene hydrazide with 4-(trifluoromethyl)phenylamino acetyl) | 4-(trifluoromethyl)phenyl | NH | CH₂ | H | Br | Br | OH | (E)-N'-(3,5-dibromo-4-hydroxybenzylidene)-2-(4-(trifluoromethyl)phenylamino)acetohydrazide |
| 99 | (3,5-dibromo-4-hydroxybenzylidene hydrazide with 4-(trifluoromethoxy)phenylamino acetyl) | 4-(trifluoromethoxy)phenyl | NH | CH₂ | H | Br | Br | OH | (E)-N'-(3,5-dibromo-4-hydroxybenzylidene)-2-(4-(trifluoromethoxy)phenylamino)acetohydrazide |
| 102 | (3,5-dibromo-4-hydroxybenzylidene hydrazide with 3-chlorophenyl acetyl) | 3-chlorophenyl | — | CH₂ | H | Br | Br | OH | (E)-2-(3-chlorophenyl)-N'-(3,5-dibromo-4-hydroxybenzylidene)acetohydrazide |

TABLE 1-continued

III

R³—Z'—alk—C(=O)—NH—N=C(R)—[3,5-X,X¹-4-Y-phenyl]

| Comp. | Structure | R³ | Z' | alk | R | X | X¹ | Y | Name |
|---|---|---|---|---|---|---|---|---|---|
| 111 | 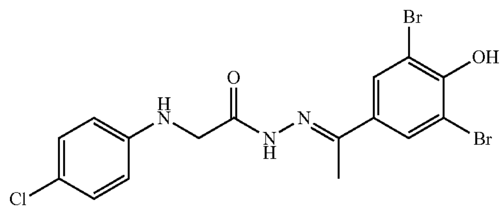 | 4-chlorophenyl | NH | CH₂ | CH₃ | Br | Br | OH | (E)-2-(4-chlorophenylamino)-N'-(1-(3,5-dibromo-4-hydroxyphenyl)ethylidene)acetohydrazide |
| 113 | 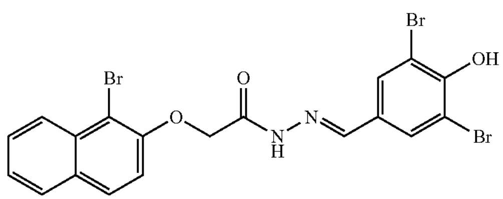 | 1-bromonaphthalen-2-yl | O | CH₂ | H | Br | Br | OH | (E)-2-(1-bromonaphthalen-2-yloxy)-N'-(3,5-dibromo-4-hydroxybenzylidene)acetohydrazide |
| 117 | 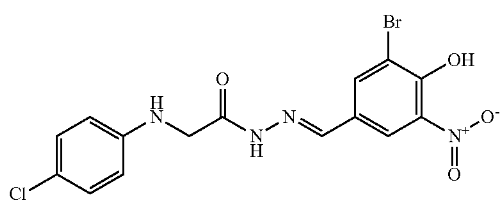 | 4-chlorophenyl | NH | CH₂ | H | Br | NO₂ | OH | (E)-N'-(3-bromo-4-hydroxy-5-nitrobenzylidene)-2-(4-chlorophenylamino)acetohydrazide |

TABLE 1-continued

III

| Comp. | Structure | R³ | Z' | alk | R | X | X¹ | Y | Name |
|---|---|---|---|---|---|---|---|---|---|
| 122 | ![structure] | 2,4-dichlorophenyl | O | CH₂ | H | Br | Br | OH | (E)-N'-(3,5-dibromo-4-hydroxybenzylidene)-2-(2,4-dichlorophenoxy)acetohydrazide |
| 128 | ![structure] | 4-bromophenyl | O | CH₂ | H | Br | Br | OH | (E)-2-(4-bromophenoxy)-N'-(3,5-dibromo-4-hydroxybenzylidene)acetohydrazide |
| 171 | ![structure] | 4-chlorophenyl | SO₂ | 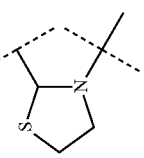* | H | Br | Br | OH | (E)-3-(4-chlorophenylsulfonyl)-N'-(3,5-dibromo-4-hydroxybenzylidene)thiazolidine-2-carbohydrazide |

*nitrogen of the thiazolidine is attached to sulfonyl.

TABLE 1-continued

| Comp. | Structure | R³ | Z' | alk | R | X | X¹ | Y | Name |
|---|---|---|---|---|---|---|---|---|---|
| 173 | (structure) | 2,2-dimethyl-2,3-dihydrobenzofuran-7-yl | O | CH₂ | H | Br | Br | OH | (E)-N'-(3,5-dibromo-4-hydroxybenzylidene)-2-(2,2-dimethyl-2,3-dihydrobenzofuran-7-yloxy)acetohydrazide |
| 176 | (structure) | 7-methyl-2,3-dihydro-1H-inden-4-yl | O | CH₂ | H | Br | Br | OH | (E)-N'-(3,5-dibromo-4-hydroxybenzylidene)-2-(7-methyl-2,3-dihydro-1H-inden-4-yloxy)acetohydrazide |
| 177 | (structure) | 4-chlorophenyl | — | (cyclohexane) | H | Br | Br | OH | (E)-4-(4-chlorophenyl)-N'-(3,5-dibromo-4-hydroxybenzylidene)cyclohexanecarbohydrazide |

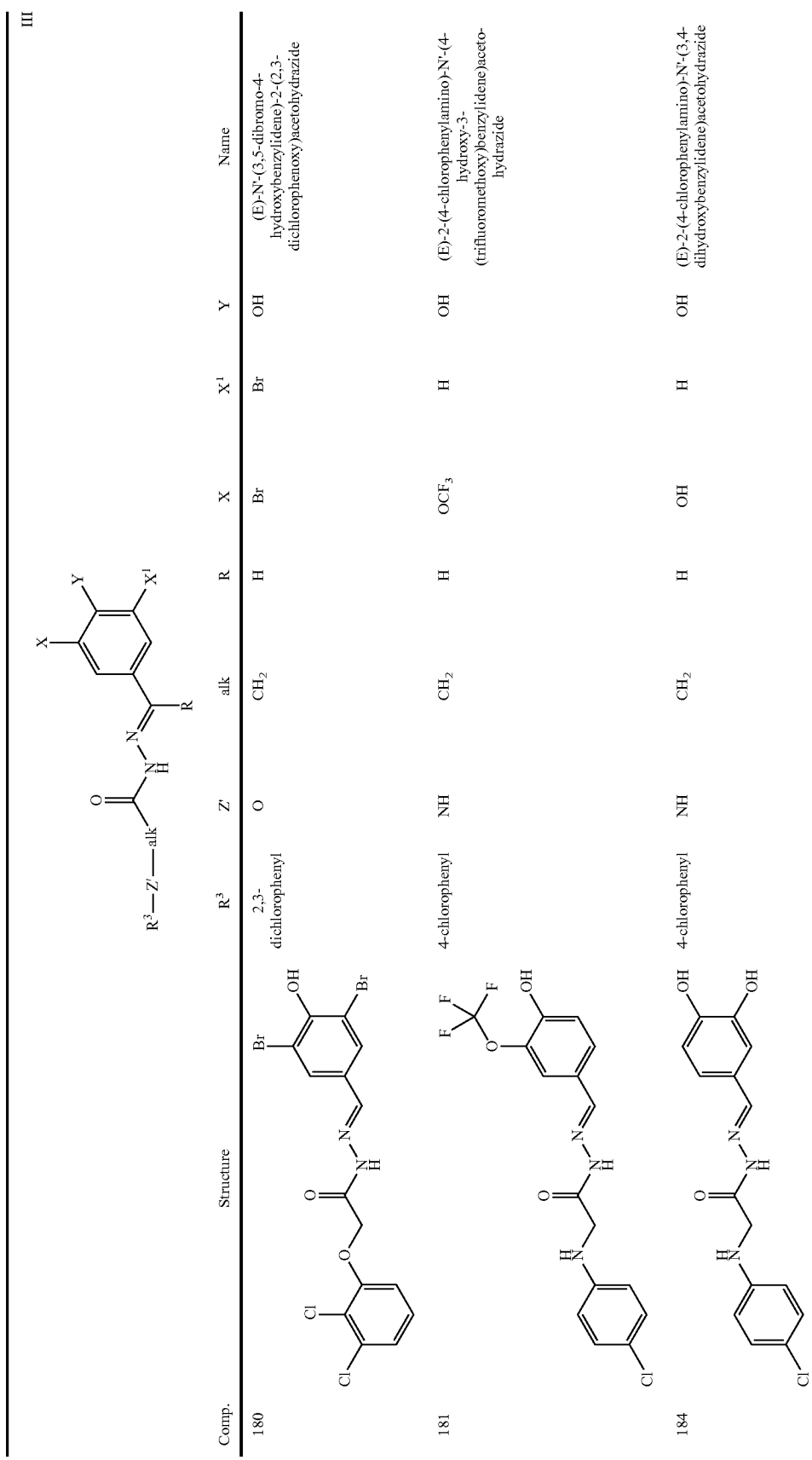

TABLE 1-continued

III

| Comp. | Structure | R³ | Z' | alk | R | X | X¹ | Y | Name |
|---|---|---|---|---|---|---|---|---|---|
| 185 | (3,5-dibromo-4-hydroxyphenyl)methylene hydrazide with naphthalen-1-yloxy acetyl | naphthalen-1-yl | O | CH₂ | H | Br | Br | OH | (E)-N'-(3,5-dibromo-4-hydroxybenzylidene)-2-(naphthalen-1-yloxy)acetohydrazide |
| 194 | (3,5-dibromo-4-hydroxyphenyl)methylene hydrazide with 4-ethylphenoxy acetyl | 4-ethylphenyl | O | CH₂ | H | Br | Br | OH | (E)-N'-(3,5-dibromo-4-hydroxybenzylidene)-2-(4-ethylphenoxy)acetohydrazide |
| 197 | (3,5-dibromo-4-hydroxyphenyl)methylene hydrazide with 4-(trifluoromethoxy)phenoxy acetyl | 4-(trifluoromethoxy)phenyl | O | CH₂ | H | Br | Br | OH | (E)-N'-(3,5-dibromo-4-hydroxybenzylidene)-2-(4-(trifluoromethoxy)phenoxy)acetohydrazide |
| 201 | (3,5-dibromo-4-hydroxyphenyl)methylene hydrazide with 3-chlorophenylamino acetyl | 3-chlorophenyl | NH | CH₂ | H | Br | Br | OH | (E)-2-(3-chlorophenylamino)-N'-(3,5-dibromo-4-hydroxybenzylidene)acetohydrazide |

TABLE 1-continued

III

R³—Z'—alk—C(=O)—NH—N=C(R)—[phenyl with X, Y, X¹ substituents]

| Comp. | Structure | R³ | Z' | alk | R | X | X¹ | Y | Name |
|---|---|---|---|---|---|---|---|---|---|
| 203 | 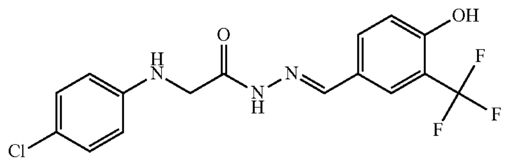 | 4-chlorophenyl | NH | CH₂ | H | CF₃ | H | OH | (E)-2-(4-chlorophenylamino)-N'-(4-hydroxy-3-(trifluoromethyl)benzylidene)acetohydrazide |
| 206 | 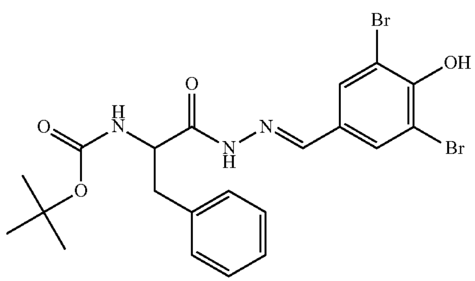 | tert-butoxycarbonyl | NH | CH(CH₂C₆H₅) | H | Br | Br | OH | (E)-tert-butyl 1-(2-(3,5-dibromo-4-hydroxybenzylidene)hydrazinyl)-1-oxo-3-phenylpropan-2-ylcarbamate |
| 209 | 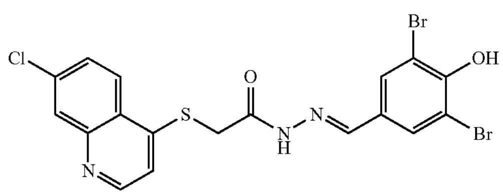 | 7-chloro-quinolin-4-yl | S | CH₂ | H | Br | Br | OH | (E)-2-(7-chloroquinolin-4-ylthio)-N'-(3,5-dibromo-4-hydroxybenzylidene)acetohydrazide |

TABLE 1-continued

| Comp. | Structure | R³ | Z' | alk | R | X | X¹ | Y | Name |
|---|---|---|---|---|---|---|---|---|---|
| 213 | 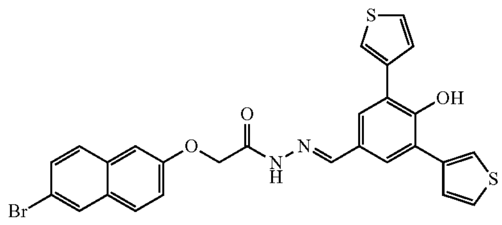 | 6-bromonaphthalen-2-yl | O | CH₂ | H | thiophen-3-yl | thiophen-3-yl | OH | (E)-2-(6-bromonaphthalen-2-yloxy)-N'-(4-hydroxy-3,5-di(thiophen-3-yl)benzylidene)acetohydrazide |
| 228 | 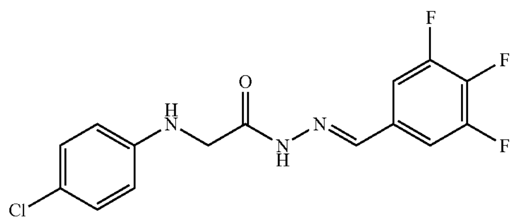 | 4-chlorophenyl | NH | CH₂ | H | F | F | F | (E)-2-(4-chlorophenylamino)-N'-(3,4,5-trifluorobenzylidene)acetohydrazide |
| 251 | 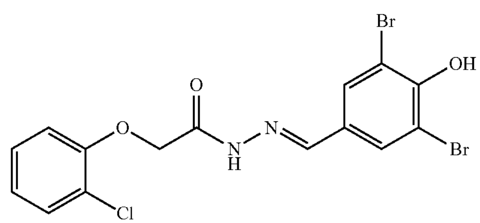 | 2-chlorophenyl | O | CH₂ | H | Br | Br | OH | (E)-2-(2-chlorophenoxy)-N'-(3,5-dibromo-4-hydroxybenzylidene)acetohydrazide |

TABLE 1-continued

III

| Comp. | Structure | R³ | Z' | alk | R | X | X¹ | Y | Name |
|---|---|---|---|---|---|---|---|---|---|
| 291 | 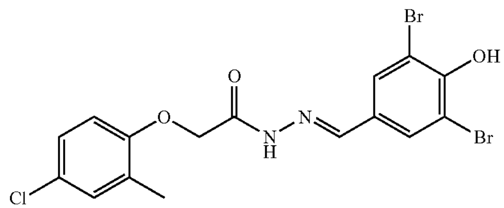 | 4-chloro-2-methylphenyl | O | CH₂ | H | Br | Br | OH | (E)-2-(4-chloro-2-methylphenoxy)-N'-(3,5-dibromo-4-hydroxybenzylidene)acetohydrazide |
| 294 | 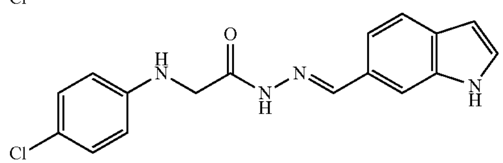 | 4-chlorophenyl | NH | CH₂ | H | H | 1H-indol-6-yl | | (E)-N'-((1H-indol-6-yl)methylene)-2-(4-chlorophenylamino)acetohydrazide |
| 301 | 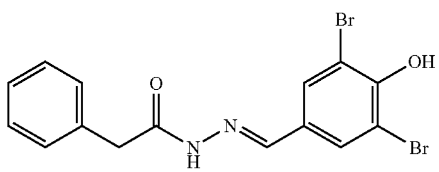 | phenyl | — | CH₂ | H | Br | Br | OH | (E)-N'-(3,5-dibromo-4-hydroxybenzylidene)-2-phenylacetohydrazide |
| 312 | 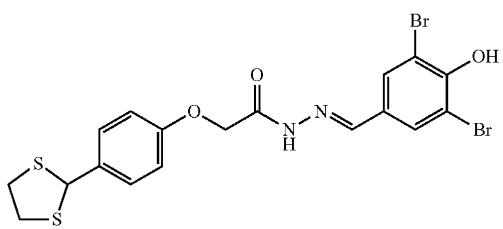 | 4-(1,3-dithiolan-2-yl)phenyl | O | CH₂ | H | Br | Br | OH | (E)-2-(4-(1,3-dithiolan-2-yl)phenoxy)-N'-(3,5-dibromo-4-hydroxybenzylidene)acetohydrazide |

TABLE 1-continued

III

R³—Z'—alk

[structure showing R³-Z'-alk-C(=O)-NH-N=C(R)-phenyl with X, Y, X¹ substituents]

| Comp. | Structure | R³ | Z' | alk | R | X | X¹ | Y | Name |
|---|---|---|---|---|---|---|---|---|---|
| 329 | [structure] | 2-chlorophenyl | NH | CH₂ | H | Br | Br | OH | (E)-2-(2-chlorophenylamino)-N'-(3,5-dibromo-4-hydroxybenzylidene)acetohydrazide |
| 343 | [structure] | 4-chlorophenyl | NH | CH₂ | H | H | Br | F | (E)-N'-(3-bromo-4-fluorobenzylidene)-2-(4-chlorophenylamino)acetohydrazide |
| 362 | [structure] | 4-chlorophenyl | NH | CH₂ | H | H | CH₃ | F | (E)-2-(4-chlorophenylamino)-N'-(4-fluoro-3-methylbenzylidene)acetohydrazide |
| 366 | [structure] | 4-chlorophenyl | NH | CH₂ | H | H | H | F | (E)-2-(4-chlorophenylamino)-N'-(4-fluorobenzylidene)acetohydrazide |

TABLE 1-continued

| Comp. | Structure | R³ | Z' | alk | R | X | X¹ | Y | Name |
|---|---|---|---|---|---|---|---|---|---|
| 430 | 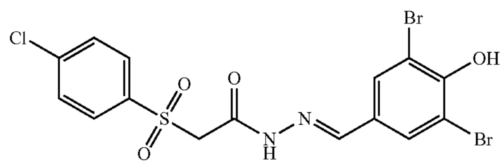 | 4-chlorophenyl | SO₂ | CH₂ | H | Br | Br | OH | (E)-2-(4-chlorophenylsulfonyl)-N'-(3,5-dibromo-4-hydroxybenzylidene)acetohydrazide |
| 431 | 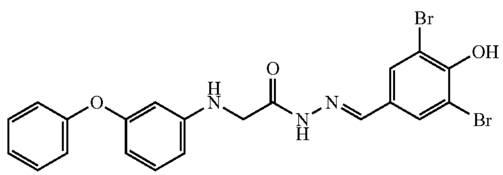 | 3-phenoxyphenyl | NH | CH₂ | H | Br | Br | OH | (E)-N'-(3,5-dibromo-4-hydroxybenzylidene)-2-(3-phenoxyphenylamino)acetohydrazide |

In a preferred embodiment, the compounds of the invention are of formula V where n is zero, one, two or three:

TABLE 2

| Comp. | Structure | R¹ | R | X | X¹ | Y | Name |
|---|---|---|---|---|---|---|---|
| 3 | 3-(4-(trifluoromethoxy)phenyl | H | H | Br | Br | OH | (E)-N'-(3,5-dibromo-4-hydroxymethoxy)-3-(4-(trifluoromethoxy)phenoxy)benzohydrazide |
| 5 | 3-(4-(trifluoromethyl)phenyl | H | H | Br | Br | OH | (E)-N'-(3,5-dibromo-4-hydroxymethyl)phenoxy)-3-(4-(trifluoromethyl)phenoxy)benzohydrazide |

TABLE 2-continued

| Comp. | Structure | R¹ | R | X | X¹ | Y | Name |
|---|---|---|---|---|---|---|---|
| 7 | 3-(4-bromophenoxy)phenyl | H | H | Br | Br | OH | (E)-3-(4-bromophenoxy)-N'-(3,5-dibromo-4-hydroxybenzylidene)benzohydrazide |
| 8 | 3-(3-methylphenoxy)phenyl | H | H | Br | Br | OH | (E)-3-(3-methylphenoxy)-N'-(3,5-dibromo-4-hydroxybenzylidene)benzohydrazide |
| 9 | 4-bromo-3-chlorophenyl | H | H | Br | Br | OH | (E)-4-bromo-3-chloro-N'-(3,5-dibromo-4-hydroxybenzylidene)benzohydrazide |

TABLE 2-continued

| Comp. | Structure | R¹ | R | X | X¹ | Y | Name |
|---|---|---|---|---|---|---|---|
| 14 | (4-fluoro-3-methoxyphenoxy)phenyl | H | H | Br | Br | OH | (E)-N'-(3,5-dibromo-4-hydroxybenzylidene)-3-(4-fluoro-3-methoxyphenoxy)benzohydrazide |
| 15 | 3-phenoxyphenyl | allyl | H | Br | Br | OH | (E)-N-allyl-N'-(3,5-dibromo-4-hydroxybenzylidene)-3-phenoxybenzohydrazide |
| 16 | 3-phenoxyphenyl | H | CH₃ | Br | Br | OH | (E)-N'-(1-(3,5-dibromo-4-hydroxyphenyl)ethylidene)-3-phenoxybenzohydrazide |

TABLE 2-continued

| Comp. | Structure | R¹ | R | X | X¹ | Y | Name |
|---|---|---|---|---|---|---|---|
| 17 | 3-phenoxyphenyl | H | H | I | I | OH | (E)-N'-(4-hydroxy-3,5-diiodobenzylidene)-3-phenoxybenzohydrazide |
| 18 | 3-(3-(trifluoromethyl)phenoxy)phenyl | H | H | Br | Br | OH | (E)-N'-(3,5-dibromo-4-hydroxybenzylidene)-3-(3-(trifluoromethyl)phenoxy)benzohydrazide |
| 19 | 3-(benzyloxy)phenyl | H | H | Br | Br | OH | (E)-3-(benzyloxy)-N'-(3,5-dibromo-4-hydroxybenzylidene)benzohydrazide |

TABLE 2-continued

| Comp. | Structure | R¹ | R | X | X¹ | Y | Name |
|---|---|---|---|---|---|---|---|
| 20 | 3-phenoxyphenyl | H | H | Br | Br | OH | (E)-N'-(3,5-dibromo-4-hydroxybenzylidene)-3-phenoxybenzohydrazide |
| 21 | 3-phenoxyphenyl | H | H | Cl | Cl | OH | (E)-N'-(3,5-dichloro-4-hydroxybenzylidene)-3-phenoxybenzohydrazide |
| 25 | 3-(3,4-dichlorophenoxy)phenyl | H | H | Br | Br | OH | (E)-N'-(3,5-dibromo-4-hydroxybenzylidene)-3-(3,4-dichlorophenoxy)benzohydrazide |

TABLE 2-continued

| Comp. | Structure | R¹ | R | X | X¹ | Y | Name |
|---|---|---|---|---|---|---|---|
| 27 | 2'-fluorobiphen-4-yl | H | H | Br | Br | OH | (E)-N'-(3,5-dibromo-4-hydroxybenzylidene)-2'-fluorobiphenyl-4-carbohydrazide |
| 31 | 3-(3-chloro-4-ethoxyphenoxy)phenyl | H | H | Br | Br | OH | (E)-3-(3-chloro-4-ethoxyphenoxy)-N'-(3,5-dibromo-4-hydroxybenzylidene)benzohydrazide |

TABLE 2-continued
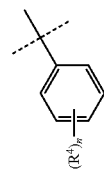
| Comp. | Structure | $R^1$ | R | X | $X^1$ | Y | Name |
|---|---|---|---|---|---|---|---|
| 32 | 3-bromo-4-chlorophenyl 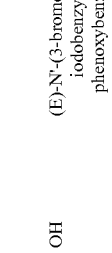 | H | H | Br | Br | OH | (E)-3-bromo-4-chloro-N'-(3,5-dibromo-4-hydroxybenzylidene)benzohydrazide |
| 35 | 3-phenoxyphenyl 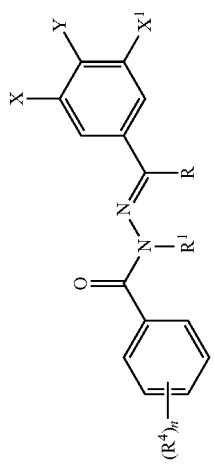 | H | H | I | Br | OH | (E)-N'-(3-bromo-4-hydroxy-5-iodobenzylidene)-3-phenoxybenzohydrazide |
| 36 | 3-(3,4,5-trifluorophenoxy)phenyl 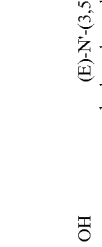 | H | H | Br | Br | OH | (E)-N'-(3,5-dibromo-4-hydroxybenzylidene)-3-(3,4,5-trifluorophenoxy)benzohydrazide |

TABLE 2-continued

| Comp. | Structure | R¹ | R | X | X¹ | Y | Name |
|---|---|---|---|---|---|---|---|
| 37 | 3-(3,5-bis(trifluoromethyl)phenoxy)phenyl | H | H | Br | Br | OH | (E)-3-(3,5-bis(trifluoromethyl)phenoxy)-N'-(3,5-dibromo-4-hydroxybenzylidene)benzohydrazide |
| 38 | 3-phenoxyphenyl | H | H | Cl | Br | OH | (E)-N'-(3-bromo-5-chloro-4-hydroxybenzylidene)-3-phenoxybenzohydrazide |

TABLE 2-continued

| Comp. | Structure | $R^1$ | R | X | $X^1$ | Y | Name |
|---|---|---|---|---|---|---|---|
| 45 | 3-(4-methoxy-3-methylphenoxy)phenyl | H | H | Br | Br | OH | (E)-N'-(3,5-dibromo-4-hydroxybenzylidene)-3-(4-methoxy-3-methylphenoxy)benzohydrazide |
| 46 | 3-benzylphenyl | H | H | Br | Br | OH | (E)-3-benzyl-N'-(3,5-dibromo-4-hydroxybenzylidene)benzohydrazide |
| 51 | 3-phenoxyphenyl | H | CH₃ | Cl | Cl | OH | (E)-N'-(1-(3,5-dichloro-4-hydroxyphenyl)ethylidene)-3-phenoxybenzohydrazide |

TABLE 2-continued

| Comp. | Structure | R¹ | R | X | X¹ | Y | Name |
|---|---|---|---|---|---|---|---|
| 53 | 3-(3-acetyl-phenoxy)phenyl | H | H | Br | Br | OH | (E)-3-(3-acetylphenoxy)-N'-(3,5-dibromo-4-hydroxybenzylidene)benzohydrazide |
| 54 | 3-(3-(trifluoromethoxy)phenoxy)phenyl | H | H | Br | Br | OH | (E)-N'-(3,5-dibromo-4-hydroxybenzylidene)-3-(3-(trifluoromethoxy)phenoxy)benzohydrazide |
| 55 | 3-(2,3-dihydrobenzo[b][1,4]dioxin-6-yloxy)phenyl | H | H | Br | Br | OH | (E)-N'-(3,5-dibromo-4-hydroxybenzylidene)-3-(2,3-dihydrobenzo[b][1,4]dioxin-6-yloxy)benzohydrazide |

TABLE 2-continued

| Comp. | Structure | R¹ | R | X | X¹ | Y | Name |
|---|---|---|---|---|---|---|---|
| 59 | 3-phenoxyphenyl | H | benzyl | Br | Br | OH | (E)-N'-(1-(3,5-dibromo-4-hydroxyphenyl)-2-phenylethylidene)-3-phenoxybenzohydrazide |
| 60 | 3-benzoylphenyl | H | H | Br | Br | OH | (E)-3-benzoyl-N'-(3,5-dibromo-4-hydroxybenzylidene)benzohydrazide |
| 61 | 3-(4-methoxyphenoxy)phenyl | H | H | Br | Br | OH | (E)-N'-(3,5-dibromo-4-hydroxybenzylidene)-3-(4-methoxyphenoxy)benzohydrazide |

TABLE 2-continued

| Comp. | Structure | R¹ | R | X | X¹ | Y | Name |
|---|---|---|---|---|---|---|---|
| 63 | ![structure] | 4-phenoxyphenyl | H | H | Br | Br | OH | (E)-N'-(3,5-dibromo-4-hydroxybenzylidene)-4-phenoxybenzohydrazide |
| 64 | ![structure] | 3-phenoxyphenyl | 4-tert-butylbenzyl | H | Br | Br | OH | (E)-N-(4-tert-butylbenzyl)-N'-(3,5-dibromo-4-hydroxybenzylidene)-3-phenoxybenzohydrazide |

TABLE 2-continued

| Comp. | Structure | R¹ | R | X | X¹ | Y | Name |
|---|---|---|---|---|---|---|---|
| 70 | 3-phenoxyphenyl | H | H | F | F | OH | (E)-N'-(3,5-difluoro-4-hydroxybenzylidene)-3-phenoxybenzohydrazide |
| 71 | 3,5-dichlorophenyl | H | H | Br | Br | OH | (E)-3,5-dichloro-N'-(3,5-dibromo-4-hydroxybenzylidene)benzohydrazide |
| 73 | 3-phenoxyphenyl | CH₃ | H | Br | Br | OH | (E)-N'-(3,5-dibromo-4-hydroxybenzylidene)-N-methyl-3-phenoxybenzohydrazide |

TABLE 2-continued

| Comp. | Structure | R¹ | R | X | X¹ | Y | Name |
|---|---|---|---|---|---|---|---|
| 74 | | H | 3-(3-(benzyl-oxy)phenoxy)phenyl | H | Br | Br | OH | (E)-3-(3-(benzyloxy)phenoxy)-N'-(3,5-dibromo-4-hydroxybenzylidene)benzohydrazide |
| 75 | | H | 3-(3-(methylsulfona-midophenoxy)phenyl | H | Br | Br | OH | (E)-N-(3-(2-(3,5-dibromo-4-hydroxybenzylidene)hydrazinecarbonyl)phenoxy)phenyl)methanesulfonamide |
| 78 | 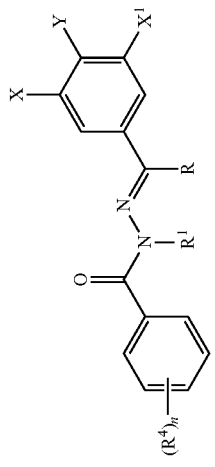 | H | 3-hydroxy-naphth-2-yl | H | Br | Br | OH | (E)-N'-(3,5-dibromo-4-hydroxybenzylidene)-3-hydroxy-2-naphthohydrazide |

TABLE 2-continued

| Comp. | Structure | R¹ | R | X | X¹ | Y | Name |
|---|---|---|---|---|---|---|---|
| 103 | | 3-(3-(trifluoromethyl)benzamido)phenyl | H | H | Br | Br | OH | (E)-N-(3-(2-(3,5-dibromo-4-hydroxybenzylidene)hydrazinecarbonyl)phenyl)-3-(trifluoromethyl)benzamide |
| 112 | | 4-(benzyloxy)phenyl | H | H | Br | Br | OH | (E)-4-(benzyloxy)-N'-(3,5-dibromo-4-hydroxybenzylidene)benzohydrazide |
| 160 | | 3-(o-tolyloxy)phenyl | H | H | Br | Br | OH | (E)-N'-(3,5-dibromo-4-hydroxybenzylidene)-3-(o-tolyloxy)benzohydrazide |

TABLE 2-continued

| Comp. | Structure | (R⁴)ₙ | R¹ | R | X | X¹ | Y | Name |
|---|---|---|---|---|---|---|---|---|
| 163 | 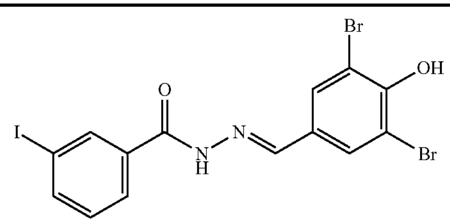 | 3-iodophenyl | H | H | Br | Br | OH | (E)-N'-(3,5-dibromo-4-hydroxybenzylidene)-3-iodobenzohydrazide |
| 164 | 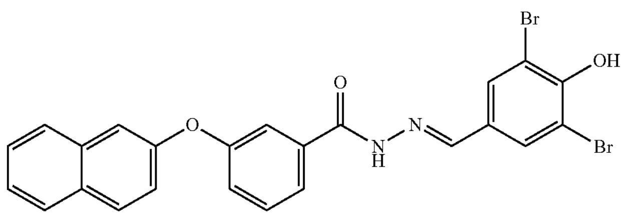 | 3-(naphthalen-2-yloxy)phenyl | H | H | Br | Br | OH | (E)-N'-(3,5-dibromo-4-hydroxybenzylidene)-3-(naphthalen-2-yloxy)benzohydrazide |
| 165 | 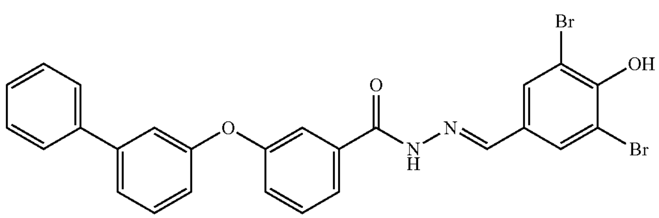 | 3-(biphenyl-3-yloxy)phenyl | H | H | Br | Br | OH | (E)-3-(biphenyl-3-yloxy)-N'-(3,5-dibromo-4-hydroxybenzylidene)benzohydrazide |

TABLE 2-continued

| Comp. | Structure | R¹ | R | X | X¹ | Y | Name |
|---|---|---|---|---|---|---|---|
| 168 | 3-(3-(methoxymethyl)phenoxy)phenyl | H | H | Br | Br | OH | (E)-N'-(3,5-dibromo-4-hydroxybenzylidene)-3-(3-methoxymethyl)phenoxy)benzohydrazide |
| 169 | 4-tert-butylphenyl | H | H | Br | Br | OH | (E)-4-tert-butyl-N'-(3,5-dibromo-4-hydroxybenzylidene)benzohydrazide |
| 170 | 3-(4-isopropoxyphenoxy)phenyl | H | H | Br | Br | OH | (E)-N'-(3,5-dibromo-4-hydroxybenzylidene)-3-(4-isopropoxyphenoxy)benzohydrazide |

TABLE 2-continued

| Comp. | Structure | $R^1$ | R | X | $X^1$ | Y | Name |
|---|---|---|---|---|---|---|---|
| 174 | | 2,5-bis(2,2,2-trifluoroethoxy)phenyl | H | H | Br | Br | OH | (E)-N'-(3,5-dibromo-4-hydroxybenzylidene)-2,5-bis(2,2,2-trifluoromethoxy)benzohydrazide |
| 175 | | 2-phenoxyphenyl | H | H | Br | Br | OH | (E)-N'-(3,5-dibromo-4-hydroxybenzylidene)-2-phenoxybenzohydrazide |

TABLE 2-continued

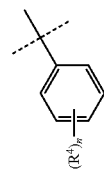

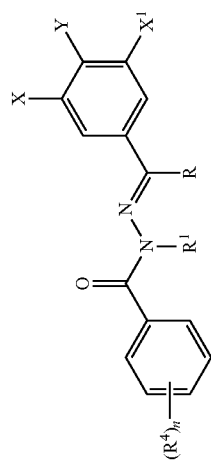

| Comp. | Structure | R¹ | R | X | X¹ | Y | Name |
|---|---|---|---|---|---|---|---|
| 178 | 3-(3,4-dichloro-phenylsulfona-mido)phenyl | H | H | Br | Br | OH | (E)-3,4-dichloro-N-(3-(2-(3,5-dibromo-4-hydroxybenzylidene)hydrazine-carbonyl)phenyl)benzenesulfonamide |
| 182 | 4-bromo-2-chlorophenyl | H | H | Br | Br | OH | (E)-4-bromo-2-chloro-N'-(3,5-dibromo-4-hydroxybenzylidene)benzohydrazide |
| 183 | 4-(trifluoro-methoxy)phenyl | H | H | Br | Br | OH | (E)-N'-(3,5-dibromo-4-hydroxybenzylidene)-4-(trifluoromethoxy)benzohydrazide |

TABLE 2-continued

| Comp. | Structure | R¹ | R | X | X¹ | Y | Name |
|---|---|---|---|---|---|---|---|
| | | 2-naphthyl | H | H | Br | Br | OH | (E)-N'-(3,5-dibromo-4-hydroxybenzylidene)-2-naphthohydrazide |
| 187 | 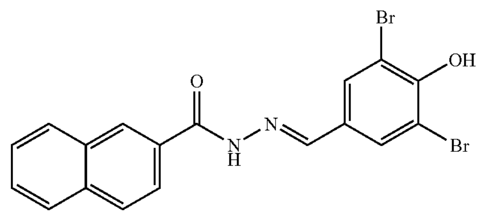 | | | | | | |
| | | 3-(naphthalene-2-sulfonamidophenyl) | H | H | OH | H | OH | (E)-N-(3-(2-(3,4-dihydroxybenzylidene)hydrazine-carbonyl)phenyl)naphthalene-2-sulfonamide |
| 188 | 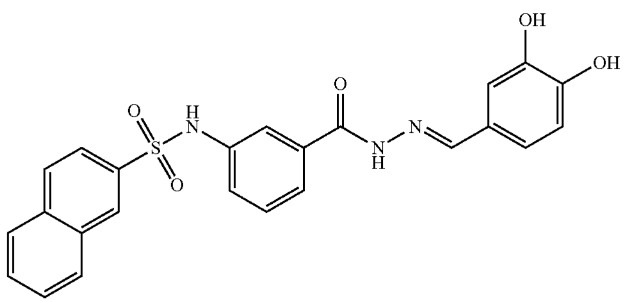 | | | | | | |

TABLE 2-continued
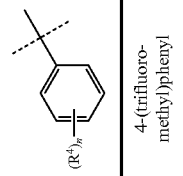
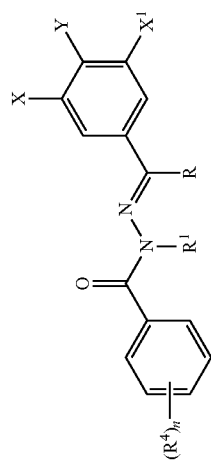
| Comp. | Structure | R[1] | R | X | X[1] | Y | Name |
|---|---|---|---|---|---|---|---|
| 189 | 4-(trifluoro-methyl)phenyl | H | H | Br | Br | OH | (E)-N'-(3,5-dibromo-4-hydroxybenzylidene)-4-(trifluoromethyl)benzohydrazide |
| 190 | 3-bromophenyl | H | H | Br | Br | OH | (E)-3-bromo-N'-(3,5-dibromo-4-hydroxybenzylidene)benzohydrazide |
| 191 | 3-(4-(pyrrolidine-1-carbonyl)phenoxy)phenyl | H | H | Br | Br | OH | (E)-N'-(3,5-dibromo-4-hydroxybenzylidene)-3-(4-pyrrolidine-1-carbonyl)phenoxy)benzohydrazide |

TABLE 2-continued

| Comp. | Structure | (R⁴)ₙ | R¹ | R | X | X¹ | Y | Name |
|---|---|---|---|---|---|---|---|---|
| 193 | 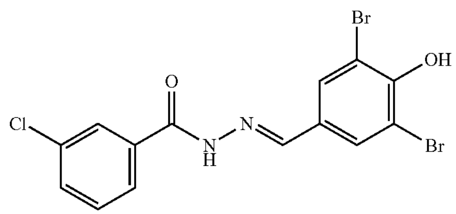 | 3-chlorophenyl | H | H | Br | Br | OH | (E)-3-chloro-N'-(3,5-dibromo-4-hydroxybenzylidene)benzohydrazide |
| 196 | 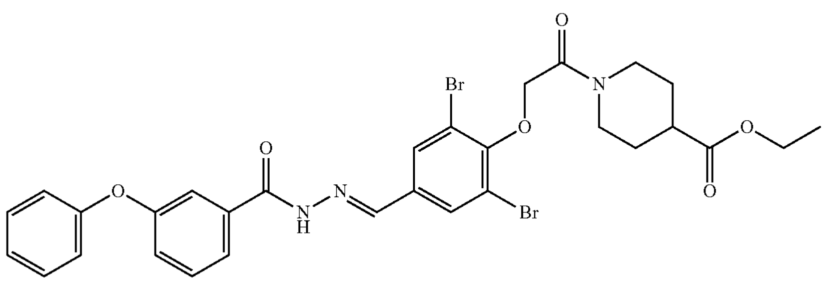 | 3-phenoxyphenyl | H | H | Br | Br | (((4-ethoxy-carbonyl-piperidin-1-yl)carbonyl)methoxy | (E)-ethyl 1-(2-(2,6-dibromo-4-((2-(3-phenoxybenzoyl)hydrazono)methyl)phenoxy)acetyl)piperidine-4-carboxylate |
| 200 | 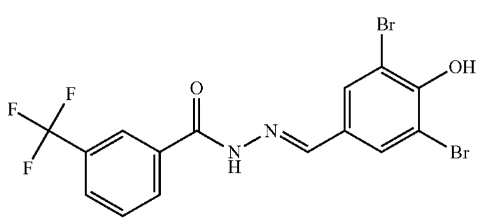 | 3-(trifluoromethyl)phenyl | H | H | Br | Br | OH | (E)-N'-(3,5-dibromo-4-hydroxybenzylidene)-3-(trifluoromethyl)benzohydrazide |

TABLE 2-continued

| Comp. | Structure | R¹ | R | X | X¹ | Y | Name |
|---|---|---|---|---|---|---|---|
| 202 | 3-(benzenesulfonamido)phenyl | H | H | Br | Br | OH | (E)-N-(3-(2-(3,5-dibromo-4-hydroxybenzylidene)hydrazinecarbonyl)phenyl)benzenesulfonamide |
| 204 | 4-(2,5-dimethyl-1H-pyrrol-1-yl)phenyl | H | H | Br | Br | OH | (E)-N'-(3,5-dibromo-4-hydroxybenzylidene)-4-(2,5-dimethyl-1H-pyrrol-1-yl)benzohydrazide |

TABLE 2-continued

| Comp. | Structure | R¹ | R | X | X¹ | Y | Name |
|---|---|---|---|---|---|---|---|
| 205 | 3-phenoxyphenyl | H | H | Br | Br | (2-hydroxy-2-oxo)ethoxy | (E)-2-(2,6-dibromo-4-((2-(3-phenoxybenzoyl)hydrazono)methyl)phenoxy)acetic acid |
| 210 | 3-(4-(hydroxymethyl)phenoxy)phenyl | H | H | Br | Br | OH | (E)-N'-(3,5-dibromo-4-hydroxybenzylidene)-3-(4-(hydroxymethyl)phenoxy)benzohydrazide |
| 212 | 4-chlorophenyl | H | H | Br | Br | OH | (E)-4-chloro-N'-(3,5-dibromo-4-hydroxybenzylidene)benzohydrazide |

TABLE 2-continued

| Comp. | Structure | R¹ | R | X | X¹ | Y | Name |
|---|---|---|---|---|---|---|---|
| 219 | 3,5-bis(trifluoromethyl)phenyl | H | H | Br | Br | OH | (E)-N'-(3,5-dibromo-4-hydroxybenzylidene)-3,5-bis(trifluoromethyl)benzohydrazide |
| 299 | biphen-4-yl | H | H | Br | Br | OH | (E)-N'-(3,5-dibromo-4-hydroxybenzylidene)biphenyl-4-carbohydrazide |

In a preferred embodiment, the compounds of the invention are of formula VI where n is zero, one, two or three and A is heteroaryl or substituted heteroaryl:

TABLE 3

| Comp. | Structure | | | X | X¹ | X² | Name |
|---|---|---|---|---|---|---|---|
| | (structure VI with X, X¹, X² on hydroxyphenyl, A ring with (R⁵)ₙ) | 2-p-tolylquinolin-4-yl | | Br | Br | H | (E)-N'-(3,5-dibromo-4-hydroxybenzylidene)-2-p-tolylquinoline-4-carbohydrazide |
| 24 | (3,5-dibromo-4-hydroxybenzylidene hydrazide of 2-p-tolylquinoline-4-carboxylic acid) | | | | | | |
| 26 | (3,5-dibromo-4-hydroxybenzylidene hydrazide of 2-(4-bromophenyl)quinoline-4-carboxylic acid) | 2-(4-bromophenyl)quinolin-4-yl | | Br | Br | H | (E)-2-(4-bromophenyl)-N'-(3,5-dibromo-4-hydroxybenzylidene)quinoline-4-carbohydrazide |

TABLE 3-continued

| Comp. | Structure | A | X | X¹ | X² | Name |
|---|---|---|---|---|---|---|
| 28 | ![structure] | 2-(4-ethoxyphenyl)quinolin-4-yl | Br | Br | H | (E)-N'-(3,5-dibromo-4-hydroxybenzylidene)-2-(4-ethoxyphenyl)quinoline-4-carbohydrazide |
| 39 | ![structure] | 8-chloro-2-phenylquinolin-4-yl | Br | Br | H | (E)-8-chloro-N'-(3,5-dibromo-4-hydroxybenzylidene)-2-phenylquinoline-4-carbohydrazide |

TABLE 3-continued

| Comp. | Structure | | X | X¹ | X² | Name |
|---|---|---|---|---|---|---|
| 41 | 2-(4-chlorophenyl)quinolin-4-yl | | Cl | Cl | H | (E)-2-(4-chlorophenyl)-N'-(3,5-dichloro-4-hydroxybenzylidene)quinoline-4-carbohydrazide |
| 42 | 2-(4-chlorophenyl)quinolin-4-yl | | Br | Br | H | (E)-2-(4-chlorophenyl)-N'-(3,5-dibromo-4-hydroxybenzylidene)quinoline-4-carbohydrazide |

TABLE 3-continued

VI: [structure: 4-hydroxy-phenyl with X, X¹, X² substituents, connected via CH=N-NH-C(=O)- to ring A bearing (R⁵)ₙ]

| Comp. | Structure | X | X¹ | X² | A | Name |
|---|---|---|---|---|---|---|
| 44 | [structure shown] | Br | Br | H | 2-(4-methoxyphenyl)quinolin-4-yl | (E)-N'-(3,5-dibromo-4-hydroxybenzylidene)-2-(4-methoxyphenyl)quinoline-4-carbohydrazide |
| 49 | [structure shown] | Br | Br | H | 2-(thiophen-2-yl)quinolin-4-yl | (E)-N'-(3,5-bromo-4-hydroxybenzylidene)-2-(thiophen-2-yl)quinoline-4-carbohydrazide |

TABLE 3-continued

| Comp. | Structure | X | X¹ | X² | A | Name |
|---|---|---|---|---|---|---|
| 52 | 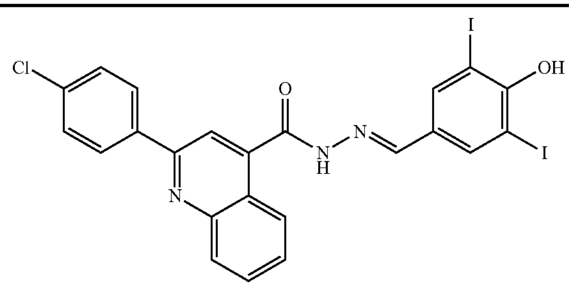 | I | I | H | (4-chlorophenyl)quinolin-4-yl) | (E)-2-(4-chlorophenyl)-N'-(4-hydroxy-3,5-diiodobenzylidene)quinoline-4-carbohydrazide |
| 62 | 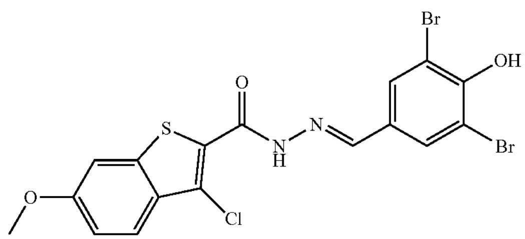 | Br | Br | H | 3-chloro-6-methoxybenzo[b]thioph-2-yl | (E)-3-chloro-N'-(3,5-dibromo-4-hydroxybenzylidene)-6-methoxybenzo[b]thiophene-2-carbohydrazide |
| 68 | 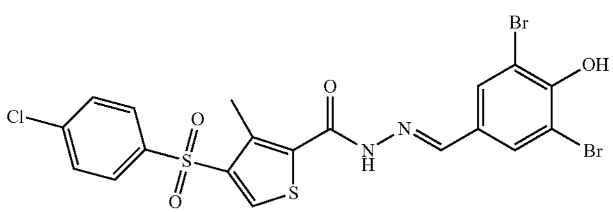 | Br | Br | H | 4-(4-chlorophenylsulfonyl)-3-methylthioph-2-yl | (E)-4-(4-chlorophenylsulfonyl)-N'-(3,5-dibromo-4-hydroxybenzylidene)-3-methylthiophene-2-carbohydrazide |

TABLE 3-continued

VI

| Comp. | Structure | A | X | X¹ | X² | Name |
|---|---|---|---|---|---|---|
| 76 | (structure) | 2-(4-chlorophenyl)pyridin-4-yl | Br | Br | H | (E)-2-(4-chlorophenyl)-N'-(3,5-dibromo-4-hydroxybenzylidene)isonicotinohydrazide |
| 159 | (structure) | 3-chlorobenzo[b]thiophen-2-yl | Br | Br | H | (E)-3-chloro-N'-(3,5-dibromo-4-hydroxybenzylidene)benzo[b]thiophene-2-carbohydrazide |
| 161 | (structure) | 3-tert-butyl-1-(2,4-dichlorobenzyl)-1H-pyrazol-5-yl | Br | Br | H | (E)-3-tert-butyl-N'-(3,5-dibromo-4-hydroxybenzylidene)-1-(2,4-dichlorobenzyl)-1H-pyrazole-5-carbohydrazide |

TABLE 3-continued

| Comp. | Structure | A | X | X¹ | X² | Name |
|---|---|---|---|---|---|---|
| 162 | [structure] | 2-(4-chloro-phenyl)quinolin-4-yl | Br | Br | OH | (E)-2-(4-chlorophenyl)-N'-(3,5-dibromo-2,4-dihydroxybenzylidene)quinoline-4-carbohydrazide |
| 166 | [structure] | 2-(5-chlorothiophen-2-yl)quinolin-4-yl | Br | Br | H | (E)-2-(5-chlorothiophen-2-yl)-N'-(3,5-dibromo-4-hydroxybenzylidene)quinoline-4-carbohydrazide |

TABLE 3-continued

VI

![Structure with OH, X, X1, X2 on benzene, =N-NH-C(O)-A-(R5)n]

| Comp. | Structure | A (R5)n | X | X1 | X2 | Name |
|---|---|---|---|---|---|---|
| 167 | ![structure] | 5-(hex-1-ynyl)pyridin-3-yl | Br | Br | H | (E)-N'-(3,5-dibromo-4-hydroxybenzylidene)-5-(hex-1-ynyl)nicotinohydrazide |
| 172 | ![structure] | 3-tert-butyl-1-(4-fluorobenzyl)-1H-pyrazol-5-yl | Br | Br | H | (E)-3-tert-butyl-N'-(3,5-dibromo-4-hydroxybenzylidene)-1-(4-fluorobenzyl)-1H-pyrazole-5-carbohydrazide |

TABLE 3-continued

| Comp. | Structure | | | X | X¹ | X² | Name |
|---|---|---|---|---|---|---|---|
| 186 | [structure with 3,4-dihydroxybenzylidene hydrazide and 3-(4-fluorobenzyloxy)thiophene] | 3-(4-fluorobenzyl-oxy)thiophen-2-yl | | H | OH | H | (E)-N'-(3,4-dihydroxybenzylidene)-3-(4-fluorobenzyloxy)thiophene-2-carbohydrazide |
| 192 | [structure with 3,5-dibromo-4-hydroxybenzylidene hydrazide and indole] | 1H-indol-2-yl | | Br | Br | H | (E)-N'-(3,5-bromo-4-hydroxybenzylidene)-1H-indole-2-carbohydrazide |

TABLE 3-continued

VI

[Structure diagram: X-substituted 4-hydroxyphenyl with X¹, X² substituents connected via CH=N-NH-C(=O) linker to ring A bearing (R⁵)ₙ substituents]

| Comp. | Structure | X | X¹ | X² | A | Name |
|---|---|---|---|---|---|---|
| 195 | [structure] | Br | Br | H | 3-chloro-6-methyl-benzo[b]thiophen-2-yl | (E)-3-chloro-N'-(3,5-dibromo-4-hydroxybenzylidene)-6-methylbenzo[b]thiophene-2-carbohydrazide |
| 198 | [structure] | Br | Br | H | 5-methyl-1-(4-methylphenyl)-1H-pyrazol-4-yl | (E)-N'-(3,5-dibromo-4-hydroxybenzylidene)-5-methyl-1-(4-methylphenyl)-1H-pyrazole-4-carbohydrazide |
| 199 | [structure] | Br | Br | H | 4-methyl-2-phenylpyrimidin-5-yl | (E)-N'-(3,5-dibromo-4-hydroxybenzylidene)-4-methyl-2-phenylpyrimidine-5-carbohydrazide |

TABLE 3-continued

| Comp. | Structure | X | $X^1$ | $X^2$ | A | Name |
|---|---|---|---|---|---|---|
| 207 | 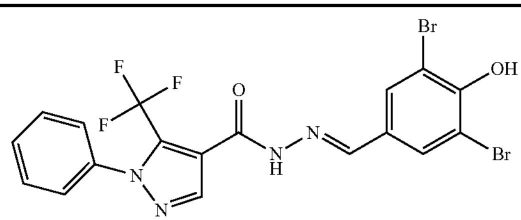 | Br | Br | H | 1-phenyl-5-(trifluoromethyl)-1H-pyrazol-4-yl | (E)-N'-(3,5-dibromo-4-hydroxybenzylidene)-1-phenyl-5-(trifluoromethyl)-1H-pyrazole-4-carbohydrazide |
| 208 | 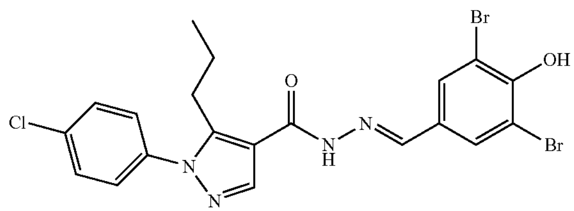 | Br | Br | H | 1-(4-chlorophenyl)-5-n-propyl-1H-pyrazol-4-yl | (E)-1-(4-chlorophenyl)-N'-(3,5-dibromo-4-hydroxybenzylidene)-5-propyl-1H-pyrazole-4-carbohydrazide |
| 211 | 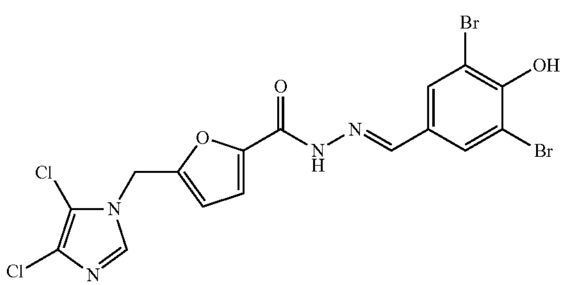 | Br | Br | H | 5-((4,5-dichloro-1H-imidazol-1-yl)methyl)furan-2-yl | (E)-N'-(3,5-dibromo-4-hydroxybenzylidene)-5-((4,5-dichloro-1H-imidazol-1-yl)methyl)furan-2-carbohydrazide |

TABLE 3-continued

| Comp. | Structure | X | X¹ | X² | A | Name |
|---|---|---|---|---|---|---|
| 217 | 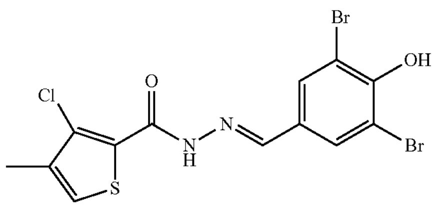 | Br | Br | H | 3-chloro-4-methylthiophen-2-yl | (E)-3-chloro-N'-(3,5-dibromo-4-hydroxybenzylidene)-4-methylthiophene-2-carbohydrazide |
| 238 | 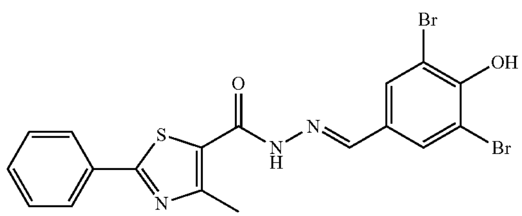 | Br | Br | H | 4-methyl-2-phenylthiazol-5-yl | (E)-N'-(3,5-dibromo-4-hydroxybenzylidene)-4-methyl-2-phenylthiazole-5-carbohydrazide |
| 240 | 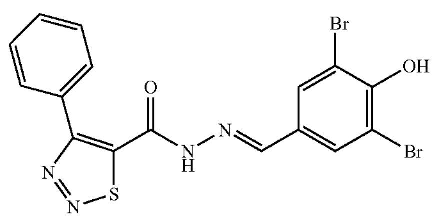 | Br | Br | H | 4-phenyl-1,2,3-thiadiazol-5-yl | (E)-N'-(3,5-dibromo-4-hydroxybenzylidene)-4-phenyl-1,2,3-thiadiazole-5-carbohydrazide |

TABLE 3-continued

| Comp. | Structure | X | X¹ | X² | Name |
|---|---|---|---|---|---|
| 245 | 2-phenylthiazol-4-yl | Br | Br | H | (E)-N'-(3,5-dibromo-4-hydroxybenzylidene)-2-phenylthiazole-4-carbohydrazide |
| 256 | 2-(2,3-dichlorophenyl)thiazol-4-yl | Br | Br | H | (E)-N'-(3,5-dibromo-4-hydroxybenzylidene)-2-(2,3-dichlorophenyl)thiazole-4-carbohydrazide |
| 317 | benzo[b]thiophen-2-yl | Br | Br | H | (E)-N'-(3,5-dibromo-4-hydroxybenzylidene)benzo[b]thiophene-2-carbohydrazide |

TABLE 3-continued

| Comp. | Structure | X | X¹ | X² | A | Name |
|---|---|---|---|---|---|---|
| 344 | 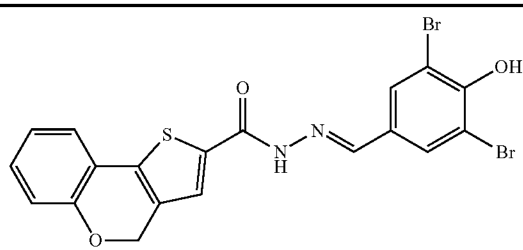 | Br | Br | H | 4H-thieno[3,2-c]chromen-2-yl | (E)-N'-(3,5-dibromo-4-hydroxybenzylidene)-4H-thieno[3,2-c]chromene-2-carbohydrazide |
| 393 | 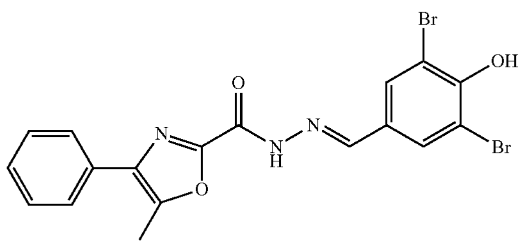 | Br | Br | H | 5-methyl-4-phenyloxazol-2-yl | (E)-N'-(3,5-dibromo-4-hydroxybenzylidene)-5-methyl-4-phenyloxazole-2-carbohydrazide |

In a preferred embodiment, the compounds of the invention are of formula II:

TABLE 4

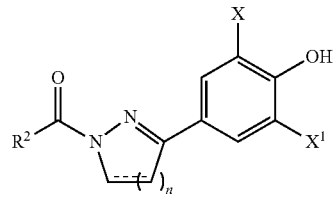

II

| Comp. | Structure | R² | n | X | X¹ | Name |
|---|---|---|---|---|---|---|
| 58 | 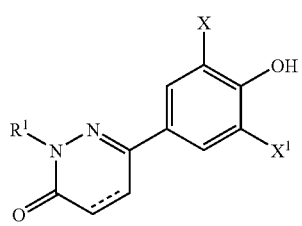 | 3-bromo-4-chlorophenyl | 1 | Br | Br | (3-bromo-4-chlorophenyl)(3-(3,5-dibromo-4-hydroxyphenyl)-4,5-dihydro-1H-pyrazol-1-yl)methanone |

In a preferred embodiment, the compounds of the invention are of formula III:

TABLE 5

III

| Comp. | Structure | R¹ | X | X¹ | Name |
|---|---|---|---|---|---|
| 72 | 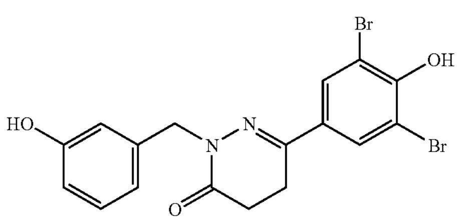 | (3-hydroxyphenyl)methyl | Br | Br | 6-(3,5-dibromo-4-hydroxyphenyl)-2-(3-hydroxybenzyl)-4,5-dihydropyridazin-3(2H)-one |

In a preferred embodiment, the compounds of the invention are of formula I, wherein $R^1$ and $R^2$ together with the atoms bound thereto, form a heterocycle or substituted heterocycle:

TABLE 6

| Comp. | Structure | $R^1$ | X | $X^1$ | $X^2$ | Y | Compound Name |
|---|---|---|---|---|---|---|---|
| 126 | [structure: 2-benzyl-3-((3,5-dibromo-4-hydroxybenzylidene)amino)quinazolin-4(3H)-one] | 2-ethylquinazolin-4(3H)-one | Br | Br | H | OH | (E)-3-(3,5-dibromo-4-hydroxybenzylidene-amino)-2-ethylquinazolin-4(3H)-one |
| 179 | [structure: 2-isopropyl-3-((3,5-dibromo-4-hydroxybenzylidene)amino)quinazolin-4(3H)-one] | 2-isopropylquinazolin-4(3H)-one | Br | Br | H | OH | (E)-3-(3,5-dibromo-4-hydroxybenzylidene-amino)-2-isopropylquinazolin-4(3H)-one |

C. Methods of the Invention

The compounds disclosed herein are useful in the treatment of a condition, disorder or disease or symptom of such condition, disorder, or disease, where the condition, disorder or disease is responsive to inhibition of functional CFTR. Such diseases or conditions include, but are not limited to the various forms of diarrhea, PKD and male infertility. The methods include administration of an effective amount of a compound defined herein (including those compounds set forth in Tables 1-6 or encompassed by formulas I-VI) or compositions thereof, thereby treating the disease. In one aspect, the compounds of the invention treat these diseases by inhibiting ion transport, e.g. $HCO_3^-$ or halide ion, e.g., chloride ion, transport by CFTR.

In one aspect, the compounds and compositions are administered or delivered to treat diarrhea and associated symptoms in an animal in need of such treatment. The term "animal" is used broadly to include mammals such as a human patient or other farm animals in need of such treatment. In one aspect, the animal is an infant (i.e., less than 2 years old, or alternatively, less than one year old, or alternatively, less than 6 months old, or alternatively, less than 3 months old, or alternatively, less than 2 months old, or alternatively, less than 1 one month old, or alternatively, less 2 weeks old), a newborn (e.g., less than one week old, or alternatively, less than one day old), a pediatric patient (e.g., less than 18 years old or alternatively less than 16 years old) or yet further, a geriatric patient (e.g., greater than 65 years old).

Since CFTR function has been associated with a wide spectrum of diseases (including secretory diarrhea, polycystic kidney disease, male infertility, chronic obstructive pulmonary disorders, pancreatic insufficiency, bacterial pulmonary conditions, and an abnormally concentrated sudoriparous secretion), administration of an effective amount of a compound of this invention will treat the disease when administered to an animal such as a human patient in need thereof. Accordingly, in one aspect the invention relates to a method of treating a disease in an animal, where the disease is responsive to inhibition of functional CFTR and is selected from the group consisting of secretory diarrhea, polycystic kidney disease (PKD), cardiac arrhythmia and disorders associated with neovascularization, by administering an effective amount of a compound defined herein (including those compounds set forth in Tables 1-6 or encompassed by formulas I-VI) or compositions thereof, thereby treating the disease. Additional examples of diseases responsive to inhibiting of functional CFTR polypeptide that can be treated by the compounds of the invention include, but are not limited to, chronic idiopathic pancreatitis, sinusitis, allergic bronchopulmonary aspergillosis (ABPA), asthma, primary sclerosing cholangitis, congenital bilateral absence of the vas deferens (CBAVD), hydrosalpinx, liver disease, bile duct injury, and mucoviscidosis.

In one aspect, the compounds of the invention are used in the treatment of the conditions associated with aberrantly increased intestinal secretion, particularly acute aberrantly increased intestinal secretion. Such intestinal secretion can result in intestinal inflammatory disorders and diarrhea, particularly secretory diarrhea. In another aspect, the invention relates to a treatment of diarrhea by administering an effective amount of the compound defined herein (including those compounds set forth in Tables 1-6 or encompassed by formulas I-VI) or compositions thereof. In a further embodiment, the invention relates to treatment of secretary diarrhea by administering an effective amount of the compound defined herein (including those compounds set forth in Tables 1-6 or encompassed by formulas I-VI) or compositions thereof. In a yet further aspect, the invention relates to the treatment of diarrhea by administering an effective amount of the compound defined herein (including those compounds set forth in Tables 1-6 or encompassed by formulas I-VI) or compositions thereof, where the diarrhea is for example, infectious diarrhea, inflammatory diarrhea or diarrhea associated with chemotherapy. In one embodiment, the invention relates to a treatment of secretary diarrhea which involves use of compounds of the invention to inhibit the CFTR chloride channel.

As used herein, "diarrhea" intends a medical syndrome which is characterized by the primary symptom of diarrhea (or scours in animals) and secondary clinical symptoms that may result from a secretory imbalance and without regard to the underlying cause and therefore includes exudative (inflammatory), decreased absorption (osmotic, anatomic derangement, and motility disorders) and secretory. As noted previously, all forms of diarrhea have a secretory component. Symptoms include, but are not limited to impaired colonic absorption, ulcerative colitis, shigellosis, and amebiasis. Osmotic diarrhea can occur as a result of digestive abnormalities such as lactose intolerance. Anatomic derangement results in a decreased absorption surface caused by such procedures as subtotal colectomy and gastrocolic fistula. Motility disorders result from decreased contact time resulting from such diseases as hyperthyroidism and irritable bowel syndrome. Secretory diarrhea is characterized by the hypersecretion of fluid and electrolytes from the cells of the intestinal wall. In classical form, the hypersecretion is due to changes which are independent of the permeability, absorptive capacity and exogenously generated osmotic gradients within the intestine. However, all forms of diarrhea can manifest a secretory component.

The compounds and compositions of this invention can also treat PKD and associated diseases or disorders such as Autosomal Dominant Polycystic Kidney Disease (ADPKD), Autosomal Recessive Polycystic Kidney Disease and Acquired Cystic Kidney Disease. The major manifestation of PKD is the progressive cystic dilation of renal tubules which ultimately leads to renal failure in half of affected individuals. U.S. Pat. No. 5,891,628 and Gabow, P. A. (1990) Am. J. Kidney Dis. 16:403-413. PKD-associated renal cysts may enlarge to contain several liters of fluid and the kidneys usually enlarge progressively causing pain. Other abnormalities such as hematuria, renal and urinary infection, renal tumors, salt and water imbalance and hypertension frequently result from the renal defect. Cystic abnormalities in other organs, including the liver, pancreas, spleen and ovaries are commonly found in PKD. Massive liver enlargement occasionally causes portal hypertension and hepatic failure. Cardiac valve abnormalities and an increased frequency of subarachnoid and other intracranial hemorrhage have also been observed in PKD. U.S. Pat. No. 5,891,628. Biochemical abnormalities which have been observed have involved protein sorting, the distribution of cell membrane markers within renal epithelial cells, extracellular matrix, ion transport, epithelial cell turnover, and epithelial cell proliferation. The most carefully documented of these findings are abnormalities in the composition of tubular epithelial cells, and a reversal of the normal polarized distribution of cell membrane proteins, such as the $Na^+/K^+$ ATPase. Carone, F. A. et al. (1994) Lab. Inv. 70:437-448.

Diarrhea amenable to treatment using the compounds of the invention can result from exposure to a variety of pathogens or agents including, without limitation, cholera toxin (*Vibrio cholera*), *E. coli* (particularly enterotoxigenic (ETEC)), *Salmonella*, e.g. Cryptosporidiosis, diarrheal viruses (e.g., rotavirus)), food poisoning, or toxin exposure that results in increased intestinal secretion mediated by CFTR.

Other diarrheas that can be treated by the compounds of the invention include diarrhea associated with AIDS (e.g., AIDS-related diarrhea), diarrheas caused by anti-AIDS medications such as protease inhibitors, inflammatory gastrointestinal disorders, such as ulcerative colitis, inflammatory bowel disease (IBD), Crohn's disease, chemotherapy, and the like. It has been reported that intestinal inflammation modulates the expression of three major mediators of intestinal salt transport and may contribute to diarrhea in ulcerative colitis both by increasing transepithelial Cl⁻ secretion and by inhibiting the epithelial NaCl absorption. See, e.g., Lohi et al. (2002) Am. J. Physiol. Gastrointest. Liver Physiol 283(3):G567-75).

The compounds and compositions can be administered alone or combined with other suitable therapy such as Oral Rehydration Therapy (ORT), supportive renal therapy, administration of an antiviral, vaccine, or other compound to treat the underlying infection or by administering an effective amount of an oral glucose-electrolyte solution to the animal. In another aspect, the compounds or compositions are co-administered with micronutrients, e.g., zinc, iron, and vitamin A. The therapies may be administered simultaneously or concurrently. Administration is by any appropriate route and varies with the disease or disorder to be treated and the age and general health of the animal or human patient.

The compounds of the invention can be administered on a mucosal surface of the gastrointestinal tract (e.g., by an enteral route, such as oral, intraintestinal, intraluminally, rectal as a suppository, and the like) or to a mucosal surface of the oral or nasal cavities (e.g., intranasal, buccal, sublingual, and the like). In one embodiment, the compounds disclosed herein are administered in a pharmaceutical formulation suitable for oral administration, intraluminally or intraperitoneal administration. In another embodiment, the compounds disclosed herein are administered in a pharmaceutical formulation suitable for sustained release.

The compounds of the invention can also find further use as male infertility drugs, by inhibition of CFTR activity in the testes.

In one aspect, the compound is administered in a sustained release formulation which comprises the compound and an effective amount of a pharmaceutically-acceptable polymer.

Such sustained release formulations provide a composition having a modified pharmacokinetic profile that is suitable for treatment as described herein. In one aspect of the invention, the sustained release formulation provides decreased $C_{max}$ and increased $T_{max}$ without altering bioavailability of the drug.

In one aspect, the compound is admixed with about 0.2% to about 5.0% w/v solution of a pharmaceutically-acceptable polymer. In other embodiments, the amount of pharmaceutically-acceptable polymer is between about 0.25% and about 5.0%; between about 1% and about 4.5%; between about 2.0% and about 4.0%; between about 2.5% and about 3.5%; or alternatively about 0.2%; about 0.25%; about 0.3%; about 0.35%; about 0.4%; about 0.45%; about 0.5%, about 1.0%, about 2.0%, about 3.0%, or about 4.0%, of the polymer.

The therapeutic and prophylactic methods of this invention are useful to treat human patients in need of such treatment. However, the methods are not to be limited only to human patient but rather can be practiced and are intended to treat any animal in need thereof. Such animals will include, but not be limited to farm animals and pets such as cows, pigs and horses, sheep, goats, cats and dogs. Diarrhea, also known as scours, is a major cause of death in these animals.

Diarrhea in animals can result from any major transition, such as weaning or physical movement. Just as with human patients, one form of diarrhea is the result of a bacterial or viral infection and generally occurs within the first few hours of the animal's life. Infections with rotavirus and coronavirus are common in newborn calves and pigs. Rotavirus infection often occurs within 12 hours of birth. Symptoms of rotaviral infection include excretion of watery feces, dehydration and weakness. Coronavirus which causes a more severe illness in the newborn animals, has a higher mortality rate than rotaviral infection. Often, however, a young animal may be infected with more than one virus or with a combination of viral and bacterial microorganisms at one time. This dramatically increases the severity of the disease.

Yet another aspect of the present invention relates to a method for inhibiting the transport of a halide ion across a mammalian cell membrane expressing functional CFTR protein by contacting the cell expressing functional CFTR with an effective amount of the compound defined herein (including those compounds set forth in Tables 1-6 or encompassed by formulas I-VI) or compositions thereof, thereby inhibiting the transport of the halide ion. As used herein, the term "functional CFTR" intends the full length wild type CFTR protein, a functional equivalent, or a biologically active fragment thereof. CFTR has been isolated, cloned and recombinantly expressed in a variety of cell types, which include but are not limited to Fischer rat thyroid (FRT) epithelial cells, Human colonic T84 cells, intestinal crypt cells, colonic epithelial cells, mouse fibroblast cells, bronchial epithelial, tracheobronchial epithelial, sero/mucous epithelial cells, kidney cells. Such cells are known to those skilled in the art and described, for example in Galietta et al. (2001) J. Biol. Chem. 276(23):19723-19728; Sheppard et al. (1994) Am. J. Physiol. 266 (Lung Cell. Mol. Physiol. 10):L405-L413; Chao et al. (1989) Biophys. J. 56:1071-1081 and Chao et al. (1990) J. Membrane Biol. 113:193-202. CFTR-expressing cell lines also are available from the American Type Culture Collection (ATCC). The open reading frame and polypeptide sequence of wild-type CFTR has been previously described in U.S. Pat. Nos. 6,984,487; 6,902,907; 6,730,777; and 6,573,073. The delta 508 mutant is specifically (see U.S. Pat. Nos. 7,160,729 and 5,240,846) excluded as an equivalent polynucleotide or polypeptide. Equivalents of function CFTR include, but are not limited to polynucleotides that have the same or similar activity to transportions across the cell membrane. At the sequence level, equivalent sequences are at least 90% homologous (as determined under default parameters) to wild-type CFTR or those which hybridize under stringent conditions to the complement of these coding sequences. Biologically active functional fragments are those having contiguous identity to wild-type CFTR but contain less than 1480 amino acids. Functional fragments have been described. See U.S. Pat. Nos. 5,639,661 and 5,958,893.

The methods can be practiced in vivo in an acceptable animal model to confirm in vitro efficacy or to treat the disease or condition as described above.

Equivalent polynucleotides also include polynucleotides that are greater than 75%, or 80%, or more than 90%, or more than 95% homologous to wild-type CFTR and as further isolated and identified using sequence homology searches. Sequence homology is determined using a sequence alignment program run under default parameters and correcting for ambiguities in the sequence data, changes in nucleotide sequence that do not alter the amino acid sequence because of degeneracy of the genetic code, conservative amino acid substitutions and corresponding changes in nucleotide sequence, and variations in the lengths of the aligned sequences due to splicing variants or small deletions or insertions between sequences that do not affect function.

A variety of sequence alignment software programs are available in the art. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and Pileup. These programs are obtained commercially available in a comprehensive package of sequence analysis software such as GCG Inc.'s Wisconsin Package. Other similar analysis and alignment programs can be purchased from various providers such as DNA Star's MegAlign, or the alignment programs in GeneJockey. Alternatively, sequence analysis and alignment programs can be accessed through the world wide web at sites such as the CMS Molecular Biology Resource at sdsc.edu/ResTools/cmshp.html. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are known. They include but are not limited to p value, percent sequence identity and the percent sequence similarity. P value is the probability that the alignment is produced by chance. For a single alignment, the p value can be calculated according to Karlin et al. (1990) PNAS 87:2246. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

In one embodiment, the halide ion is at least one of $I^-$, $Cl^-$, or $Br^-$. In one preferred embodiment, the halide ion is $Cl^-$. In one embodiment, the functional CFTR is wild-type full length CFTR. In one embodiment, the mammalian cell is an epithelial cell or a kidney cell. In one preferred embodiment, the mammalian cell is an intestinal epithelial cell or a colon epithelial cell.

When used to treat or prevent the diseases responsive to inhibiting of functional CFTR, the compounds of the present invention can be administered singly, as mixtures of one or more compounds of the invention, or in mixture or combination with other agents useful for treating such diseases and/or the symptoms associated with such diseases. The compounds of the present invention may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, retuxin, PD4 inhibitors, p38 inhibitors, PDE4 inhibitors, and antihistamines, to name a few. The compounds of the invention can be administered per se in the form of prodrugs or as pharmaceutical compositions, comprising an active compound or prodrug.

The method can be practiced in vitro or in vivo. When practiced in vitro, the method can be used to screen for compounds, compositions and methods that possess the same or similar activity. Activity is determined using the methods described below or others known to those of skill in the art and described in Verkmann and Galietta (2006) Progress in Respiratory Research, Vol. 34, pages 93-101.

For example, Human colonic T84 cells can be acquired from the European Collection of Cell Cultures (ECACC) and grown in standard culture conditions as described by the supplier. On the day before assay 25,000 T84 cells per well are plated into standard black walled, clear bottom 384-well assay plates in standard growth medium consisting of DMEM:F12 with 10% FBS and incubated overnight. On the day of the assay the plates are washed using a standard assay buffer (HBSS with 10 mM Hepes) and incubated for 15 minutes in serum free cell culture medium before the addition of a commercially available membrane potential sensitive fluorescent dye (FLIPR Red membrane potential dye, Molecular Devices Corporation). T84 cells are incubated with the FLIPR Red membrane potential dye for 45 minutes in the presence and absence of test compound before being transferred to a commercially available fluorescence imaging plate reader (FLIPR384, Molecular Devices Corporation). Fluorescence levels are monitored continuously every second for 150 seconds; after an initial 10 second baseline, CFTR channel activity is stimulated through the addition of 10 μM Forskolin in the presence of 100 μM of the phosphodiesterase inhibitor iso-butyl-methylxanthine (IBMX). Addition of the forskolin leads to the activation of intracellular adenylyl cylase 1, elevating cAMP levels and results in the phosphorylation and opening of CFTR anion channels. CFTR channel opening causes chloride ion efflux and subsequent depolarization of the cells, which is measured by an increase in fluorescence. CFTR inhibitor compounds prevent cell depolarization and the associated increase in fluorescence.

For the purpose of illustration only, Fisher Rat Thyroid (FRT) cells stably co-expressing wildtype human CFTR and a reporter protein such as green fluorescent protein (GFP) or a mutant such as the yellow fluorescent protein-based $Cl^{31}/I^-$ halide sensor e.g. YFP-H148Q can be cultured on 96-well plates as described in Gruenert (2004), supra or Ma et al. (2002) J. Clin. Invest. 110:1651-1658. Following a 48 hour incubation confluent FRT-CFTR-YFP-H148Q cells in 96-well plates are washed three times with phosphate buffered saline (PBS) and then CFTR halide conductance is activated by incubation for 5 minutes with a cocktail containing 5 μM, forskolin, 25 μM apigenin and 100 μM, isobutylmethyl-xanthine (IBMX). Test compounds at a final concentration of 10 μM and 20 μM are added five minutes prior to assay of iodide influx in which cells are exposed to a 100 mM inwardly-directed iodide gradient. Baseline YFP fluorescence is recorded for two seconds followed by 12 seconds of continuous recording of fluorescence after rapid addition of the $I^-$ containing solution to create a $I^-$ gradient. Initial rates of $I^-$ influx can be computed from the time course of decreasing fluorescence after the $I^-$ gradient as known to those skilled in the art and described in Yang et al. (2002) J. Biol. Chem.: 35079-35085.

Activity of the CFTR channel can also be measured directly using electrophysiological methods. An example protocol of for measuring CFTR current is described as whole cell patch clamp method. As an illustration, recordings are conducted at room temperature (~21° C.) using a HEKA EPC-10 amplifier. Electrodes are fabricated from 1.7 mm capillary glass with resistances between 2 and 3 MΩ using a Sutter P-97 puller. For recording the CFTR channels, the extracellular solution can contain (in mM) 150 NaCl, 1 $CaCl_2$, 1 $MgCl_2$, 10 glucose, 10 mannitol, and 10 TES (pH 7.4), and the intracellular (pipette) solution can contain 120 CsCl, $MgCl_2$, 10 TEA-Cl, 0.5 EGTA, 1 Mg-ATP and 10 HEPES (pH 7.3).

The CFTR channels are activated by forskoin (5 μM) in the extracellular solution. The cells are held at a potential of 0 mV and currents were recording by a voltage ramp protocol from −120 mV to +80 mV over 500 ms every 10 seconds. No leak subtraction was employed. Compounds are superfused to individual cells using a Biologic MEV-9/EVH-9 rapid perfusion system.

Other in vitro methods for inhibitory activity have been described in the art, e.g., U.S. Patent Publication No. 2005/0239740 (paragraphs [0184] and [0185]). For PKD, therapeutic activity is determined using art recognized methods as described, for example in U.S. Patent Publications Nos.: 2006/0088828; 2006/0079515 and 2003/0008288.

For in vivo confirmatory studies for treatment of diarrhea, mice (CD1 strain, 25-35 g) are deprived of food prior to surgery and can be anaesthetized with any suitable agent such as intraperitoneal ketamine (40 mg/kg) and xylazine (8 mg/kg). Body temperature should be maintained at 36-38° C. using a heating pad. A small abdominal incision is made and 3 closed intestinal (ileal and/or duodenum/jejunum) loops (length 15-30 mm) proximal to the cecum are isolated by sutures. Loops are injected with 100 μL of PBS or PBS containing cholera toxin (1 μg) without or with test compound at appropriate doses. The abdominal incision is closed with suture and mice are allowed to recover from anesthesia. Approximately four to six hours later, the mice are anesthetized, intestinal loops are removed, and loop length and weight are measured to quantify net fluid secretion to be measured as g/cm of loop.

For in vivo confirmatory studies of PKD therapeutica activity, the Han:SPRD rat is well characterized and can be used as a model of ADPKD. Cowley B. et al. (1993) Kidney Int. 49:522-534; Gretz N. et al. (1996) Nephrol. Dial. Transplant 11:46-51; Kaspareit-Rittinghausen J. et al. (1990) Transpl. Proc. 22:2582-2583; and Schafer K. et al. (1994) Kidney Int. 46:134-152. Using this model, varying amount of the compounds or compositions are administered to the animals and therapeutic effect is noted.

D. Pharmaceutical Formulations and Administration

The compounds or isomers, prodrug, tautomer, or pharmaceutically acceptable salts thereof, of the present invention can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases may also be formed. The present invention includes within its scope solvates of the compounds and salts thereof, for example, hydrates. The compounds may have one or more asymmetric centers and may accordingly exist both as enantiomers and as diastereoisomers. It is to be understood that all such isomers and mixtures thereof are encompassed within the scope of the present invention.

In one embodiment, this invention provides a pharmaceutical formulation comprising a compound selected from the compounds of the invention or isomers, hydrates, tautomer, or pharmaceutically acceptable salts thereof and at least one pharmaceutically acceptable excipient, diluent, preservative, stabilizer, or mixture thereof.

In one embodiment, the methods can be practiced as a therapeutic approach towards the treatment of the conditions described herein. Thus, in a specific embodiment, the compounds of the invention can be used to treat the conditions described herein in animal subjects, including humans. The methods generally comprise administering to the subject an amount of a compound of the invention, or a salt, prodrug, hydrate, or N-oxide thereof, effective to treat the condition.

In some embodiments, the subject is a non-human mammal, including, but not limited to, bovine, horse, feline, canine, rodent, or primate. In another embodiment, the subject is a human.

The compounds of the invention can be provided in a variety of formulations and dosages. It is to be understood that reference to the compound of the invention, or "active" in discussions of formulations is also intended to include, where appropriate as known to those of skill in the art, formulation of the prodrugs of the compounds.

In one embodiment, the compounds are provided as non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine groups may also comprise quaternary ammonium salts in which the amino nitrogen atom carries a suitable organic group such as an alkyl, alkenyl, alkynyl, or substituted alkyl moiety. Furthermore, where the compounds of the invention carry an acidic moiety, suitable pharmaceutically acceptable salts thereof may include metal salts such as alkali metal salts, e.g., sodium or potassium salts; and alkaline earth metal salts, e.g., calcium or magnesium salts.

The pharmaceutically acceptable salts of the present invention can be formed by conventional means, such as by reacting the free base form of the product with one or more equivalents of the appropriate acid in a solvent or medium in which the salt is insoluble or in a solvent such as water which is removed in vacuo, by freeze drying, or by exchanging the anions of an existing salt for another anion on a suitable ion exchange resin.

Pharmaceutical compositions comprising the compounds described herein (or prodrugs thereof) can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

The compounds of the invention can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration.

The pharmaceutical compositions for the administration of the compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, and vaginal, or a form suitable for administration by inhalation or insufflation.

For topical administration, the compound(s) or prodrug(s) can be formulated as solutions, gels, ointments, creams, suspensions, etc., as is well-known in the art.

Systemic formulations include those designed for administration by injection (e.g., subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings. Additionally, the pharmaceutical compositions containing the 2,4-substituted pyrmidinediamine as active ingredient or prodrug thereof in a form suitable for oral use may also include, for example, troches, lozenges, aqueous, or oily suspensions, dispersible powders or granules, emulsions, hard or soft capsules, or syrups or elixirs.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166, 452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Preparations for oral administration can be suitably formulated to give controlled release or sustained release of the active compound, as is well known. The sustained release formulations of this invention are preferably in the form of a compressed tablet comprising an intimate mixture of compound of the invention and a partially neutralized pH-dependent binder that controls the rate of compound dissolution in aqueous media across the range of pH in the stomach (typically approximately 2) and in the intestine (typically approximately about 5.5).

To provide for a sustained release of compounds of the invention, one or more pH-dependent binders can be chosen to control the dissolution profile of the sustained release formulation so that the formulation releases compound slowly and continuously as the formulation is passed through the stomach and gastrointestinal tract. Accordingly, the pH-dependent binders suitable for use in this invention are those which inhibit rapid release of drug from a tablet during its residence in the stomach (where the pH is below about 4.5), and which promotes the release of a therapeutic amount of the compound of the invention from the dosage form in the lower gastrointestinal tract (where the pH is generally greater than about 4.5). Many materials known in the pharmaceutical art as "enteric" binders and coating agents have a desired pH dissolution properties. The examples include phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof. One or more pH-dependent binders present in the sustained release formulation of the invention are in an amount ranging from about 1 to about 20 wt %, more preferably from about 5 to about 12 wt % and most preferably about 10 wt %.

One or more pH-independent binders may be in used in oral sustained release formulation of the invention. The pH-independent binders can be present in the formulation of this invention in an amount ranging from about 1 to about 10 wt %, and preferably in amount ranging from about 1 to about 3 wt % and most preferably about 2 wt %.

The sustained release formulation of the invention may also contain pharmaceutical excipients intimately admixed with the compound and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth) acrylate esters, starch, gelatin, sugars, carboxymethylcellulose, and the like. Other useful pharmaceutical excipients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids can also be optionally present.

The sustained release formulations of this invention have a compound of this invention in the range of about 50% by weight to about 95% or more by weight, and preferably between about 70% to about 90% by weight; a pH-dependent binder content of between 5% and 40%, preferably between 5% and 25%, and more preferably between 5% and 15%; with the remainder of the dosage form comprising pH-independent binders, fillers, and other optional excipients.

For buccal administration, the compositions may take the form of tablets or lozenges formulated in the conventional manner.

For rectal and vaginal routes of administration, the active compound(s) can be formulated as solutions (for retention enemas), suppositories, or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant (e.g., dichlorodifluoromethane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges comprised of gelatin) can be formulated containing a powder mix of the compound and a suitable powder base such as lactose or starch.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution, and isotonic sodium chloride solution. The compounds may also be administered in the form of suppositories for rectal or urethral administration of the drug.

For topical use, creams, ointments, jellies, gels, solutions, suspensions, etc., containing the compounds of the invention, can be employed. In some embodiments, the compounds of the invention can be formulated for topical administration with polyethylene glycol (PEG). These formulations may optionally comprise additional pharmaceutically acceptable ingredients such as diluents, stabilizers, and/or adjuvants.

Included among the devices which can be used to administer compounds of the invention, are those well-known in the art, such as metered dose inhalers, liquid nebulizers, dry powder inhalers, sprayers, thermal vaporizers, and the like. Other suitable technology for administration of particular compounds of the invention, includes electrohydrodynamic aerosolizers. As those skilled in the art will recognize, the formulation of compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of compounds in the aerosol. For example, shorter periods of administration can be used at higher concentrations of compounds in the nebulizer solution. Devices such as metered dose inhalers can produce higher aerosol concentrations and can be operated for shorter periods to deliver the desired amount of compounds in some embodiments. Devices such as dry powder inhalers deliver active agent until a given charge of agent is expelled from the device. In this type of inhaler, the amount of compounds in a given quantity of the powder determines the dose delivered in a single administration.

Formulations of compounds of the invention for administration from a dry powder inhaler may typically include a finely divided dry powder containing compounds, but the powder can also include a bulking agent, buffer, carrier, excipient, another additive, or the like. Additives can be included in a dry powder formulation of compounds of the invention, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof, surfactants, such as sorbitols, diphosphatidyl choline, or lecithin; and the like.

For prolonged delivery, the compound(s) or prodrug(s) of the invention can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives (e.g., as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. Nos. 5,407,713.; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The compound(s) or prodrug(s) described herein, or compositions thereof, will generally be used in an amount effective to achieve the intended result, for example, in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an diarrhea provides therapeutic benefit not only when the diarrhea is eradicated or ameliorated, but also when the patient reports a decrease in the severity or duration of the symptoms associated with the diarrhea. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated, the age and weight of the patient, the bioavailability of the particular active compound. Determination of an effective dosage is well within the capabilities of those skilled in the art. As known by those of skill in the art, the preferred dosage of compounds of the invention will also depend on the age, weight, general health, and severity of the condition of the individual being treated. Dosage may also need to be tailored to the sex of the individual and/or the lung capacity of the individual, where administered by inhalation. Dosage, and frequency of administration of the compounds or prodrugs thereof, will also depend on whether the compounds are formulated for treatment of acute episodes of a condition or for the prophylactic treatment of a disorder. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay.

Calculating dosages to achieve such circulating blood or serum concentrations taking into account the bioavailability of the particular compound is well within the capabilities of skilled artisans. For guidance, the reader is referred to Fingl & Woodbury, "General Principles," IN: GOODMAN AND GILMAN'S THE PHARMACEUTICAL BASIS OF THERAPEUTICS, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the compounds of the invention is pertinent to dosages required for prodrugs, with the realization, apparent to the skilled artisan, that the amount of prodrug(s) administered will also depend upon a variety of factors, including, for example, the bioavailability of the particular prodrug(s) and the conversation rate and efficiency into active drug compound under the selected route of administration. Determination of an effective dosage of prodrug(s) for a particular use and mode of administration is well within the capabilities of those skilled in the art.

Also provided are kits for administration of the compounds of the invention, prodrug thereof, or pharmaceutical formulations comprising the compound that may include a dosage amount of at least one compound or a composition comprising at least one compound, as disclosed herein. Kits may further comprise suitable packaging and/or instructions for use of the compound. Kits may also comprise a means for the delivery of the at least one compound or compositions comprising at least one compound of the invention, such as an inhaler, spray dispenser (e.g., nasal spray), syringe for injection, or pressure pack for capsules, tables, suppositories, or other device as described herein.

Additionally, the compounds of the present invention can be assembled in the form of kits. The kit provides the compound and reagents to prepare a composition for administration. The composition can be in a dry or lyophilized form or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to, syringe, pipette, transdermal patch, or inhalant.

The kits may include other therapeutic compounds for use in conjunction with the compounds described herein. These compounds can be provided in a separate form or mixed with the compounds of the present invention. The kits will include appropriate instructions for preparation and administration of the composition, side effects of the compositions, and any other relevant information. The instructions can be in any suitable format, including, but not limited to, printed matter, videotape, computer readable disk, or optical disc.

In one embodiment, this invention provides a kit comprising a compound selected from the compounds of the invention or a prodrug thereof, packaging, and instructions for use.

In another embodiment, this invention provides a kit comprising the pharmaceutical formulation comprising a compound selected from the compounds of the invention or a prodrug thereof and at least one pharmaceutically acceptable excipient, diluent, preservative, stabilizer, or mixture thereof, packaging, and instructions for use. In another embodiment, kits for treating an individual who suffers from or is susceptible to the conditions described herein are provided, comprising a container comprising a dosage amount of a compound of this invention or composition, as disclosed herein, and instructions for use. The container can be any of those known in the art and appropriate for storage and delivery of oral, intravenous, topical, rectal, urethral, or inhaled formulations.

Kits may also be provided that contain sufficient dosages of the compounds or composition to provide effective treatment for an individual for an extended period, such as a week, 2 weeks, 3, weeks, 4 weeks, 6 weeks, or 8 weeks or more.

E. General Synthesis of the Compounds of the Invention

The compounds and prodrugs of the invention can be synthesized via a variety of different synthetic routes using commercially available starting materials and/or starting materials prepared by conventional synthetic methods. It will also be appreciated by those skilled in the art that in the process described below, the functional groups of intermediate compounds may need to be protected by suitable protecting groups.

The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, PROTECTIVE GROUPS IN ORGANIC SYNTHESIS, 3d Edition, John Wiley & Sons, Inc., New York (1999) and the references cited therein. Examples of functional groups include hydroxy, amino, mercapto and carboxylic acid.

Thus, "protecting group" refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and, additionally, in Harrison et al., COMPENDIUM OF SYNTHETIC ORGANIC METHODS, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC"), and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups), aryl silyl ethers (e.g., triphenylsilyl ether), mixed alkyl and aryl substituted silyl ethers, and allyl ethers.

The following Reaction Schemes illustrate methods to make compounds of the invention. It is understood that one of ordinary skill in the art would be able to make the compounds of the invention by similar methods or by methods known to one skilled in the art. In general, starting components may be obtained from sources such as Aldrich, or synthesized according to sources known to those of ordinary skill in the art (see, e.g., Smith and March, MARCH'S ADVANCED ORGANIC CHEMISTRY: REACTIONS, MECHANISMS, AND STRUCTURE, 5th edition (Wiley Interscience, New York)). Moreover, the various substituted groups (e.g., R, $R^1$-$R^5$, X, Y etc.) of the compounds of the invention may be attached to the starting components, intermediate components, and/or final products according to methods known to those of ordinary skill in the art.

A variety of exemplary synthetic routes that can be used to synthesize the compounds of the invention are described in Schemes I-VIII below. Specifically, compounds of formula I, II, III, IV, V and VI can be synthesized using the methods disclosed hereinbelow. These methods can be routinely adapted to synthesize the compounds and prodrugs described herein.

In one exemplary embodiment, various compounds of formula I, represented by formula IA, can be synthesized from esters I-1 as illustrated in Scheme I, below:

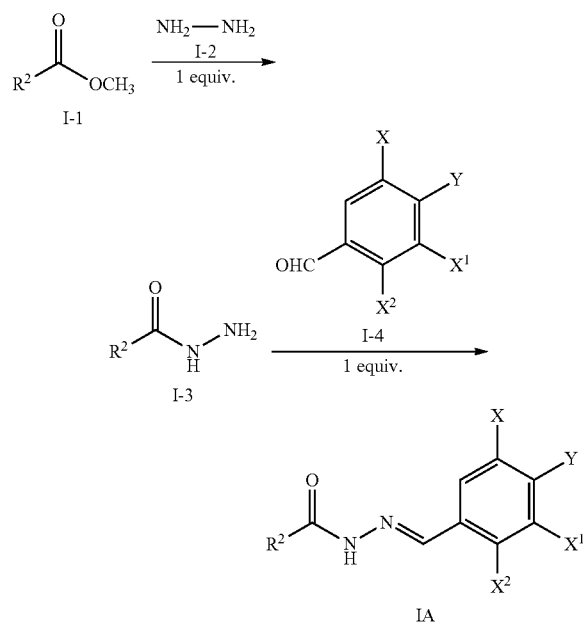

SCHEME I

In Scheme I, the groups $R^2$, X, $X^1$, $X^2$ and Y are as defined herein. The starting esters I-1 can be purchased from commercial sources or prepared using standard techniques of organic chemistry. For example, the starting esters I-1 can be prepared from suitable acids by a standard esterification reaction by refluxing the acid with methanol, and a base such as sodium hydroxide (NaOH).

Compound I-3 is prepared by conventional methods. Typically, such methods include reaction of compound I-1 with at least an equimolar amount of hydrazine 1-2 and preferably a slight excess thereof in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 24 hours and preferably 5-15 hours. Whereupon, the resulting hydrazide, compound I-3, is recovered by conventional methods such as evaporation, chromatography, precipitation, crystallization, and the like or, alternatively, used in the next step without purification and/or isolation. In a preferred embodiment, compound I-3 is recovered by evaporation followed by recrystallization in a suitable solvent such as ethanol.

Hydrazide, I-3, is converted to hydrazone, compound IA, by conventional condensation reaction conditions in the presence of I-4. Specifically, approximately equimolar amounts of hydrazide, I-3, and I-4, are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting hydrazone, compound IA, is recovered by conventional methods such as evaporation, chromatography, precipitation, crystallization, and the like. In a preferred embodiment, compound IA is recovered by filtration of the reaction mixture.

The reactions depicted in Scheme I may proceed more quickly when the reaction solutions are rapidly heated by, e.g., a microwave. Compounds I-4 can be purchased from commercial sources or prepared using standard techniques of organic chemistry. For example, aldehydes I-4 can be synthesized from suitable alcohol precursors by oxidation using standard synthetic organic chemistry. See also Vogel, 1989, PRACTICAL ORGANIC CHEMISTRY, Addison Wesley Longman, Ltd. and John Wiley & Sons, Inc.

Skilled artisans will recognize that in some instances, compounds I-1 and I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, PROTECTIVE GROUPS IN ORGANIC SYNTHESIS, 3d Edition, John Wiley & Sons, Inc., New York (1999) and the references cited therein (hereinafter "Greene & Wuts").

In one exemplary embodiment, additional intermediates for the synthesis of compounds of formula I represented by formula IA' (i.e. compounds of formula wherein $R^1$ is not hydrogen) can be synthesized from substituted alkyl halides II-1 as illustrated in Scheme II below:

SCHEME II

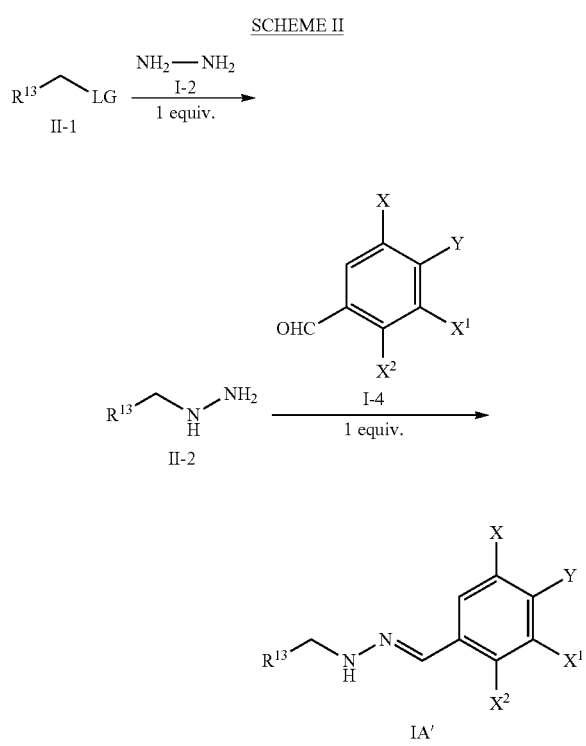

In Scheme II, the groups X, $X^1$, $X^2$ and Y are as defined herein and LG is a leaving group exemplified by a halo group such as chloro, bromo or iodo. $R^{13}$ is a precourser to $R^1$.

Compound II-2 is prepared by conventional methods. Specifically, as in Scheme II, approximately equimolar amounts of compound II-1 and hydrazine, compound I-2, or a slight excess of hydrazine are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting substituted hydrazine, compound II-2, is recovered by conventional methods such as evaporation, chromatography, precipitation, crystallization, and the like or alternatively used in the next step without purification and/or isolation. In a preferred embodiment, compound II-2 is recovered by evaporation followed by recrystallization in a suitable solvent such as ethanol.

Substituted hydrazine, II-2, is converted to hydrazone, compound IA', by conventional condensation reaction conditions, as discussed above, in the presence of aldehyde I-4. The resulting hydrazone, compound IA', is recovered by conventional methods such as filtration, evaporation, chromatography, precipitation, crystallization, and the like. In a preferred embodiment, compound IA' is recovered by filtration of the reaction mixture.

The starting substituted alkyl halides II-1 can be purchased from commercial sources or prepared using standard techniques of organic chemistry. For example, the substituted alkyl halides II-1 with LG as chloro group, is prepared by chloromethylation of $R^{13}$ group by combining $R^{13}$ group with an equimolar amount of paraformaldehyde and excess of finely powdered anhydrous zinc chloride. The reaction mixture is heated at 60° C. under a rapid stream of hydrogen chloride until no more gas is absorbed (about 20 minutes). After washing the contents of the reaction with water, and saturated sodium bicarbonate solution, the reaction mixture is dried using anhydrous calcium chloride or magnesium sulfate. The solvent is distilled under reduced pressure to yield II-1 with LG as chloro group. Alternatively, the starting esters II-1 with LG as chloro group, can be prepared by chlorination of $R^{13}$—OH. For example, for preparing benzyl chloride, benzyl alcohol and excess of concentrated hydrochloric acid are mixed and slowly heated at 60° C. to yield benzyl chloride. Benzyl bromide and benzyl iodide can be prepared in the same way from the corresponding hydrobromide and hydroiodide, respectively.

Similar reactions are known in the art to prepare II-1 compounds with LG as a bromo group. See also Vogel, 1989, PRACTICAL ORGANIC CHEMISTRY, Addison Wesley Longman, Ltd. and John Wiley & Sons, Inc.

The reactions depicted in Scheme II may proceed more quickly when the reaction solutions are rapidly heated by, e.g., a microwave. Skilled artisans will recognize that in some instances, compound II-1 and aldehyde I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, various compounds of formula I, represented by formula III-8, can be synthesized from substituted esters III-1 as illustrated in Scheme III below:

SCHEME III

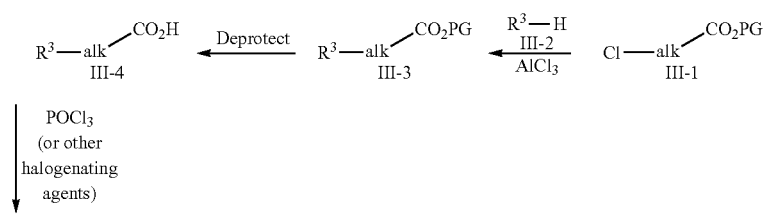

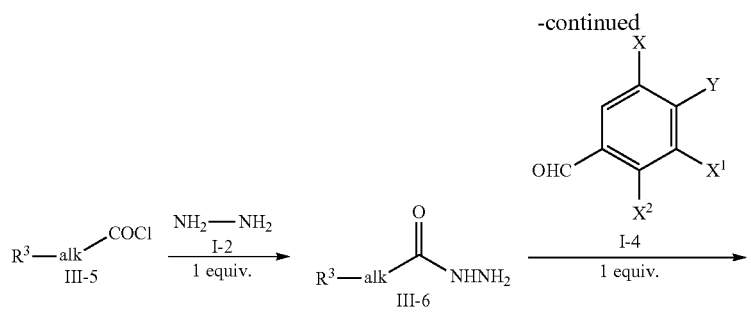
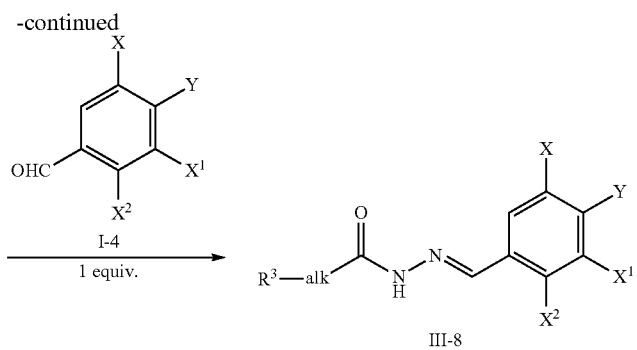

In Scheme III, the groups alk, $R^3$, X, $X^1$, $X^2$, and Y are as defined herein. PG represents a protecting group.

Compound III-6 is prepared by conventional methods. Specifically, in Scheme III, approximately equimolar amounts of compound III-5 and hydrazine, compound I-2, or a slight excess of hydrazine are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting substituted hydrazide, compound III-6, is recovered by conventional methods such as evaporation, chromatography, precipitation, crystallization, and the like or alternatively used in the next step without purification and/or isolation. In a preferred embodiment, compound III-6 is recovered by evaporation followed by recrystallization in a suitable solvent such as ethanol.

Substituted hydrazide, III-6, is converted to hydrazone, compound III-8, by conventional condensation reaction conditions, as discussed above, in the presence of aldehyde I-4. The resulting hydrazone, compound III-8, is recovered by conventional methods such as evaporation, chromatography, precipitation, crystallization, and the like. In a preferred embodiment, compound III-8 is recovered by filtration of the reaction mixture Compound, III-5, can be purchased from commercial sources or prepared using standard techniques of organic chemistry. For example, III-5 can be synthesized as shown in Scheme III. III-1 can be prepared by protecting an aliphatic acid with a protecting group as described herein. The protected aliphatic acid can be brominated or chlorinated by a reaction of protected aliphatic acid with phosphorus halide. Similar reactions are known in the art to prepare III-1 compounds. See also Vogel, 1989, PRACTICAL ORGANIC CHEMISTRY, Addison Wesley Longman, Ltd. and John Wiley & Sons, Inc. Compound, III-2, can be refluxed with an equimolar amount of III-1 under standard conditions in the presence of a Lewis acid catalyst such as, anhydrous aluminium chloride ($AlCl_3$) using a suitable solvent to give III-3. Examples of suitable solvents include, but are not limited to, nitrobenzene, carbon disulfide, ether, methylene chloride and the like. Other Lewis acid catalysts that may also be used include, but are not limited to, hydrogen fluoride (HF), sulfuric acid ($H_2SO_4$), phosphoric acid ($H_3PO_4$) and the like. The reaction can be carried out for up to 10 hrs. Further, III-3 is deprotected using methods well known in the art to give III-4 which is then halogenated using a standard halogenating agent such as $POCl_3$ (or other standard halogenating agent) under standard conditions to yield III-5.

The reactions depicted in Scheme III may proceed more quickly when the reaction solutions are rapidly heated by, e.g., a microwave. Skilled artisans will recognize that in some instances, compound III-2 and aldehyde I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, various compounds of formula IV, represented by formula IV-8, can be synthesized from substituted amino acids IV-1 as illustrated in Scheme IV below:

SCHEME IV

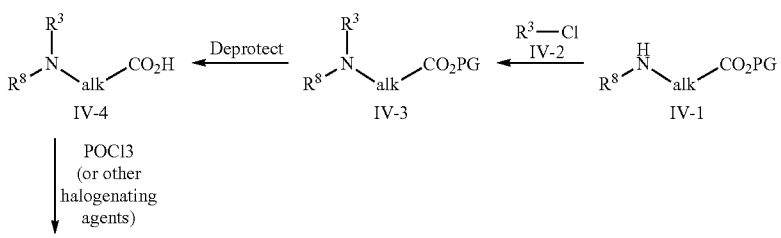

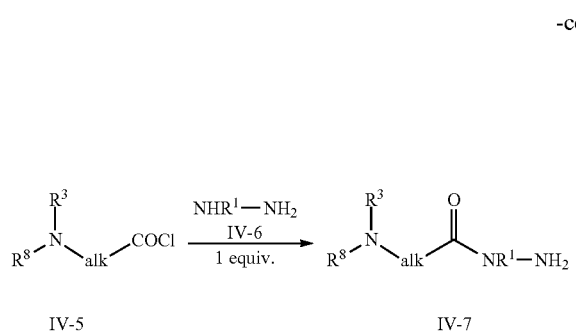
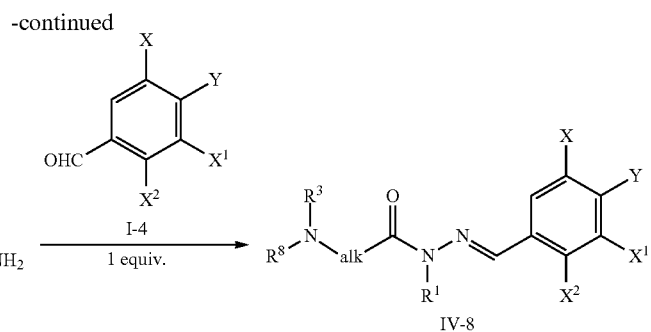

In Scheme IV, the groups $R^3$, $R^1$, X, $X^1$, $X^2$, and Y are as defined herein. PG represents a protecting group. $R^8$ is a protecting group, hydrogen or alkyl.

Compound IV-7 is prepared by conventional methods. Specifically, in Scheme IV, approximately equimolar amounts of compound IV-5 and substituted hydrazine, compound IV-6, or a slight excess of hydrazine are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting substituted hydrazide, compound IV-7, is recovered by conventional methods such as evaporation, chromatography, precipitation, crystallization, and the like or alternatively used in the next step without purification and/or isolation. In a preferred embodiment, compound IV-7 is recovered by evaporation followed by recrystallization in a suitable solvent such as ethanol.

Substituted hydrazide, IV-7, is converted to hydrazone, compound IV-8, by conventional condensation reaction conditions, as discussed above, in the presence of aldehyde I-4. The resulting hydrazone, compound IV-8, is recovered by conventional methods such as evaporation, chromatography, precipitation, crystallization, and the like. In a preferred embodiment, compound IV-8 is recovered by filtration of the reaction mixture Referring to Scheme IV, IV-5 can be purchased from commercial sources or prepared using standard techniques of organic chemistry. For example, IV-1 can be prepared by a carboxylic group of a suitable amino acid protected with a protecting group. The protected amino acid IV-1 is treated with IV-2 and is refluxed until the completion of the reaction to yield IV-3. Further, IV-3 is deprotected using methods well known in the art to give IV-4 which is then halogenated using a standard halogenating agent such as $POCl_3$ (or other standard halogenating agent) under standard conditions to yield IV-5.

The reactions depicted in Scheme IV may proceed more quickly when the reaction solutions are rapidly heated by, e.g., a microwave. Skilled artisans will recognize that in some instances, compound IV-2 and aldehyde I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, the compounds of formula I, represented by formula V-7, can be synthesized from α-halo esters V-1 as illustrated in Scheme V below:

SCHEME V

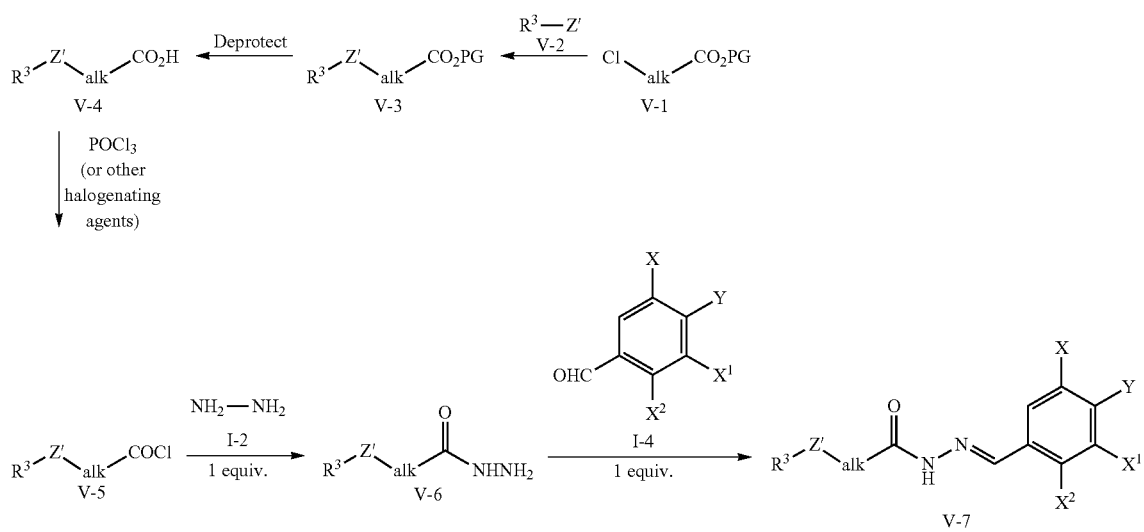

In Scheme V, the groups alk, $R^3$, X, $X^1$, $X^2$, Z' and Y are as defined herein. PG represents a protecting group.

Compound V-6 is prepared by conventional methods. Specifically, in Scheme V, approximately equimolar amounts of compound V-5 and hydrazine, compound I-2, or a slight excess of hydrazine are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting substituted hydrazide, compound V-6, is recovered by conventional methods such as evaporation, chromatography, precipitation, crystallization, and the like or alternatively used in the next step without purification and/or isolation. In a preferred embodiment, compound V-6 is recovered by evaporation followed by recrystallization in a suitable solvent such as ethanol.

Substituted hydrazide, V-6, is converted to hydrazone, compound V-7, by conventional condensation reaction conditions, as discussed above, in the presence of aldehyde I-4. The resulting hydrazone, compound V-7, is recovered by conventional methods such as evaporation, chromatography, precipitation, crystallization, and the like. In a preferred embodiment, compound V is recovered by filtration of the reaction mixture Referring to Scheme V, V-5 can be purchased from commercial sources or prepared using standard techniques of organic chemistry. For example, an aliphatic acid is converted to its corresponding ester by treating with methanol in the presence of a base. The resulting ester is halogenated using standard halogenating agents such as $POCl_3$ to yield V-1. The protected α-halo ester V-1 is treated with V-2 in the presence of solid potassium hydroxide (KOH) and dimethyl sulfoxide (DMSO) under standard conditions to yield V-3. Further, V-3 is deprotected using methods well known in the art to give V-4 which is then halogenated using a standard halogenating agent such as $POCl_3$ (or other standard halogenating agent) under standard conditions to yield V-5.

The reactions depicted in Scheme V may proceed more quickly when the reaction solutions are rapidly heated by, e.g., a microwave. Skilled artisans will recognize that in some instances, compound V-2 and aldehyde I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, the compounds of formula I, represented by formula VI-7, can be synthesized from sulfonyl halides VI-1 as illustrated in Scheme VI below:

SCHEME VI

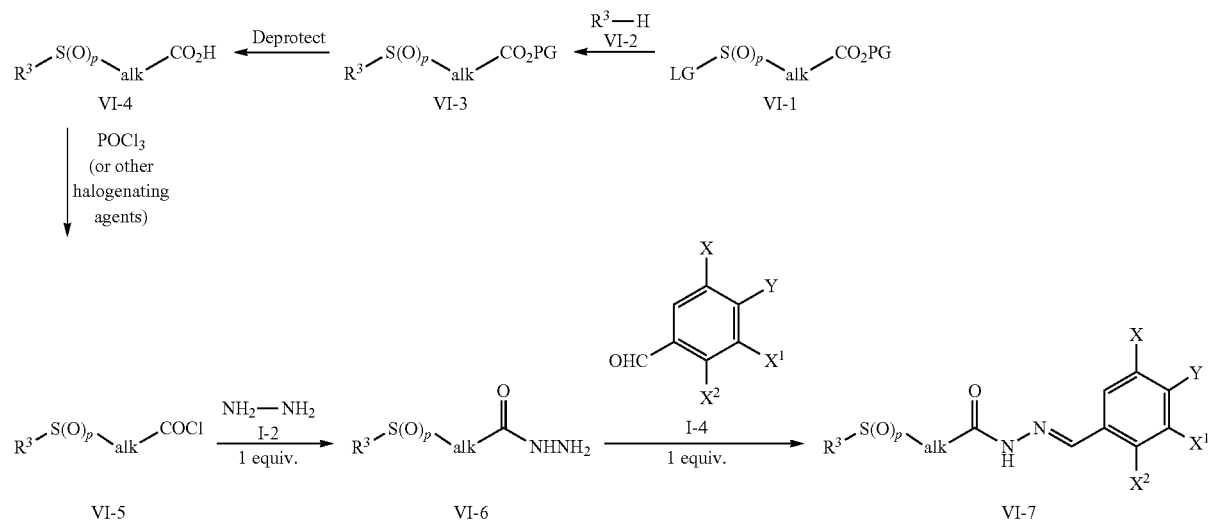

In Scheme VI, the groups alk, $R^3$, X, $X^1$, $X^2$, and Y are as defined herein. PG represents a protecting group, LG represents a leaving group and integer p is zero or two.

Compound VI-6 is prepared by conventional methods. Typically, such methods include reaction of compound VI-5 with at least an equimolar amount of hydrazine I-2 and preferably a slight excess thereof in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 24 hours and preferably 5-15 hours. Whereupon, the resulting hydrazide, compound VI-6, is recovered by conventional methods such as evaporation, chromatography, precipitation, crystallization, and the like or, alternatively, used in the next step without purification and/or isolation. In a preferred embodiment, compound VI-6 is recovered by evaporation followed by recrystallization in a suitable solvent such as ethanol.

Hydrazide, VI-6, is converted to hydrazone, compound VI-7, by conventional condensation reaction conditions in the presence of aldehyde I-4. Specifically, approximately equimolar amounts of hydrazide, VI-6, and aldehyde, I-4, are combined in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 12 hours and preferably 3-5 hours. Whereupon, the resulting hydrazone, compound VI-7, is recovered by conventional methods such as evaporation, chromatography, precipitation, crystallization, and the like. In a preferred embodiment, compound VI-7 is recovered by cold filtration of the reaction mixture.

Referring to Scheme VI, VI-5 can be purchased from commercial sources or prepared using standard techniques of organic chemistry. The sulfonyl halide VI-1 is treated with VI-2 in the presence of Lewis acid catalyst such as, $AlCl_3$, under standard conditions using a suitable solvent to give VI-3. Examples of suitable solvents include, but are not limited to, nitrobenzene, carbon disulfide, ether, methylene chloride and the like. Other Lewis acid catalysts that may also be used include, but are not limited to, HF, $H_2SO_4$, $H_3PO_4$ and the like. The progress of the reaction is monitored on TLC or HPLC. After the completion of the reaction, the solvent and the excess reagent is removed under reduced pressure. The crude VI-3 obtained may be used as is in the next step or may be recrystallized using ethanol. Further, VI-3 is deprotected using methods well known in the art to give VI-4 which is then halogenated using a standard halogenating agent such as $POCl_3$ (or other standard halogenating agent) under standard conditions to yield VI-5.

The reactions depicted in Scheme VI may proceed more quickly when the reaction solutions are rapidly heated by, e.g., a microwave. Skilled artisans will recognize that in some instances, compound VI-2 and aldehyde I-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, the compounds of formula I, represented by formula II, can be synthesized from aldehydes VII-1 as illustrated in Scheme VII below:

In Scheme VI, the groups $R^2$, X, $X^1$, $X^2$ and Y are as defined herein. PG represents a protecting group. M represents a metal such as lithium or magnesium.

Compound VII-5 is prepared by conventional methods. Typically, such methods include reaction of compound VII-4 with at least an equimolar amount of hydrazine and preferably a slight excess thereof in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 24 hours and preferably 1 to 5 hours. Whereupon, the resulting pyrazole, is recovered by conventional methods such as evaporation, chromatography, precipitation, crystallization, and the like or, alternatively, used in the next step without purification and/or isolation. The pyrazole is then reacted under standard acylation conditions to form compound VII-5. Specifically, approximately equimolar amounts of pyrazole and acylhalide, or other activated carbonyl, are combined in a suitable diluent such as dichloromethane under an inert atmosphere. The reaction is typically conducted at room temperature, or alternatively, at 0° C. and allowed to warm slowly to room temperature. The reaction is continued until substantially complete as evidenced by, e.g., thin layer chromatography or high performance liquid chromatography which typically occurs within 16 to 72 hours.

Pyrazole, VII-5, is converted to the target compound II, by conventional phenol deprotection reaction conditions. Whereupon, the resulting target compound II, is recovered by conventional methods such as evaporation, chromatography, precipitation, crystallization, and the like. In a preferred embodiment, compound II is recovered by filtration of the reaction mixture.

Referring to Scheme VII, VII-4 can be prepared using standard techniques of organic chemistry. Alcohol VII-3 can be oxidized to form ketone VII-4 under standard oxidation conditions. Specifically, alcohol VII-3 can be treated with a suitable oxidant at room temperature. Examples of other suit-

SCHEME VII

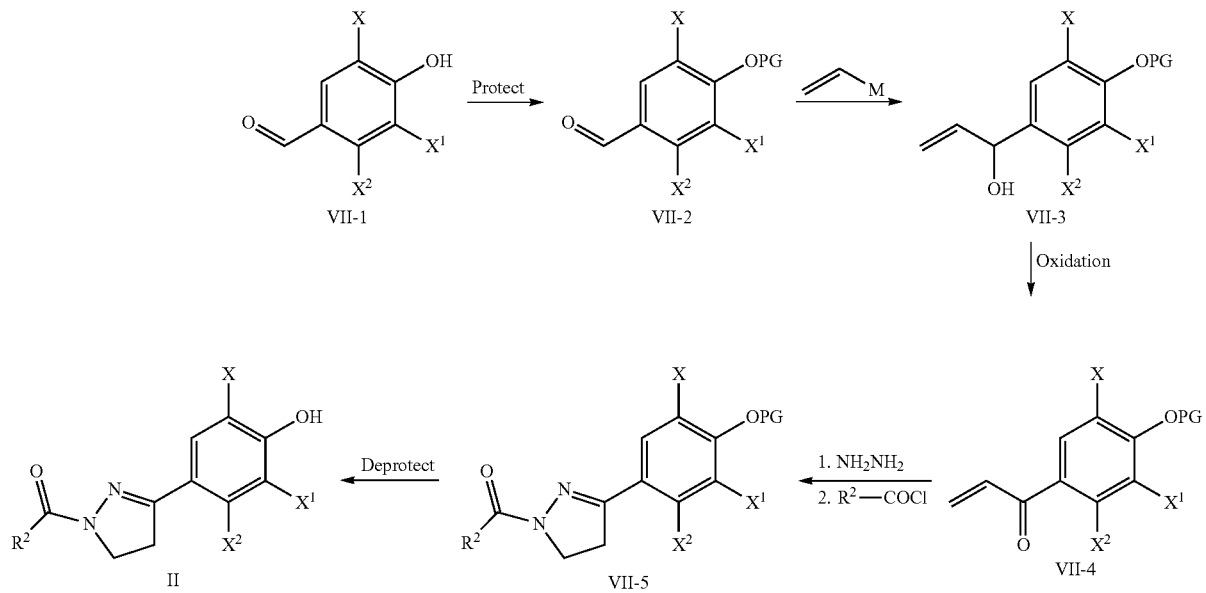

able oxidants include, but are not limited to, manganese dioxide, hypervalent iodide reagents, pyridinium chlorochromate (PCC), Jones reagent, Swern oxidation, and the like. Preferably, manganese dioxide can be used in a solvent such as chloroform at room temperature for 1-5 hours. The progress of the reaction is monitored on TLC or HPLC. After the completion of the reaction, the solvent and the excess reagent is removed under reduced pressure. The crude VII-4 obtained may be used as is in the next step or, more preferably, may be purified using flash chromatography.

Alcohol VII-3 can be prepared using standard techniques of organic chemistry. For example, alcohol VII-3 can be prepared from the corresponding aldehyde VII-2 using the appropriate organometallic reagent. Aldehyde VII-2 can be purchased from commercial sources and protected using standard techniques of organic chemistry. Specifically, vinylmagnesium bromide or vinyllithium reagents can be used in a suitable solvent to form allylic alcohol VII-3. Examples of suitable solvents include, but are not limited to, tetrahydrofuran, ethers, dioxane, hydrocarbon solvents, and the like. The reactions are typically performed at low temperatures between −80 and −70° C. The reaction proceeds at low temperature (typically 1 to 3 hours) or until substantially complete, at which time the reaction is warmed to room temperature. Whereupon, the resulting allylic alcohol VII-2, is recovered by conventional methods such as evaporation, chromatography, precipitation, crystallization, and the like or, alternatively, used in the next step without purification and/or isolation.

The reactions depicted in Scheme VII may proceed more quickly when the reaction solutions are rapidly heated by, e.g., a microwave. Skilled artisans will recognize that in some instances, the acylchloride $R^2$—COCl and aldehyde VII-2 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

In another exemplary embodiment, the compounds of formula I, represented by formula III, can be synthesized from ketones VIII-1 as illustrated in Scheme VIII below:

SCHEME VIII

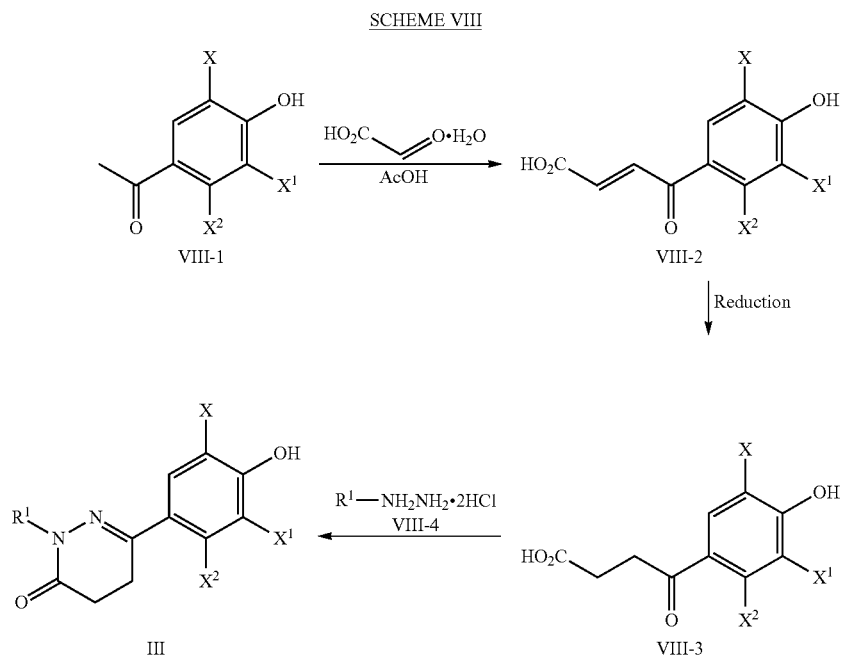

In Scheme VIII, the groups $R^1$, X, $X^1$, $X^2$, and Y are as defined herein.

Compound VIII-2 is prepared by conventional methods. Specifically, approximately equimolar amounts of ketone VIII-1 and glyoxylic acid, are combined in a suitable solvent such as acetic acid. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 3 to 7 days and preferably 4-6 days. Whereupon, the resulting unsaturated γ-keto acid, compound VIII-2, is recovered by conventional methods such as evaporation, chromatography, precipitation, crystallization, and the like or alternatively used in the next step without purification and/or isolation. In a preferred embodiment, compound II-2 is recovered by evaporation followed by recrystallization in a suitable solvent such as toluene.

Unsaturated y-keto acid, compound VIII-2, is selectively reduced to yield compound VIII-3, by conventional reduction reaction conditions, such as zinc powder in an aqueous ethyl acetate reaction medium. The resulting γ-keto acid, compound VIII-3, is recovered by conventional methods such as filtration, evaporation, chromatography, precipitation, crystallization, and the like. In a preferred embodiment, compound VIII-3 is recovered by filtration of the reaction mixture.

Compound III is prepared by conventional methods. Typically, such methods include reaction of compound VIII-3 with at least an equimolar amount of hydrazine VIII-4 and preferably a slight excess thereof in a suitable inert diluent such as methanol, ethanol and the like. The reaction is typically conducted at elevated temperatures and preferably at the reflux temperature of the selected solvent. The reaction is continued until substantially complete as evidenced by, e.g., thin layer chromatography or high performance liquid chromatography which typically occurs within 1 to 24 hours and preferably 5-18 hours. Whereupon, the resulting target compound III, is recovered by conventional methods such as evaporation, chromatography, precipitation, crystallization, and the like or, alternatively, used in the next step without purification and/or isolation. In a preferred embodiment, compound III is recovered by evaporation followed by recrystallization in a suitable solvent such as ethanol.

The reactions depicted in Scheme II may proceed more quickly when the reaction solutions are rapidly heated by, e.g., a microwave. Skilled artisans will recognize that in some instances, the substituted ketones VIII-1 and hydrazine VIII-4 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts.

The following examples are intended to illustrate the various embodiments of this invention.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

In the examples below as well as throughout the application, the following abbreviations have the following meanings. If not defined, the terms have their generally accepted meanings.

| | |
|---|---|
| AcOH = | Acetic Acid |
| APCI = | Atmospheric pressure chemical ionization |
| ATP = | Adenosine Tri-Phospate |
| br = | Broad |
| d = | Doublet |
| DMEM = | Dulbecco's Modified Eagle's Medium |
| DMF = | Dimethylformamide |
| DMSO = | Dimethylsulfoxide |
| EGTA = | Ethylene Glycol Tetraacetic Acid |
| Et = | Ethyl |
| EtOAc = | Ethyl acetate |
| EtOH = | Ethanol |
| FBS = | Fetal Bovine Serum |
| g = | Gram |
| LC = | Liquid chromatography |
| LCMS = | Liquid Chromatography Mass Spectrometry |
| m = | Multiplet |
| m/z = | Mass/Charge |
| Me = | Methyl |
| mg = | Milligram |
| MHz = | Megahertz |
| min = | Minute |
| mL = | Milliliter |
| mm = | Millimeter |
| mM = | Milimolar |
| mmol = | Millimole |

-continued

| | |
|---|---|
| ms = | Millisecond |
| MS = | Mass spectrum |
| mV = | Millivolt |
| MΩ= | Megaohm |
| N = | Normal |
| NaOAc = | Sodium acetate |
| ng = | Nanogram |
| nM = | Nanomolar |
| nm = | Nanometer |
| NMR = | Nuclear magnetic resonance |
| pet = | petroleum |
| PMB = | p-Methoxybenzyl |
| ppm = | Parts per million |
| q = | Quartet |
| Rt = | Retention time |
| rt = | Room temperature |
| s = | Singlet |
| t = | Triplet |
| TEA = | Triethylamine |
| UV = | Ultraviolet |
| v/v = | Volume/Volume |
| μg = | Microgram |
| μL= | Microliter |
| μm = | Micrometer |
| μM = | Micromolar |

General Synthetic Methods

Unless otherwise stated, all chemicals were purchased from commercial suppliers and used without further purification. NMR spectra were recorded on Bruker 400 MHz spectrometers. Chemical shifts are reported in parts per million downfield from the internal standard $Me_4Si$ (0.0 ppm) for $CDCl_3$ solutions. For DMSO-$d_6$ solutions, calibration was done on the solvent peak at 2.49 ppm.

Standard Acidic LC-MS Conditions: (10 cm_esci_formic or 10 cm_apci_formic)

A Phenomenex Luna 5 μm C18 (2), 100×4.6 mm. (plus guard cartridge) column using an acetonitrile (Far UV grade) with 0.1% (v/v) formic acid:Water (High purity via Elga UHQ unit) with 0.1% formic acid gradient was used. The flow rate was 2 mL/min. UV detection was done using a Waters diode array detector (start range 210 nm, end range 400 nm, range interval 4.0 nm). Mass detection was via a single quadrupole LCMS instrument. Ionization is either ESCi™ or APCI dependent on compound types. The gradient used ran from 95% of aqueous solvent at time 0.00 min to 5% of aqueous solvent at 3.50 min. This percentage was then held for a further 2 min.

Standard Basic LC-MS Conditions: (10 cm_esci_bicarb or 10 cm_apci_bicarb)

A Waters Xterra MS 5 μm C18, 100×4.6 mm. (plus guard cartridge) column using an acetonitrile (Far UV grade):water (High purity via Elga UHQ unit) with 10 mM ammonium bicarbonate (ammonium hydrogen carbonate) gradient was used. The flow rate was 2 mL/min. UV detection was done using a Waters diode array detector (start range 210 nm, end range 400 nm, range interval 4.0 nm). Mass detection was via a single quadrupole LCMS instrument. Ionization is either ESCi™ or APCI dependent on compound types. The gradient used ran from 95% of aqueous solvent at time 0.00 min to 5% of aqueous solvent at 3.50 min. This percentage was then held for a further 2 min.

Example 1

(E)-N'-(3,5-dibromo-4-hydroxybenzylidene)-2-hydroxy-2,2-diphenylacetohydrazide (1)

$^1$H NMR δ (ppm) (DMSO-d$_6$): 7.03 (1 H, s), 7.31-7.46 (10 H, m), 7.83 (2 H, s), 8.41 (1 H, s), 10.48 (1 H, br s), 11.61 (1 H, s). LCMS (10 cm_esci_bicarb) Rt 2.6 min; m/z 503/505/507 [M+H].

Example 2

(E)-N'-(3,5-dibromo-4-hydroxybenzylidene)-2-(4-isobutylphenyl)propanehydrazide (2)

$^1$H NMR δ (ppm) (DMSO-d$_6$): 0.84 and 0.88 (6 H, two d, J=6.6 Hz), 1.39 and 1.41 (3 H, two d, J=7.0 Hz), 1.75-1.88 (1 H, m), 2.35-2.47 (2 H, m), 3.68 and 4.58 (1 H, two q, J=7.0 Hz) 7.12 (2 H, m), 7.25 (1 H, d, J=7.9 Hz), 7.29 (1 H, d, J=7.9 Hz), 7.81 and 7.87 (2 H, two s), 7.78 and 8.07 (1 H, two s), 10.38 (1 H, br s), 11.29 and 11.59 (1 H, two s). LCMS (10 cm_esci_bicarb) Rt 3.08 min; m/z 481/483/485 [M+H].

Example 3

(E)-N'-(3,5-dibromo-4-hydroxybenzylidene)-3-(4-(trifluoromethoxy)phenoxy)benzohydrazide (3)

$^1$H NMR δ (ppm) (DMSO-d$_6$): 7.18-7.24 (2 H, m), 7.32 (1 H, dd, J=8 and 4 Hz), 7.46 (2 H, d, J=8 Hz), 7.58-7.64 (2 H, m), 7.78 (1 H, d, J=8 Hz), 7.94 (2 H, s), 8.32 (1 H, s), 10.50 (1 H, br s), 12.00 (1 H, s). LCMS (10 cm_esci_bicarb) Rt 3.11 min; m/z 573/575/577 [M+H].

Example 4

(E)-2-(4-chlorophenylamino)-N'-(3,5-diiodo-4-hydroxybenzylidene)acetohydrazide (4)

$^1$H NMR δ (ppm) (DMSO-d$_6$): 4.24 and 3.82 (2 H, two s), 6.00 and 6.22 (1 H, two br s), 6.68-6.60 (2 H, m), 7.16-7.10 (2 H, m), 7.87 and 8.05 (1 H, two s), 8.12-8.06 (2 H, m), 9.93 (1 H, br s), 11.46 and 11.47 (1 H, two s). LCMS (10 cm_esci_bicarb) Rt 2.66 min; m/z 556/558 [M+H].

Example 5

(E)-N'-(3,5-dibromo-4-hydroxybenzylidene)-3-(4-(trifluoromethyl)phenoxy)benzohydrazide (5)

$^1$H NMR δ (ppm) (DMSO-d$_6$): 7.24 (2 H, d, J=12 Hz), 7.41 (1 H, d, J=8 Hz), 7.66 (1 H, t, J=8 Hz), 7.70 (1 H, s), 7.73-7.86 (3 H, m), 7.95 (2 H, s), 8.33 (1 H, s), 10.49 (1 H, br s), 12.00 (1 H, s). LCMS (10 cm_esci_bicarb) Rt 2.9 min; m/z 557/559/561 [M+H].

Example 6

(E)-N'-(3,5-dibromo-4-hydroxybenzylidene)-2-(2,4-dichlorophenoxy)propanehydrazide (6)

$^1$H NMR δ (ppm) (DMSO-d$_6$): 1.58 (3 H, t), 4.92 and 5.77 (1 H, two q), 6.98 and 7.03 (1H, two d), 7.37-7.42 (1 H, m), 7.59 and 7.65 (1 H, two s), 7.84-8.15 (3 H, m), 10.49 (1 H, br s), 11.70 and 11.78 (1 H, two s). LCMS (10 cm_esci_bicarb) Rt 2.77 min; m/z 509/511/513/515 [M+H].

Example 7

(E)-3-(4-bromophenoxy)-N'-(3,5-dibromo-4-hydroxybenzylidene)benzohydrazide (7)

$^1$H NMR δ (ppm) (DMSO-d$_6$): 7.05-7.10 (2 H, m), 7.31 (1 H, d, J=8 Hz), 7.57-7.65 (4H, m), 7.7.76 (1 H, d, J=8 Hz), 7.94 (2 H, s), 8.32 (1 H, s), 10.49 (1 H, br s), 11.99 (1 H, s). LCMS (10 cm_esci_bicarb) Rt 2.87 min; m/z 567/569/571/573 [M+H].

Example 8

(E)-3-(3-methylphenoxy)-N'-(3,5-dibromo-4-hydroxybenzylidene)benzohydrazide (8)

$^1$H NMR δ (ppm) (DMSO-d$_6$): 2.35 (3 H, s), 6.89 (1 H, d, J=12 Hz), 6.93 (1 H, s), 7.04 (1 H, d, J=4 Hz), 7.25 (1 H, d, J=4 Hz), 7.34 (1 H, t, J=8 Hz), 7.54-7.60 (2 H, m), 7.72 (1 H, d, J=8 Hz), 7.94 (2 H, s), 8.32 (1 H, s), 10.52 (1 H, br s), 12.01 (1 H, s). LCMS (10 cm_esci_bicarb) Rt 2.84 min; m/z 503/505/507 [M+H].

Example 9

(E)-4-bromo-3-chloro-N'-(3,5-dibromo-4-hydroxybenzylidene)benzohydrazide (9)

$^1$H NMR δ (ppm) (DMSO-d$_6$): 7.83 (1 H, d), 7.96 (2 H, s), 8.00 (1 H, d), 8.17 (1 H, s), 8.32 (1 H, s), 10.54 (1 H, s), 12.01 (1 H, s). LCMS (10 cm_esci_bicarb) Rt 2.75 min; m/z 509/511/513/515/517 [M+H].

Example 10

(E)-N'-(3,5-dibromo-4-hydroxybenzylidene)-2-(3,4-dichlorophenylamino)acetohydrazide (10)

$^1$H NMR δ (ppm) (DMSO-d$_6$): 3.86 and 4.30 (2 H, two s), 6.32 and 6.52 (1 H, two m), 6.64 (1 H, m), 6.81 and 6.88 (1 H, two s), 7.31 (1 H, m), 7.90 and 7.94 (2 H, two s), 7.91 and 8.11 (1 H, two s), 10.43 (1 H, s), 11.55 and 11.58 (1 H, two s). LCMS (10 cm_esci_bicarb) Rt 2.65 min; m/z 494/496/498/500/502 [M+H].

Example 11

(E)-2-(4-(1H-pyrrol-1-yl)phenoxy)-N'-(3,5-dibromo-4-hydroxybenzylidene)acetohydrazide (11)

$^1$H NMR δ (ppm) (DMSO-d$_6$): 4.73 and 5.23 (2 H, two s), 6.26 (2 H, q, J=2.1 Hz), 7.00-7.13 (2 H, m), 7.29 (2 H, m), 7.46-7.58 (2 H, m), 7.91 and 7.95 (2 H, two s), 8.22 (1 H, s), 11.68 and 11.74 (1 H, two s). LCMS (10 cm_apci_formic) Rt 3.7 min; m/z 492/494/496 [M+H].

Example 12

(E)-2-(4-bromo-3,5-dimethylphenoxy)-N'-(3,5-dibromo-4-hydroxybenzylidene)acetohydrazide (12)

$^1$H NMR δ (ppm) (DMSO-d$_6$): 2.35 (6 H, s), 4.67 and 5.17 (2 H, two s), 6.84 (1 H, s), 6.89 (1 H, s), 7.87-7.95 (2 H, m), 8.20 (1 H, s), 11.62 and 11.66 (1 H, two s). LCMS (10 cm_apci_formic) Rt 4.12 min; m/z 533/535/537/539 [M+H].

Example 13

(E)-2-(6-bromonaphthalene-2-yloxy)-N'-(3,5-dibromo-4-hydroxybenzylidene)acetohydrazide (13)

$^1$H NMR δ (ppm) (DMSO-d$_6$): 4.80 and 5.30 (2H, two s), 7.28-7.36 (2H, m), 7.54-7.60 (1H, m), 7.77-8.19 (6H, m), 10.43 (1H, br s), 11.67 and 11.74 (1H, two s). LCMS (10 cm_esci_bicarb) Rt 2.88 min; m/z 555/557/559/561 [M+H].

Example 14

(E)-N'-(3,5-dibromo-4-hydroxybenzylidene)-3-(4-fluoro-3-methoxyphenoxy)benzohydrazide (14)

$^1$H NMR δ (ppm) (DMSO-d$_6$): 3.86 (3 H, s), 6.59-6.65 (1 H, m), 7.01 (1 H, dd, J=8 and 4 Hz), 7.22-7.32 (2 H, m), 7.54-7.60 (2 H, m), 7.71 (1 H, d, J=4 Hz), 7.94 (2 H, s), 8.33 (1 H, s), 10.49 (1 H, br s), 11.99 (1 H, s). LCMS (10 cm_esci_bicarb) Rt 2.76 min; m/z 537/539/541 [M+H].

Example 15

(E)-N-allyl-N'-(3,5-dibromo-4-hydroxybenzylidene)-3-phenoxybenzohydrazide (15)

$^1$H NMR δ (ppm) (DMSO-d$_6$): 4.74 (2 H, s), 5.12-5.25 (2 H, m), 5.84-5.95 (1 H, m), 7.12 (2 H, d, J=8.0 Hz), 7.14-7.25 (3 H, m), 7.36-7.44 (3 H, m), 7.53 (1 H, t, J=7.8 Hz), 7.68 (2 H, s), 7.85 (1 H, s), 10.42 (1 H, s). LCMS (10 cm_apci_formic) Rt 4.39 min; m/z 529/531/533 [M+H].

Example 16

(E)-N'-(1-(3,5-dibromo-4-hydroxyphenyl)ethylidene)-3-phenoxybenzohydrazide (16)

$^1$H NMR δ (ppm) (DMSO-d$_6$): 2.34 (3H, s), 7.11 (2H, d), 7.21-7.26 (2H, m), 7.47-7.54 (4H, m), 7.68 (2H, s), 8.03 (1H, s), 10.37 (1H, s), 10.86 (1H, s). LCMS (10 cm_esci_bicarb) Rt 2.8 min; m/z 503/505/507 [M+H].

Example 17

(E)-N'-(4-hydroxy-3,5-diiodobenzylidene)-3-phenoxybenzohydrazide (17)

$^1$H NMR δ (ppm) (DMSO-d$_6$): 7.11 (2 H, d, J=8.00 Hz), 7.20-7.29 (2 H, m), 7.47 (2 H, t, J=7.74 Hz), 7.54-7.61 (2 H, m), 7.72 (1 H, d, J=7.77 Hz), 8.13 (2 H, s), 8.27 (1 H, s), 10.05 (1 H, br s), 11.97 (1 H, s). LCMS (10 cm_apci_formic) Rt 3.99 min; m/z 585 [M+H].

Example 18

(E)-N'-(3,5-dibromo-4-hydroxybenzylidene)-3-(3-(trifluoromethyl)phenoxy)benzohydrazide (18)

$^1$H NMR δ (ppm) (DMSO-d$_6$): 7.34-7.44 (3 H, m), 7.58 (1 H, d, J=8 Hz), 7.61-7.73 (3H, m), 7.81 (1 H, d, J=8 Hz), 7.94 (2 H, s), 8.32 (1 H, s), 10.50 (1 H, br s), 12.01 (1 H, s). LCMS (10 cm_esci_bicarb) Rt 2.9 min; m/z 557/559/561 [M+H].

Example 19

(E)-3-(benzyloxy)-N'-(3,5-dibromo-4-hydroxybenzylidene)benzohydrazide (19)

$^1$H NMR δ (ppm) (DMSO-d$_6$): 5.22 (2 H, s), 7.29 (1 H, d, J=8.07 Hz), 7.35-7.59 (8 H, m), 7.94 (2 H, s), 8.34 (1 H, s), 10.48 (1 H, s), 11.93 (1 H, s). LCMS (10 cm_esci_bicarb) Rt 2.76 min; m/z 503/505/507 [M+H].

Example 20

(E)-N'-(3,5-dibromo-4-hydroxybenzylidene)-3-phenoxybenzohydrazide (20)

$^1$H NMR δ (ppm) (DMSO-d$_6$): 7.11 (2 H, d, J=7.8 Hz), 7.21-7.28 (2 H, m), 7.47 (2 H, t, J=7.8 Hz), 7.58 (2 H, m), 7.73 (1 H, d, J=7.7 Hz), 7.94 (2 H, s), 8.32 (1 H, s), 10.49 (1 H, br s), 11.98 (1 H, s). LCMS (10 cm_apci_formic) Rt 3.65 min; m/z 489/491/493 [M+H].

Example 21

(E)-N'-(3,5-dichloro-4-hydroxybenzylidene)-3-phenoxybenzohydrazide (21)

$^1$H NMR δ (ppm) (DMSO-d$_6$): 7.11 (2 H, d, J=8.02 Hz), 7.20-7.30 (2 H, m), 7.47 (2 H, t, J=7.70 Hz), 7.58 (3 H, t, J=6.36 Hz), 7.73 (1 H, d, J=7.71 Hz), 7.76 (2 H, s), 8.34 (1 H, br s), 12.00 (1 H, s). LCMS (10 cm_apci_formic) Rt 3.77 min; m/z 401/403/405 [M+H].

Example 22

(E)-1-(3-chloro-5-(trifluoromethyl)pyridin-2-yl)-N'-(3,5-dibromo-4-hydroxybenzylidene)piperidine-4-carbohydrazide (22)

$^1$H NMR δ (ppm) (DMSO-d$_6$): 1.74-1.91 (4 H, m), 2.99 and 3.12 (2 H, two t, J=12.2 Hz), 3.37-3.49 (1 H, m), 4.08 (2 H, m), 7.87-8.09 (3 H, m), 8.17 and 8.19 (1 H, two d, J=2.2 Hz), 8.57 (1 H, s), 10.40 (1 H, s), 11.30 and 11.53 (1 H, two s). LCMS (10 cm_esci_bicarb) Rt 2.91 min; m/z 583/585/587/589 [M+H].

Example 23

(E)-2-((4-chlorophenyl)(methyl)amino)-N'-(3,5-dibromo-4-hydroxybenzylidene)acetohydrazide (23)

$^1$H NMR δ (ppm) (DMSO-d$_6$): 3.03 (3 H, s), 4.11 and 4.60 (2 H, two s), 6.70 (2 H, t, J=8.7 Hz), 7.20 (2 H, dd, J=16.1, 8.6 Hz), 7.89 and 7.93 (2 H, two s), 7.93 and 8.13 (1 H, two s), 11.50 and 11.54 (1 H, two s). LCMS (10 cm_esci_bicarb) Rt 2.61 min; m/z 474/476/478/480 [M+H].

Example 24

(E)-N'-(3,5-dibromo-4-hydroxybenzylidene)-2-p-tolylquinoline-4-carbohydrazide (24)

$^1$H NMR δ (ppm) (DMSO-d$_6$): 2.45 (3 H, s), 7.43 (3 H, d, J=8.14 Hz), 7.62-7.73 (1 H, m), 7.83-7.91 (1 H, m), 8.02 (2 H, s), 8.15-8.26 (3 H, m), 8.24-8.38 (4 H, m), 10.35 (1 H, br s), 12.34 and 12.42 (1 H, two s). LCMS (10 cm_esci_bicarb) Rt 2.77 min; m/z 538/540/542 [M+H].

Example 25

(E)-N'-(3,5-dibromo-4-hydroxybenzylidene)-3-(3,4-dichlorophenoxy)benzohydrazide (25)

$^1$H NMR δ (ppm) (DMSO-d$_6$): 7.08-7.11 (1 H, m), 7.33-7.38 (1 H, m), 7.41 (1 H, d, J=4 Hz), 7.59-7.65 (2 H, m), 7.68-7.71 (1 H, m), 7.78-7.81 (1 H, m), 7.95 (2 H, s), 8.33 (1 H, s), 10.50 (1 H, br s), 11.99 (1 H, s). LCMS (10 cm_esci_bicarb) Rt 2.98 min; m/z 557/559/561/563 [M+H].

Example 26

(E)-2-(4-bromophenyl)-N'-(3,5-dibromo-4-hydroxybenzylidene)quinoline-4-carbohydrazide (26)

$^1$H NMR δ (ppm) (DMSO-$d_6$): 7.37-8.41 (11 H, m), 10.55 (1 H, br s), 12.37 and 12.47 (1 H, two s). LCMS (10 cm_esci_bicarb) Rt 2.89 min; m/z 602/604/606/608 [M+H].

Example 27

(E)-N'-(3,5-dibromo-4-hydroxybenzylidene)-2'-fluorobiphenyl-4-carbohydrazide (27)

$^1$H NMR δ (ppm) (DMSO-$d_6$): 7.35-7.42 (2 H, m), 7.48-7.55 (1 H, m), 7.64 (1 H, td, J=7.9, 1.8 Hz), 7.75 (2 H, d, J=7.9 Hz), 7.97 (2 H, s), 8.05 (2 H, d, J=8.0 Hz), 8.36 (1 H, s), 10.48 (1 H, s), 12.05 (1 H, s). LCMS (10 cm_esci_bicarb) Rt 2.73 min; m/z 491/493/495 [M+H].

Example 28

(E)-N'-(3,5-dibromo-4-hydroxybenzylidene)-2-(4-ethoxyphenyl)quinoline-4-carbohydrazide (28)

$^1$H NMR δ (ppm) (DMSO-$d_6$): 1.41 (3 H, m), 4.11-4.20 (2 H, m), 7.14 (2 H, m), 7.46-8.50 (10 H, m), 10.52 (1 H, br s), 12.36 and 12.44 (1 H, two s). LCMS (10 cm_esci_bicarb) Rt 2.72 min; m/z 568/570/572 [M+H].

Example 29

(E)-2-(4-chloro-3-(trifluoromethyl)phenylamino)-N'-(3,5-dibromo-4-hydroxybenzylidene)acetohydrazide (29)

$^1$H NMR δ (ppm) (DMSO-$d_6$): 3.92 and 4.36 (2H, two d), 6.57 and 6.72 (1H, two s), 6.84-6.91 (1H, m), 7.07-7.11 (1H, m), 7.37-7.43 (1H, m), 7.92-8.12 (3H, m), 10.44 (1H, s), 11.75 (1H, s). LCMS (10 cm_apci_formic) Rt 3.9 min; m/z 528/530/532/534 [M+H].

Example 30

(E)-N'-(3,5-dibromo-4-hydroxybenzylidene)-2-(2,4-dichlorophenylamino)acetohydrazide (30)

$^1$H NMR δ (ppm) (DMSO-$d_6$): 3.97 and 4.39 (2H, two s), 5.72 and 5.91 (1H, two s), 6.61 and 6.74 (1H, two d), 7.23-7.25 (2H,m), 7.86-8.12 (3H, m), 10.43 (1H, s), 11.75 (1H, s). LCMS (10 cm_apci_formic) Rt 4.02 min; m/z 494/496/498/500 [M+H].

Example 31

(E)-3-(3-chloro-4-ethoxyphenoxy)-N'-(3,5-dibromo-4-hydroxybenzylidene)benzohydrazide (30)

$^1$H NMR δ (ppm) (DMSO-$d_6$): 1.39 (3 H, t, J=8 Hz), 4.15 (2 H, q, J=8 Hz), 7.08 (1 H, dd, J=8 and 4 Hz), 7.17-7.30 (3 H, m), 7.51-7.59 (2 H, m), 7.70 (1 H, d, J=8 Hz), 7.94 (2 H, s), 8.32 (1 H, s), 10.52 (1 H, br s), 12.01 (1 H, s). LCMS (10 cm_esci_bicarb) Rt 2.73 min; m/z 567/569/571/573 [M+H].

Example 32

(E)-3-bromo-4-chloro-N'-(3,5-dibromo-4-hydroxybenzylidene)benzohydrazide (32)

$^1$H NMR δ (ppm) (DMSO-$d_6$): 12.09 (1 H, s), 10.51 (1 H, s), 8.32 (2 H, d, J=2.61 Hz), 8.00-7.93 (3 H, m), 7.85 (1 H, d, J=8.40 Hz). LCMS (10 cm_esci_bicarb) Rt 2.64 min; m/z 509/511/513/515/517 [M+H].

Example 33

(E)-N'-(1-(3,5-dibromo-4-hydroxyphenyl)ethylidene)-2-(10H-phenothiazine-10-yl)acetohydrazide (33)

$^1$H NMR δ (ppm) (DMSO-$d_6$): 2.34 (3H, s), 4.74 and 5.08 (2H, two s), 6.67 (2H, d), 6.93-6.6.97 (2H, m), 7.12-7.14 (4H, m), 8.01-8.05 (2H, m). LCMS (10 cm_esci_bicarb) Rt 3.02 min; m/z 546/548/550 [M+H].

Example 34

(E)-N'-(3,5-dibromo-4-hydroxybenzylidene)-2-(naphthalen-1-yl)acetohydrazide (34)

$^1$H NMR δ (ppm) (DMSO-$d_6$): 4.07 and 4.48 (2 H, two s), 7.48-7.60 (4H, m), 7.86-8.15 (6 H, m), 10.34 (1 H, br s), 11.49 and 11.78 (1 H, two s). LCMS (10 cm_apci_formic) Rt 3.57 min; m/z 461/463/465 [M+H].

Example 35

(E)-N'-(3-bromo-4-hydroxy-5-iodobenzylidene)-3-phenoxybenzohydrazide (35)

$^1$H NMR δ (ppm) (DMSO-$d_6$): 11.98 (1 H, s), 10.35 (1 H, s), 8.30 (1 H, s), 8.13 (1 H, s), 7.93 (1 H, s), 7.73 (1 H, d), 7.60-7.56 (2 H, m), 7.47 (2 H, t), 7.28-7.18 (2 H, m), 7.11 (2 H, d). LCMS (10 cm_apci_formic) Rt 3.93 min; m/z 537/539/541 [M+H].

Example 36

(E)-N'-(3,5-dibromo-4-hydroxybenzylidene)-3-(3,4,5-trifluorophenoxy)benzohydrazide (36)

$^1$H NMR δ (ppm) (DMSO-$d_6$): 7.15-7.21 (2 H, m), 7.35 (1 H, d, J=4 Hz), 7.59-7.65 (2H, m), 7.80 (1 H, d, J=8 Hz), 7.95 (2 H, s), 8.33 (1 H, s), 10.49 (1 H, br s), 12.00 (1 H, s). LCMS (10 cm_esci_bicarb) Rt 2.66 min; m/z 543/545/547 [M+H].

Example 37

(E)-3-(3,5-bis(trifluoromethyl)phenoxy)-N'-(3,5-dibromo-4-hydroxybenzylidene)benzohydrazide (37)

$^1$H NMR δ (ppm) (DMSO-$d_6$): 7.45 (1 H, dd, J=8 and 4 Hz), 7.67 (1 H, t, J=8 Hz), 7.74-7.76 (3 H, m), 7.86 (1 H, d, J=8 Hz), 7.94-7.96 (3 H, m), 8.32 (1 H, s), 10.51 (1 H, br s), 12.03 (1 H, s). LCMS (10 cm_esci_bicarb) Rt 2.89 min; m/z 625/627/629 [M+H].

Example 38

(E)-N'-(3-bromo-5-chloro-4-hydroxybenzylidene)-3-phenoxybenzohydrazide (38)

$^1$H NMR δ (ppm) (DMSO-d$_6$): 12.00 (1 H, s), 8.33 (1 H, s), 7.91 (1 H, d, J=2.00 Hz), 7.79 (1 H, s), 7.73 (1 H, d, J=7.79 Hz), 7.58 (2 H, t, J=4.85 Hz), 7.47 (2 H, t, J=7.73 Hz), 7.30-7.20 (2 H, m), 7.11 (2 H, d, J=8.00 Hz). LCMS (10 cm_apci_formic) Rt 3.8 min; m/z 445/447/449 [M+H]

Example 39

(E)-8-chloro-N'-(3,5-dibromo-4-hydroxybenzylidene)-2-phenylquinoline-4-carbohydrazide (39)

$^1$H NMR δ (ppm) (DMSO-d$_6$): 7.38-8.58 (12 H, m), 12.38 and 12.49 (1 H, two s). LCMS (10 cm_apci_formic) Rt 4.25 min; m/z 558/560/562/564 [M+H].

Example 40

(E)-2-(4-chlorophenylamino)-N'-(3,5-dibromo-4-hydroxybenzylidene)acetohydrazide (40)

$^1$H NMR δ (ppm) (DMSO-d$_6$): 3.83 and 4.26 (2 H, s), 6.02 and 6.26 (1 H, two br s), 6.61-6.68 (2 H, m), 7.12-7.16 (2H, m), 7.94-7.90 (2 H, m), 8.06 and 8.12 (1 H, two s), 10.45 (1 H, br s), 11.53 and 11.55 (1 H, two s). LCMS (10 cm_apci_formic) Rt 3.48 min; m/z 460/462/464/466 [M+H].

Example 41

(E)-2-(4-chlorophenyl)-N'-(3,5-dichloro-4-hydroxybenzylidene)quinoline-4-carbohydrazide (41)

$^1$H NMR δ (ppm) (DMSO-d$_6$): 12.34 (1 H, s), 8.46-8.37 (3 H, m), 8.30-8.17 (3 H, m), 7.97-7.79 (3 H, m), 7.79-7.63 (3 H, m). LCMS (10 cm_esci_bicarb) Rt 2.93 min; m/z 470/472/474/476 [M+H].

Example 42

(E)-2-(4-chlorophenyl)-N'-(3,5-dibromo-4-hydroxybenzylidene)quinoline-4-carbohydrazide (42)

$^1$H NMR δ (ppm) (DMSO-d$_6$): 7.63-7.77 (4 H, m), 7.85-7.94 (1 H, m), 8.01 (2 H, s), 8.17-8.31 (3 H, m), 8.36-8.47 (3 H, m), 12.35 and 12.45 (1 H, two s). LCMS (10 cm_esci_bicarb) Rt 2.85 min; m/z 558/560/562/564 [M+H].

Example 43

(E)-N'-(3,5-dibromo-4-hydroxybenzylidene)-2-(2,3-dichlorophenylamino)acetohydrazide (43)

$^1$H NMR δ (ppm) (DMSO-d$_6$): 3.99 and 4.41 (2H, two d), 5.89 and 6.08 (1H, two s), 6.57 and 6.70 (1H, two d), 6.86-7.21 (2H, m), 7.91-8.12 (3H, m), 10.34 (1H, s), 11.75 (1H, s). LCMS (10 cm_apci_formic) Rt 3.96 min; m/z 494/496/498/500 [M+H].

Example 44

(E)-N'-(3,5-dibromo-4-hydroxybenzylidene)-2-(4-methoxyphenyl)quinoline-4-carbohydrazide (44)

$^1$H NMR δ (ppm) (DMSO-d$_6$): 3.90 (3 H, s), 7.17 (2 H, d, J=8.79 Hz), 7.61-7.71 (1 H, m), 7.81-7.90 (1 H, m), 8.01 (2 H, s), 8.13-8.23 (2 H, m), 8.26 (1 H, s), 8.32 (1 H, s), 8.37 (2 H, d, J=8.68 Hz), 10.54 (1 H, s), 12.34 (1 H, s). LCMS (10 cm_esci_bicarb) Rt 2.66 min; m/z 554/556/558 [M+H].

Example 45

(E)-N'-(3,5-dibromo-4-hydroxybenzylidene)-3-(4-methoxy-3-methylphenoxy)benzohydrazide (45)

$^1$H NMR δ (ppm) (DMSO-d$_6$): 2.19 (3 H, s), 3.83 (3 H, s), 6.92-7.03 (3 H, m), 7.16 (1 H, d, J=8 Hz), 7.47 (1 H, s), 7.52 (1 H, t, J=8 Hz), 7.64 (1H, d, J=8 Hz), 7.94 (2 H, s), 8.32 (1 H, s), 10.51 (1 H, br s), 12.00 (1 H, s). LCMS (10 cm_esci_bicarb) Rt 2.64 min; m/z 533/535/537 [M+H].

Example 46

(E)-3-benzyl-N'-(3,5-dibromo-4-hydroxybenzylidene)benzohydrazide (46)

$^1$H NMR δ (ppm) (DMSO-d$_6$): 4.07 (2 H, s), 7.23-7.35 (5 H, m), 7.49 (2 H, s), 7.77 (1 H, s), 7.82 (1 H, s), 7.94 (2 H, s), 8.33 (1 H, s), 10.50 (1 H, br s), 11.98 (1 H, s). LCMS (10 cm_esci_bicarb) Rt 2.61 min; m/z 487/489/491 [M+H].

Example 47

(E)-3'-((2-(2-hydroxy-2,2-diphenylacetyl)hydrazono)methyl)biphenyl-3-carboxylic acid (47)

$^1$H NMR δ (ppm) (DMSO-d$_6$): 1.27 (9 H, s), 5.23 (2 H, s), 7.11-7.14 (2 H, m), 7.15-7.20 (2 H, m), 7.25 (1 H, ddd, J=8.2, 2.6, 1.0 Hz), 7.35-7.42 (3 H, m), 7.54 (1 H, t, J=7.9 Hz), 7.58 (1 H, s), 7.66 (2 H, s), 10.43 (1 H, s). LCMS (10 cm_apci_formic) Rt 3.6 min; m/z 449 [M−H].

Example 48

(E)-N'-(3,5-dichloro-4-hydroxybenzylidene)-2-(10H-phenothiazine-10-yl)acetohydrazide (48)

$^1$H NMR δ (ppm) (DMSO-d$_6$): 11.95 and 11.77 (1 H, two s), 8.16 and 7.99 (1 H, two s), 7.79 (2 H, d, J=16.73 Hz), 7.20-7.08 (4 H, m), 7.01-6.91 (2 H, m), 6.77 (1 H, d, J=8.18 Hz), 6.68 (2 H, d, J=8.18 Hz), 5.05 and 4.62 (2 H, two s). LCMS (10 cm_esci_bicarb) Rt 2.85 min; m/z 444/446/448 [M+H].

Example 49

(E)-N'-(3,5-dibromo-4-hydroxybenzylidene)-2-(thiophen-2-yl)quinoline-4-carbohydrazide (49)

$^1$H NMR δ (ppm) (DMSO-d$_6$): 7.18-8.35 (11 H, m), 10.54 (1 H, br s), 12.38 and 12.47 (1 H, two s). LCMS (10 cm_esci_bicarb) Rt 2.63 min; m/z 530/532/534 [M+H].

Example 50

(E)-N'-(3,5-dibromo-4-hydroxybenzylidene)-2-(10H-phenothiazine-10-yl)acetohydrazide (50)

$^1$H NMR δ (ppm) (DMSO-d$_6$): 4.62 and 5.04 (2 H, two s), 6.65 and 6.77 (2 H, two d, J=8.2 Hz), 6.91-6.99 (2 H, m), 7.08-7.20 (4 H, m), 7.96-8.09 (3 H, m), 9.43 (1 H, br s), 11.76 and 11.95 (1 H, two s). LCMS (10 cm_esci_bicarb) Rt 2.88 min; m/z 532/534/536 [M+H].

Example 51

(E)-N'-(1-(3,5-dichloro-4-hydroxyphenyl)ethylidene)-3-phenoxybenzohydrazide (51)

$^1$H NMR δ (ppm) (DMSO-d$_6$): 2.34 (3 H, s), 7.11 (2 H, d, J=8.0 Hz), 7.22-7.27 (2 H, m), 7.32-7.91 (7 H, m), 10.62 (1 H, s), 10.87 (1 H, s). LCMS (10 cm_apci_formic) Rt 3.89 min; m/z 415/417/419 [M+H].

Example 52

(E)-2-(4-chlorophenyl)-N'-(4-hydroxy-3,5-diiodobenzylidene)quinoline-4-carbohydrazide (52)

$^1$H NMR δ (ppm) (DMSO-d$_6$): 12.31 (1 H, s), 8.47-8.35 (3 H, m), 8.28-8.17 (4 H, m), 7.97-7.85 (2 H, m), 7.77-7.64 (3 H, m). LCMS (10 cm_esci_bicarb) Rt 3.04 min; m/z 654/656 [M+H].

Example 53

(E)-3-(3-acetylphenoxy)-N'-(3,5-dibromo-4-hydroxybenzylidene)benzohydrazide (53)

$^1$H NMR δ (ppm) (DMSO-d$_6$): 2.62 (3 H, s), 7.32 (1 H, dd, J=8 and 4 Hz), 7.39 (1 H, dd, J=8 and 4 Hz), 7.57-7.66 (4 H, m), 7.78 (1 H, d, J=8 Hz), 7.83 (1 H, d, J=8 Hz), 7.94 (2 H, s), 8.33 (1 H, s), 10.50 (1 H, br s), 12.01 (1 H, s). LCMS (10 cm_esci_bicarb) Rt 2.56 min; m/z 531/533/535 [M+H].

Example 54

(E)-N'-(3,5-dibromo-4-hydroxybenzylidene)-3-(3-(trifluoromethoxy)phenoxy)benzohydrazide (54)

$^1$H NMR δ (ppm) (DMSO-d$_6$): 7.08-7.13 (2 H, m), 7.22 (1 H, d, J=8 Hz), 7.36 (1 H, d, J=8 Hz), 7.55-7.67 (3 H, m), 7.80 (1 H, d, J=8 Hz), 7.94 (2 H, s), 8.32 (1 H, s), 10.48 (1 H, br s), 12.00 (1 H, s). LCMS (10 cm_esci_bicarb) Rt 2.96 min; m/z 573/575/577 [M+H].

Example 55

(E)-N'-(3,5-dibromo-4-hydroxybenzylidene)-3-(2,3-dihydrobenzo[b][1,4]dioxin-6-yloxy)benzohydrazide (55)

$^1$H NMR δ (ppm) (DMSO-d$_6$): 4.27-4.31 (4 H, m), 6.58-6.68 (2 H, m), 6.94 (1 H, d, J=8 Hz), 7.19 (1 H, d, J=8 Hz), 7.45-7.56 (2 H, m), 7.66 (1 H, d, J=8 Hz), 7.93 (2 H, s), 8.32 (1H, s), 10.51 (1 H, br s), 12.00 (1 H, s). LCMS (10 cm_esci_bicarb) Rt 2.5 min; m/z 547/549/551 [M+H].

Example 56

(E)-N'-(4-hydroxy-3,5-diiodobenzylidene)-2-(10H-phenothiazine-10-yl)acetohydrazide (56)

$^1$H NMR δ (ppm) (DMSO-d$_6$): 11.91 and 11.72 (1 H, two s), 8.17-8.07 (2 H, m), 7.94 (1H, s), 7.19-7.09 (4 H, m), 6.96 (2 H, dt, J=11.01, 7.48 Hz), 6.77 (1 H, d, J=8.17 Hz), 6.67 (2H, d, J=8.16 Hz), 5.03 and 4.61 (2 H, two s). LCMS (10 cm_esci_bicarb) Rt 2.98 min; m/z 628 [M+H].

Example 57

(E)-N'-(1-(3,5-dichloro-4-hydroxyphenyl)ethylidene)-2-(10H-phenothiazine-10-yl)acetohydrazide (57)

$^1$H NMR δ (ppm) (DMSO-d$_6$): 5.42 (2 H, s), 7.10-7.15 (2 H, m), 7.18 (1 H, t, J=7.4 Hz), 7.24 (1 H, ddd, J=8.0, 2.6, 1.2 Hz), 7.30 (1 H, t, J=1.8 Hz), 7.37-7.42 (2 H, m), 7.48-7.59 (4 H, m), 7.62 (2 H, s), 7.85-7.92 (3 H, m), 8.25 (1 H, s), 9.29 (1 H, s), 10.42 (1 H, s). LCMS (10 cm_apci_formic) Rt 4.19 min; m/z 458/460/462 [M+H].

Example 58

(E)-N'-(1-(3,5-dibromo-4-hydroxyphenyl)-2-phenylethylidene)-3-phenoxybenzohydrazide (59)

$^1$H NMR δ (ppm) (DMSO-d$_6$): 5.37 (2 H, s), 7.13 (2 H, dd, J=8.1, 1.2 Hz), 7.18 (1 H, t, J=7.4 Hz), 7.18-7.40 (9 H, m), 7.46-7.49 (1 H, m), 7.56 (1 H, t, J=7.9 Hz), 7.61 (2 H, s), 7.87 (1 H, s), 10.43 (1 H, s). LCMS (10 cm_apci_formic) Rt 4.57 min; m/z 579/581/583 [M+H].

Example 59

(E)-3-benzoyl-N'-(3,5-dibromo-4-hydroxybenzylidene)benzohydrazide (60)

$^1$H NMR δ (ppm) (DMSO-d$_6$): 7.54-7.67 (2 H, m), 7.74-7.85 (4 H, m), 7.96-7.99 (3 H, m), 8.24 (1 H, d, J=8 Hz), 8.30 (1 H, s), 8.34 (1 H, s), 10.50 (1 H, br s). LCMS (10 cm_esci_bicarb) Rt 2.53 min; m/z 501/503/505 [M+H].

Example 60

(E)-N'-(3,5-dibromo-4-hydroxybenzylidene)-3-(4-methoxyphenoxy)benzohydrazide (61)

$^1$H NMR δ (ppm) (DMSO-d$_6$): 3.78 (3 H, s), 7.00 (2 H, d, J=12 Hz), 7.06 (2 H, d, J=12 Hz), 7.16-7.18 (1 H, m), 7.48 (1 H, s), 7.53 (1 H, t, J=8 Hz), 7.65 (1 H, d, J=4 Hz), 7.92 (2 H, s), 8.32 (1 H, s), 10.45 (1 H, br s), 11.96 (1 H, s). LCMS (10 cm_esci_bicarb) Rt 2.75 min; m/z 519/521/523 [M+H].

Example 61

(E)-3-chloro-N'-(3,5-dibromo-4-hydroxy benzylidene)-6-methoxybenzo[b]thiophene-2-carbohydrazide (62)

$^1$H NMR δ (ppm) (378.2 K, DMSO-d$_6$): 3.95 (3 H, s), 7.25 (1 H, d), 7.65 (1 H, s), 7.86 (1 H, d), 7.91 (2 H, s), 8.31 (1 H, s), 8.28 (1 H, s), 9.95 (1 H, br s), 11.56 (1 H, s). LCMS (10 cm_esci_bicarb) Rt 2.66 min; m/z 517/519/521/523 [M+H].

Example 62

(E)-N'-(3,5-dibromo-4-hydroxybenzylidene)-4-phenoxybenzohydrazide (63)

$^1$H NMR δ (ppm) (DMSO-d$_6$): 7.08-7.22 (4 H, m), 7.26 (1 H, t), 7.44-7.49 (2 H, m), 7.92-7.96 (4 H, m), 8.29 (1 H, s), 10.46 (1 H, s), 11.90 (1 H, s). LCMS (10 cm_esci_bicarb) Rt 2.71 min; m/z 489/491/493 [M+H].

Example 63

(E)-N-(4-tert-butylbenzyl)-N'-(3,5-dibromo-4-hydroxybenzylidene)-3-phenoxybenzohydrazide (64)

$^1$H NMR δ (ppm) (DMSO-d$_6$): 1.28 (9 H, s), 5.32 (2 H, s), 7.12 (2 H, d, J=7.99 Hz), 7.15-7.30 (5 H, m), 7.34-7.44 (4 H, m), 7.44-7.49 (1 H, m), 7.55 (1 H, t, J=7.8 Hz), 7.63 (2 H, s), 7.91 (1 H, s), 10.43 (1 H, s). LCMS (10 cm_apci_formic) Rt 5.08 min; m/z 635/637/639 [M+H].

Example 64

(E)-N'-(3,5-dibromo-4-hydroxybenzylidene)-2-(5-methyl-2-phenylthiazol-4-yl)acetohydrazide (65)

$^1$H NMR δ (ppm) (DMSO-d$_6$): 2.48 and 2.50 (3 H, two s), 3.75 and 4.14 (2 H, two s), 7.42-7.53 (3 H, m), 7.83-7.89 (2 H, m), 7.86-8.14 (3 H, m), 10.40 (1 H, br s), 11.49 and 11.74 (1H, two s). LCMS (10 cm_esci_bicarb) Rt 2.64 min; m/z 508/510/512 [M+H].

Example 65

(E)-2-(2-chloro-5-methylphenoxy)-N'-(3,5-dibromo-4-hydroxybenzylidene)acetohydrazide (66)

$^1$H NMR δ (ppm) (DMSO-d$_6$): 2.29 and 2.31 (3 H, two s), 4.77 and 5.30 (2 H, two s), 6.79 and 6.85 (1 H, two d, J=8.1 Hz), 6.89 and 6.94 (1 H, two s), 7.31 and 7.35 (1 H, two d, J=8.0 Hz), 7.88-8.17 (3 H, m), 10.42 (1 H, s), 11.65 and 11.67 (1 H, two s). LCMS (10 cm_esci_bicarb) Rt 2.75 min; m/z 475/477/479/481 [M+H].

Example 66

(E)-N'-(3,5-dibromo-4-hydroxybenzylidene) octanehydrazide (67)

$^1$H NMR δ (ppm) (DMSO-d$_6$): 0.85-0.91 (3 H, m), 1.31 (8 H, m), 1.56-1.64 (2 H, m), 2.21 and 2.62 (2 H, two t, J=7.4 Hz), 7.80-8.04 (3 H, m), 10.38 (1 H, br s), 11.24 and 11.40 (1H, two s). LCMS (10 cm_esci_bicarb) Rt 2.72 min; m/z 419/421/423 [M+H].

Example 67

(E)-4-(4-chlorophenylsulfonyl)-N'-(3,5-dibromo-4-hydroxybenzylidene)-3-methylthiophene-2-carbohydrazide (68)

$^1$H NMR δ (ppm) (DMSO-d$_6$): 2.41 and 2.48 (3 H, two br s), 7.78 (2 H, d, J=8.3 Hz), 7.89 (2 H, br s), 7.99 (2 H, d, J=8.5 Hz), 8.20 (1 H, br s), 8.78 and 8.89 (1 H, two br s), 10.51 (1H, s), 11.98 (1 H, br m). LCMS (10 cm_esci_bicarb) Rt 2.77 min; m/z 591/593/595/597 [M+H].

Example 68

(E)-2-(4-chlorophenylthio)-N'-(3,5-dibromo-4-hydroxybenzylidene)propanehydrazide (69)

$^1$H NMR δ (ppm) (DMSO-d$_6$): 1.45 (3 H, t, J=7.1 Hz), 3.98 and 4.86 (1 H, two q, J=7.0 Hz), 7.33-7.52 (4 H, m), 7.75 and 7.90 (2 H, two s), 7.82 and 8.08 (1 H, two s), 10.41 (1 H, br s), 11.48 and 11.68 (1 H, two s). LCMS (10 cm_esci_bicarb) Rt 2.61 min; m/z 491/493/495/497 [M+H].

Example 69

(E)-N'-(3,5-difluoro-4-hydroxybenzylidene)-3-phenoxybenzohydrazide (70)

$^1$H NMR δ (ppm) (DMSO-d$_6$): 11.93 (1 H, s), 10.79 (1 H, s), 8.36 (1 H, s), 7.73 (1 H, d, J=7.73 Hz), 7.58 (2 H, t, J=9.08 Hz), 7.51-7.40 (4 H, m), 7.30-7.20 (2 H, m), 7.11 (2 H, d, J=8.00 Hz). LCMS (10 cm_esci_bicarb) Rt 2.67 min; m/z 369 [M+H].

Example 70

(E)-3,5-dichloro-N'-(3,5-dibromo-4-hydroxybenzylidene)benzohydrazide (71)

$^1$H NMR δ (ppm) (DMSO-d$_6$): 7.86-8.01 (5 H, m), 8.32 (1 H, s), 10.53 (1 H, s), 12.12 (1H, s). LCMS (10 cm_esci_bicarb) Rt 2.66 min; m/z 465/467/469/471/473 [M+H].

Example 71

(E)-N'-(3,5-dibromo-4-hydroxybenzylidene)-N-methyl-3-phenoxybenzohydrazide (73)

$^1$H NMR δ (ppm) (DMSO-d$_6$): 3.45 (3 H, s), 7.11 (2 H, d, J=8.0 Hz), 7.15-7.23 (3 H, m), 7.36-7.41 (3 H, m), 7.52 (1 H, t, J=7.9 Hz), 7.70 (2 H, s), 7.93 (1 H, s), 10.40 (1 H, s). LCMS (10 cm_esci_bicarb) Rt 2.79 min; m/z 503/505/507 [M+H].

Example 72

(E)-3-(3-(benzyloxy)phenoxy)-N'-(3,5-dibromo-4-hydroxybenzylidene)benzohydrazide (74)

$^1$H NMR δ (ppm) (DMSO-d$_6$): 5.14 (2 H, s), 6.65 (1 H, d, J=8 Hz), 6.75 (1 H, s), 6.88 (1 H, d, J=8 Hz), 7.26 (1 H, d, J=8 Hz), 7.33-7.49 (6 H, m), 7.54-7.59 (2 H, m), 7.74 (1 H, d, J=8 Hz), 7.94 (2 H, s), 8.33 (1 H, s), 10.48 (1 H, br s), 11.99 (1 H, s). LCMS (10 cm_esci_bicarb) Rt 3.05 min; m/z 595/597/599 [M+H].

Example 73

(E)-N-(3-(3-(2-(3,5-dibromo-4-hydroxybenzylidene) hydrazinecarbonyl)phenoxy)phenyl)methanesulfonamide (75)

$^1$H NMR δ (ppm) (DMSO-d$_6$): 3.05 (3 H, s), 6.80 (1 H, d, J=8 Hz), 6.95 (1 H, t, J=4 Hz), 7.04 (1 H, d, J=12 Hz), 7.28-7.32 (1 H, m), 7.38-7.42 (1 H, m), 7.59-7.62 (2 H, m), 7.75 (1H, d, J=8 Hz), 7.92 (2 H, s), 8.30 (1 H, s), 9.95 (1 H, s), 10.51 (1 H, br s), 12.00 (1 H, br s). LCMS (10 cm_esci_bicarb) Rt 2.29 min; m/z 582/584/586 [M+H].

Example 74

(E)-2-(4-chlorophenyl)-N'-(3,5-dibromo-4-hydroxybenzylidene)isonicotinohydrazide (76)

$^1$H NMR δ (ppm) (DMSO-d$_6$): 7.65 (2H, d, J=8.6 Hz), 7.82 (1H, dd, J=1.3 and 4.9 Hz), 7.99 (2H, s), 8.23 (2H, d, J=8.6 Hz), 8.38 (2H, d, J=9.3 Hz), 8.90 (1H, d, J=5.0 Hz), 10.61

(1H, s), 12.23 (1H, s). LCMS (10 cm_apci_formic) Rt 3.86 min; m/z 508/510/512/514 [M+H].

Example 75

(E)-2-(4-(3-chloro-5-(trifluoromethyl)pyridin-2-yl)piperazin-1-yl)-N'-(3,5-dibromo-4-hydroxybenzylidene)acetohydrazide (77)

$^1$H NMR δ (ppm) (DMSO-d$_6$): 2.71 and 2.93 (4 H, two s), 3.21 and 3.85 (2 H, two s), 3.56 (4 H, s), 7.85-8.19 (3 H, m), 8.21-8.24 (1 H, m), 8.59 (1 H, s), 11.35 and 11.48 (1 H, two s). LCMS (10 cm_esci_bicarb) Rt 2.83 min; m/z 598/600/602/604 [M+H].

Example 76

(E)-N'-(3,5-dibromo-4-hydroxybenzylidene)-3-hydroxy-2-naphthohydrazide (78)

$^1$H NMR δ (ppm) (DMSO-d$_6$): 7.34-7.44 (2 H, m), 7.52-7.60 (1 H, m), 7.80 (1 H, d, J=8.34 Hz), 7.93-8.01 (3 H, m), 8.34 (1 H, s), 8.47 (1 H, s), 10.54 (1 H, s), 11.30 (1 H, s), 12.06 (1H, s). LCMS (10 cm_esci_bicarb) Rt 2.65 min; m/z 463/465/467 [M+H].

Example 77

(E)-N'-(3,5-difluoro-4-hydroxybenzylidene)-2-(10H-phenothiazine-10-yl)acetohydrazide (79)

$^1$H NMR δ (ppm) (DMSO-d$_6$): 11.90 and 11.76 (1 H, two s), 10.72 (1 H, s), 8.18 and 7.99 (1 H, two s), 7.47 (2 H, dd, J=24.40, 7.39 Hz), 7.13 (4 H, t, J=8.21 Hz), 6.95 (1 H, t, J=7.52 Hz), 6.78 (1 H, d, J=7.65 Hz), 6.69 (2 H, d, J=7.76 Hz), 5.03 and 4.61 (2 H, two s). LCMS (10 cm_esci_formic) Rt 3.73 min; m/z 410 [M−H]

Example 78

(E)-2-(4-chlorophenylamino)-N'-(3,5-dichloro-4-hydroxybenzylidene)acetohydrazide (88)

$^1$H NMR δ (ppm) (DMSO-d$_6$): 3.82 and 4.26 (2H, two s), 5.99 and 6.23 (1H, two s), 6.61-6.69 (2H, m), 7.14 (2H, m), 7.71 and 7.77 (2H, two s), 7.92 and 8.14 (1H, two s), 10.65 (1H, s), 11.54 (1H, s). LCMS (10 cm_apci_formic) Rt 3.36 min; m/z 372/374/376/378 [M+H].

Example 79

(E)-N'-(3,5-dibromo-4-hydroxybenzylidene)-2-(4-iodophenylamino)acetohydrazide (90)

$^1$H NMR δ (ppm) (DMSO-d$_6$): 3.81 and 4.25 (2H, two s), 6.03 and 6.26 (1H, two m), 6.47-6.54 (2H, m), 7.39 (2H, t), 7.90 (2H, m), 8.12 (1H, s), 10.41 (1H, s, br), 11.54 (1H, s). LCMS (10 cm_apci_formic) Rt 3.8 min; m/z 552/554/556 [M+H].

Example 80

(E)-N'-(3,5-dibromo-4-hydroxybenzylidene)-2-(4-(trifluoromethyl)phenylamino)acetohydrazide (96)

$^1$H NMR δ (ppm) (DMSO-d$_6$): 3.90 and 4.35 (2H, two d), 6.74 and 6.56 (3H, two m), 7.45-7.41 (2H, m), 8.12-7.90 (3H, m), 10.43 (1H, s), 11.65 and 11.55 (1 H, two s). LCMS (10 cm_apci_formic) Rt 3.72 min; m/z 494/496/498 [M+H].

Example 81

(E)-N'-(3,5-dibromo-4-hydroxybenzylidene)-2-(4-(trifluoromethoxy)phenylamino)acetohydrazide (99)

$^1$H NMR δ (ppm) (DMSO-d$_6$): 3.85 and 4.28 (2H, two s), 6.09 and 6.32 (1H, two m), 6.64-6.71 (2H, m), 7.09-7.13 (2H, m), 7.89-7.94 (2H, m), 8.13 (1H, s), 11.53 and 11.57 (1H, two s). LCMS (10 cm_apci_formic) Rt 3.79 min; m/z 510/512/514 [M+H].

Example 82

(E)-2-(3-chlorophenyl)-N'-(3,5-dibromo-4-hydroxybenzylidene)acetohydrazide (102)

$^1$H NMR δ (ppm) (DMSO-d$_6$): 3.60 and 4.04 (2 H, two s), 7.24-7.43 (4 H, m), 7.90-8.10 (3 H, m), 10.41 (1 H, s), 11.48 and 11.71 (1 H, two s). LCMS (10 cm_esci_bicarb) Rt 2.6 min; m/z 445/447/449/451 [M+H].

Example 83

(E)-N-(3-(2-(3,5-dibromo-4-hydroxybenzylidene)hydrazinecarbonyl)phenyl)-3-(trifluoromethyl)benzamide (103)

$^1$H NMR δ (ppm) (DMSO-d$_6$): 7.58 (1 H, t, J=7.80 Hz), 7.72 (1 H, d, J=7.71 Hz), 7.85 (1 H, t, J=7.83 Hz), 7.96 (2 H, s), 8.03 (1 H, d, J=7.93 Hz), 8.10 (1 H, d, J=7.42 Hz), 8.29-8.40 (4 H, m), 10.49 (1 H, br s), 10.70 (1 H, s), 12.01 (1 H, s). LCMS (10 cm_apci_formic) Rt 3.67 min; m/z 584/586/588 [M+H].

Example 84

(E)-2-(4-chlorophenylamino)-N'-(1-(3,5-dibromo-4-hydroxyphenyl)ethylidene) acetohydrazide (111)

$^1$H NMR δ (ppm) (DMSO-d$_6$): 2.24 (3H, s), 3.93 and 4.29 (2H, two s), 6.03 and 6.21 (1H, two s), 6.65 (2H, d), 7.14 (2H, m), 7.97 (2H, m), 10.29 (1H, s), 10.50 and 10.78 (1H, two s). LCMS (10 cm_apci_formic) Rt 3.68 min; m/z 474/476/478 [M+H].

Example 85

(E)-4-(benzyloxy)-N'-(3,5-dibromo-4-hydroxybenzylidene)benzohydrazide (112)

$^1$H NMR δ (ppm) (DMSO-d$_6$): 5.21 (2 H, s), 7.14 (2 H, d, J=... Hz), 7.33-7.47 (5 H, m), 7.92-7.96 (4 H, m), 8.28 (1 H, s), 10.46 (1 H, s), 11.80 (1 H, s). LCMS (10 cm_esci_bicarb) Rt 2.71 min; m/z 503/505/507 [M+H].

Example 86

(E)-2-(1-bromonaphthalen-2-yloxy)-N'-(3,5-dibromo-4-hydroxybenzylidene)acetohydrazide (113)

$^1$H NMR δ (ppm) (DMSO-d$_6$): 4.96 and 5.49 (2 H, two s), 7.42-7.54 (2 H, m), 7.67-7.70 (1 H, m), 7.92-8.17 (6 H, m), 10.48 (1 H, s), 11.71 (1 H, m). LCMS (10 cm_esci_bicarb) Rt 2.91 min; m/z 555/557/559/561 [M+H].

Example 87

(E)-N'-(3-bromo-4-hydroxy-5-nitrobenzylidene)-2-(4-chlorophenylamino)acetohydrazide (117)

$^1$H NMR δ (ppm) (DMSO-$d_6$): 3.91 and 4.29 (2H, two s), 4.61-4.68 (2H, m), 7.11-7.16 (2H, m), 7.94 (1H, s), 8.22-8.36 (2H, m), 11.66 (1H, s). LCMS (10 cm_apci_formic) Rt 3.65 min; m/z 427/429/431 [M+H].

Example 88

(E)-N'-(3,5-dibromo-4-hydroxybenzylidene)-2-(2,4-dichlorophenoxy)acetohydrazide (122)

$^1$H NMR δ (ppm) (DMSO-$d_6$): 4.83 and 5.36 (2 H, two s), 7.09-7.14 (1 H, m), 7.36 and 7.42 (1 H, two dd), 7.61 and 7.65 (1 H, two d), 7.90-8.14 (3 H, m), 10.46 (1H, br s), 11.72 and 11.74 (1 H, two s). LCMS (10 cm_esci_bicarb) Rt 2.7 min; m/z 495/497/499/501 [M+H].

Example 89

(E)-2-(4-bromophenoxy)-N'-(3,5-dibromo-4-hydroxybenzylidene)acetohydrazide (128)

$^1$H NMR δ (ppm) (DMSO-$d_6$): 4.67 and 5.18 (1 H, two s), 6.89-6.97 (2 H, m), 7.42-7.87 (2 H, m), 7.87-7.90 (2 H, m), 7.91 and 8.16 (1 H, two s), 10.43 (1 H, br s), 11.55 and 11.60 (1 H, two s). LCMS (10 cm_esci_bicarb) Rt 2.6 min; m/z 505/507/509/511 [M+H].

Example 90

(E)-3-chloro-N'-(3,5-dibromo-4-hydroxybenzylidene)benzo[b]thiophene-2-carbohydrazide (159)

$^1$H NMR δ (ppm) (DMSO-$d_6$): 7.64-7.69 (2 H, m), 7.86-8.33 (5 H, m), 10.52 (1 H, s), 12.12 and 12.27 (1 H, two s). LCMS (10 cm_esci_bicarb) Rt 2.68 min; m/z 487/489/491/493 [M+H].

Example 91

(E)-N'-(3,5-dibromo-4-hydroxybenzylidene)-3-(o-tolyloxy)benzohydrazide (160)

$^1$H NMR δ (ppm) (DMSO-$d_6$): 2.23 (3 H, s), 7.00 (1 H, d, J=8 Hz), 7.12 (1 H, d, J=8 Hz), 7.19 (1 H, t, J=8 Hz), 7.29 (1 H, t, J=4 Hz), 7.40 (1 H, d, J=8 Hz), 7.47 (1 H, s), 7.54 (1H, t, J=8 Hz), 7.66 (1 H, d, J=4 Hz), 7.94 (2 H, s), 8.33 (1 H, s), 10.49 (1 H, br s), 11.99 (1 H, s). LCMS (10 cm_esci_bicarb) Rt 2.8 min; m/z 503/505/507 [M+H].

Example 92

(E)-3-tert-butyl-N'-(3,5-dibromo-4-hydroxybenzylidene)-1-(2,4-dichlorobenzyl)-1H-pyrazole-5-carbohydrazide (161)

$^1$H NMR δ (ppm) (DMSO-$d_6$): 1.33 (9 H, s), 5.79 (2 H, s), 6.48 (1 H, d, J=8.41 Hz), 7.06 (1 H, s), 7.38 (1 H, dd, J=8.41, 2.16 Hz), 7.68 (1 H, d, J=2.13 Hz), 7.83-7.95 (2 H, m), 8.26 (1 H, s), 10.49 (1 H, s), 11.97 (1 H, s). LCMS (10 cm_esci_bicarb) Rt 3.26 min; m/z 601/603/605/607 [M+H].

Example 93

(E)-2-(4-chlorophenyl)-N'-(3,5-dibromo-2,4-dihydroxybenzylidene)quinoline-4-carbohydrazide (162)

$^1$H NMR δ (ppm) (DMSO-$d_6$): 7.65-7.77 (3 H, m), 7.85 (1 H, s), 7.89-7.95 (1 H, m), 8.22 (1 H, d, J=8.6 Hz), 8.28 (1 H, d, J=8.4 Hz), 8.40-8.48 (4 H, m), 10.51 (1H, br s), 12.72 (2H, s). LCMS (10 cm_apci_formic) Rt 4.32 min; m/z 572/574/576/578 [M+H].

Example 94

(E)-N'-(3,5-dibromo-4-hydroxybenzylidene)-3-iodobenzohydrazide (163)

$^1$H NMR δ (ppm) (DMSO-$d_6$): 7.37 (1 H, t, J=7.8 Hz), 7.90-8.04 (4 H, m), 8.27 and 8.32 (2 H, two s), 10.48 (1 H, s), 12.02 (1 H, s). LCMS (10 cm_esci_bicarb) Rt 2.63 min; m/z 523/525/527 [M+H].

Example 95

(E)-N'-(3,5-dibromo-4-hydroxybenzylidene)-3-(naphthalen-2-yloxy)benzohydrazide (164)

$^1$H NMR δ (ppm) (DMSO-$d_6$): 7.34-7.41 (2 H, m), 7.48-7.58 (3 H, m), 7.59-7.67 (2 H, m), 7.77 (1 H, d, J=4 Hz), 7.88-8.00 (4 H, m), 8.05 (1 H, d, J=8 Hz), 8.32 (1 H, s), 10.51 (1 H, br s), 12.01 (1 H, s). LCMS (10 cm_esci_bicarb) Rt 2.92 min; m/z 539/541/543 [M+H].

Example 96

(E)-3-(biphenyl-3-yloxy)-N'-(3,5-dibromo-4-hydroxybenzylidene)benzohydrazide (165)

$^1$H NMR δ (ppm) (DMSO-$d_6$): 7.07-7.11 (1 H, m), 7.35 (1 H, dd, J=8 and 4 Hz), 7.39-7.45 (2 H, d, m), 7.47-7.66 (6 H, m), 7.70 (2 H, d, J=4 Hz), 7.75 (1 H, d, J=8 Hz), 7.94 (2 H, s), 8.33 (1 H, s), 10.52 (1 H, br s), 12.01 (1 H, s). LCMS (10 cm_esci_bicarb) Rt 3.07 min; m/z 565/567/569 [M+H].

Example 97

(E)-2-(5-chlorothiophen-2-yl)-N'-(3,5-dibromo-4-hydroxybenzylidene)quinoline-4-carbohydrazide (166)

$^1$H NMR δ (ppm) (DMSO-$d_6$): 7.27-7.37 (2 H, m), 7.66 (1 H, dt, J=24.07, 7.64 Hz), 7.77-7.90 (2 H, m), 8.01 (2 H, s), 8.04-8.09 (2 H, m), 8.13 (1 H, d, J=8.39 Hz), 8.25 (1 H, d, J=3.06 Hz), 8.37 (1 H, s), 12.35 and 12.46 (1 H, two s). LCMS (10 cm_esci_bicarb) Rt 2.93 min; m/z 564/566/568/570 [M+H].

Example 98

(E)-N'-(3,5-dibromo-4-hydroxybenzylidene)-5-(hex-1-ynyl)nicotinohydrazide (167)

$^1$H NMR δ (ppm) (DMSO-$d_6$): 0.96 (3 H, t, J=7.26 Hz), 1.43-1.65 (4 H, m), 2.51-2.57 (2 H, m), 7.97 (2 H, s), 8.22-8.35 (2 H, m), 8.76 (1 H, t, J=8.34 Hz), 8.99 (1 H, d, J=2.10

Hz), 10.46 (1 H, s), 12.14 (1 H, s). LCMS (10 cm_esci_bicarb) Rt 2.71 min; m/z 478/480/482 [M+H].

Example 99

(E)-N'-(3,5-dibromo-4-hydroxybenzylidene)-3-(3-(methoxymethyl)phenoxy)benzohydrazide (168)

$^1$H NMR δ (ppm) (DMSO-d$_6$): 3.29 (3 H, s), 4.45 (2 H, s), 7.01-7.04 (2 H, m), 7.17 (1 H, d, J=8 Hz), 7.27 (1 H, d, J=8 Hz), 7.41-7.47 (1 H, m), 7.56-7.62 (2 H, m), 7.73 (1 H, d, J=4 Hz), 7.94 (2 H, s), 8.32 (1 H, s), 10.51 (1 H, br s), 12.01 (1 H, s). LCMS (10 cm_esci_bicarb) Rt 2.67 min; m/z 533/535/537 [M+H].

Example 100

(E)-4-tert-butyl-N'-(3,5-dibromo-4-hydroxybenzylidene)benzohydrazide (169)

$^1$H NMR δ (ppm) (DMSO-d$_6$): 1.36 (9 H, s), 7.58 (2 H, d, J=8.15 Hz), 7.88 (2 H, d, J=8.08 Hz), 7.94 (2 H, s), 8.33 (1 H, s), 10.46 (1 H, s), 11.90 (1 H, s). LCMS (10 cm_esci_bicarb) Rt 2.74 min; m/z 453/455/457 [M+H].

Example 101

(E)-N'-(3,5-dibromo-4-hydroxybenzylidene)-3-(4-isopropoxyphenoxy)benzohydrazide (170)

$^1$H NMR δ (ppm) (DMSO-d$_6$): 1.30 (6 H, d, J=4 Hz), 4.61 (1 H, m), 7.00 (2 H, d, J=12 Hz), 7.05 (2 H, d, J=12 Hz), 7.16-7.19 (1 H, m), 7.49 (1 H, s), 7.53 (1 H, t, J=8 Hz), 7.65 (1H, d, J=8 Hz), 7.93 (2 H, s), 8.32 (1 H, s), 10.52 (1 H, br s), 11.98 (1 H, s). LCMS (10 cm_esci_bicarb) Rt 2.95 min; m/z 547/549/551 [M+H].

Example 102

(E)-3-(4-chlorophenylsulfonyl)-N'-(3,5-dibromo-4-hydroxybenzylidene)thiazolidine-2-carbohydrazide (171)

$^1$H NMR δ (ppm) (DMSO-d$_6$): 2.69 (1 H, ddd, J=10.59, 8.11, 6.62 Hz), 3.03 (1 H, ddd, J=10.62, 6.46, 3.99 Hz), 3.66-3.75 (2 H, m), 3.88 (1 H, t, J=6.27 Hz), 4.09-4.17 (1 H, m), 5.50 and 6.13 (1 H, two s), 7.73-7.82 (2 H, m), 7.85-7.98 (2 H, m), 7.98 (2 H, s), 8.13 (1 H, s), 10.49 (1 H, br s), 11.67 and 11.72 (1 H, two s). LCMS (10 cm_esci_bicarb) Rt 2.63 min; m/z 582/584/586/588 [M+H].

Example 103

(E)-3-tert-butyl-N'-(3,5-dibromo-4-hydroxybenzylidene)-1-(4-fluorobenzyl)-1H-pyrazole-5-carbohydrazide (172)

$^1$H NMR δ (ppm) (DMSO-d$_6$): 1.32 (9 H, s), 5.70 (2 H, s), 6.96 (1 H, s), 7.12-7.27 (5 H, m), 7.92 (2 H, s), 8.25 (1 H, s), 10.49 (1 H, br s), 11.90 (1 H, s). LCMS (10 cm_esci_bicarb) Rt 3.09 min; m/z 551/553/555 [M+H].

Example 104

(E)-N'-(3,5-dibromo-4-hydroxybenzylidene)-2-(2,2-dimethyl-2,3-dihydrobenzofuran-7-yloxy)acetohydrazide (173)

$^1$H NMR δ (ppm) (DMSO-d$_6$): 1.46 (6 H, d, J=4.04 Hz), 3.04 (2 H, d, J=4.17 Hz), 4.65 and 5.15 (2 H, two s), 6.71-6.89 (3 H, m), 7.88-7.91 (3 H, m), 10.43 (1 H, s), 11.58 and 11.67 (1 H, two s). LCMS (10 cm_esci_bicarb) Rt 2.69 min; m/z 497/499/501 [M+H].

Example 105

(E)-N'-(3,5-dibromo-4-hydroxybenzylidene)-2,5-bis(2,2,2-trifluoroethoxy)benzohydrazide (174)

$^1$H NMR δ (ppm) (DMSO-d$_6$): 4.75-4.86 (4 H, m), 7.18-7.32 (3 H, m), 7.58 and 7.95 (2H, two s), 7.93 and 8.13 (1H two s), 10.46 (1 H, s), 11.70 and 11.88 (1 H, two s). LCMS (10 cm_esci_bicarb) Rt 2.77 min; m/z 593/595/597 [M+H].

Example 106

(E)-N'-(3,5-dibromo-4-hydroxybenzylidene)-2-phenoxybenzohydrazide (175)

$^1$H NMR δ (ppm) (DMSO-d$_6$): 6.97 (2 H, t, J=7.8 Hz), 7.08 (2 H, t, J=7.9 Hz), 7.18 (1 H, t, J=7.3 Hz), 7.23-7.34 (1 H, m), 7.40-7.58 (3 H, m), 7.60-7.71 (1 H, m), 7.85-7.95 (1 H, m), 8.19 (1 H, s), 10.35-10.55 (1 H, s, br), 11.84 (1 H, s). LCMS (10 cm_esci_bicarb) Rt 2.72 min; m/z 489/491/493 [M+H].

Example 107

(E)-N'-(3,5-dibromo-4-hydroxybenzylidene)-2-(7-methyl-2,3-dihydro-1H-inden-4-yloxy)acetohydrazide (176)

$^1$H NMR δ (ppm) (DMSO-d$_6$): 1.99-2.10 (2 H, m), 2.17 (3 H, s), 2.78-2.96 (4 H, m), 4.63 and 5.12 (2 H, two s), 6.59 (1 H, dd, J=21.4, 8.1 Hz), 6.90 (1 H, dd, J=13.8, 8.1 Hz), 7.89 and 8.18 (1 H, two s), s), 7.90 (2H, s), 10.39 and 10.47 (1 H, two s), 11.58 (1 H, s). LCMS (10 cm_esci_bicarb) Rt 2.8 min; m/z 481/483/485 [M+H].

Example 108

(E)-4-(4-chlorophenyl)-N'-(3,5-dibromo-4-hydroxybenzylidene)cyclohexanecarbohydrazide (177)

$^1$H NMR δ (ppm) (DMSO-d$_6$): 1.47 (2 H, q, J=12.65 Hz), 1.54-1.70 (2 H, m), 1.91 (4H, t, J=11.43 Hz), 2.31 (1 H, t, J=11.88 Hz), 2.60 (1 H, d, J=11.31 Hz), 7.27-7.40 (4 H, m), 7.85 and 7.89 (2 H, two s), 8.09 (1 H, s), 10.39 (1 H, s), 11.20 and 11.46 (1 H, two s). LCMS (10 cm_esci_bicarb) Rt 2.91 min; m/z 513/515/517/519 [M+H].

Example 109

(E)-3,4-dichloro-N-(3-(2-(3,5-dibromo-4-hydroxybenzylidene)hydrazinecarbonyl)phenyl)benzenesulfonamide (178)

$^1$H NMR δ (ppm) (DMSO-d$_6$): 7.35 (1 H, d, J=7.9 Hz), 7.47 (1 H, t, J=7.8 Hz), 7.63-7.69 (2 H, m), 7.74 (1 H, dd, J=8.5, 2.2 Hz), 7.90 (1 H, d, J=8.5 Hz), 7.94 (2 H, s), 7.99 (1 H, d, J=2.1 Hz), 8.31 (1 H, s), 10.49 (1 H, s), 10.70 (1 H, s), 11.96 (1 H, s). LCMS (10 cm_apci_formic) Rt 3.72 min; m/z 620/622/624/626/628 [M+H].

Example 110

(E)-N'-(3,5-dibromo-4-hydroxybenzylidene)-2-(2,3-dichlorophenoxy)acetohydrazide (180)

$^1$H NMR δ (ppm) (DMSO-d$_6$): 1.46 (6 H, d, J=4.04 Hz), 3.04 (2 H, d, J=4.17 Hz), 4.65 and 5.15 (2 H, two s), 6.71-6.89

(3 H, m), 7.88-7.91 (3 H, m), 10.43 (1 H, s), 11.58 and 11.67 (1 H, two s). LCMS (10 cm_esci_bicarb) Rt 2.8 min; m/z 495/497/499/501 [M+H].

Example 111

(E)-2-(4-chlorophenylamino)-N'-(4-hydroxy-3-(trifluoromethoxy)benzylidene)acetohydrazide (181)

$^1$H NMR δ (ppm) (DMSO-d$_6$): 4.24 and 3.82 (2 H, two d), 5.99 and 6.23 (1 H, two br s), 6.60-6.68 (2 H, m), 7.09-7.17 (3 H, m), 7.54-7.65 (2H, m), 7.96 and 8.19 (1 H, two s), 9.93 (1 H, br s), 11.47 and 11.48 (1 H, two s). LCMS (10 cm_apci_formic) Rt 3.31 min; m/z 388/390 [M+H].

Example 112

(E)-4-bromo-2-chloro-N'-(3,5-dibromo-4-hydroxybenzylidene)benzohydrazide (182)

$^1$H NMR δ (ppm) (DMSO-d$_6$): 12.14 and 12.06 (1 H, two s), 8.16 (0.5 H, s), 7.96-7.87 (2.5 H, m), 7.71 (1 H, td, J=8.20, 1.88 Hz), 7.59-7.54 (1.5 H m), 7.46 (0.5 H, d, J=8.19 Hz). LCMS (10 cm_esci_bicarb) Rt 2.57 min; m/z 509/511/513/515/517 [M+H].

Example 113

(E)-N'-(3,5-dibromo-4-hydroxybenzylidene)-4-(trifluoromethoxy)benzohydrazide (183)

$^1$H NMR δ (ppm) (DMSO-d$_6$): 7.57 (2 H, d, J=8.28 Hz), 7.96 (2 H, s), 8.07 (2 H, d, J=8.38 Hz), 8.33 (1 H, s), 10.50 (1 H, s), 12.06 (1 H, s). LCMS (10 cm_esci_bicarb) Rt 2.56 min; m/z 481/483/485 [M+H].

Example 114

(E)-2-(4-chlorophenylamino)-N'-(3,4-dihydroxybenzylidene)acetohydrazide (184)

$^1$H NMR δ (ppm) (DMSO-d$_6$): 3.80 and 4.22 (2 H, two d), 5.97 and 6.20 (1 H, two br s), 6.57-6.64 (2 H, m), 6.68-6.94 (2 H, m), 7.54-7.13 (3H, m), 7.87 and 8.07 (1 H, two s), 9.32 (2H, br s), 11.24 (1 H, s). LCMS (10 cm_apci_formic) Rt 2.78 min; m/z 320/322 [M+H].

Example 115

(E)-N'-(3,5-dibromo-4-hydroxybenzylidene)-2-(naphthalen-1-yloxy)acetohydrazide (185)

$^1$H NMR δ (ppm) (DMSO-d$_6$): 4.90 and 5.41 (2 H, two s), 6.95 (1 H, t, J=8.92 Hz), 7.42-7.62 (4 H, m), 7.88-7.98 (3 H, m), 7.96 and 8.23 (1 H, two s), 8.26-8.35 (1 H, m), 10.45 (1H, s), 11.71 and 11.78 (1 H, two s). LCMS (10 cm_esci_bicarb) Rt 2.71 min; m/z 477/479/481 [M+H].

Example 116

(E)-N'-(3,4-dihydroxybenzylidene)-3-(4-fluorobenzyloxy)thiophene-2-carbohydrazide (186)

$^1$H NMR δ (ppm) (DMSO-d$_6$): 5.41 (2 H, s), 7.23 (1 H, d, J=5.54 Hz), 7.29 (2 H, t, J=8.70 Hz), 7.63 (2 H, d, J=6.68 Hz), 7.82-7.88 (1 H, m), 7.89 (2 H, s), 8.13 (1 H, s), 10.40 (1 H, s), 10.75 (1 H, s). LCMS (10 cm_esci_bicarb) Rt 2.66 min; m/z 527/529/531 [M+H].

Example 117

(E)-N'-(3,5-dibromo-4-hydroxybenzylidene)-2-naphthohydrazide (187)

$^1$H NMR δ (ppm) (DMSO-d$_6$): 7.63-7.72 (2 H, m), 7.95-8.16 (6 H, m), 8.39 (1 H, s), 8.57 (1 H, s), 10.49 (1 H, s), 12.15 (1 H, s). LCMS (10 cm_esci_bicarb) Rt 2.56 min; m/z 447/449/451 [M+H]

Example 118

(E)-N-(3-(2-(3,4-dihydroxybenzylidene)hydrazinecarbonyl)phenyl)naphthalene-2-sulfonamide (188)

$^1$H NMR δ (ppm) (DMSO-d$_6$): 7.38 (2 H, m), 7.55 (1 H, d, J=6.4 Hz), 7.65-7.75 (3 H, m), 7.83 (1 H, dd, J=8.7, 1.9 Hz), 7.91 (2 H, s), 8.04 (1 H, d, J=8.1 Hz), 8.11-8.19 (2 H, m), 8.27 (1 H, s), 8.50 (1 H, s), 10.48 (1 H, br s), 10.66 (1 H, s), 11.90 (1 H, s). LCMS (10 cm_apci_formic) Rt 3.58 min; m/z 602/604/606 [M+H].

Example 119

(E)-N'-(3,5-dibromo-4-hydroxybenzylidene)-4-(trifluoromethyl)benzohydrazide (189)

$^1$H NMR δ (ppm) (DMSO-d$_6$): 7.90-7.99 (4 H, m), 8.14 (2 H, d, J=8.06 Hz), 8.35 (1 H, s), 10.51 (1 H, s), 12.16 (1 H, s). LCMS (10 cm_esci_bicarb) Rt 2.59 min; m/z 465/467/469 [M+H].

Example 120

(E)-3-bromo-N'-(3,5-dibromo-4-hydroxybenzylidene)benzohydrazide (190)

$^1$H NMR δ (ppm) (DMSO-d$_6$): 7.54 (1 H, t, J=7.90 Hz), 7.84 (1 H, d, J=8.10 Hz), 7.89-8.00 (3 H, m), 8.12 (1 H, s), 8.33 (1 H, s), 10.51 (1 H, s), 12.05 (1 H, s). LCMS (10 cm_esci_bicarb) Rt 2.51 min; m/z 475/477/479/481/483 [M+H].

Example 121

(E)-N'-(3,5-dibromo-4-hydroxybenzylidene)-3-(4-(pyrrolidine-1-carbonyl)phenoxy)benzohydrazide (191)

$^1$H NMR δ (ppm) (DMSO-d$_6$): 1.89-1.98 (4 H, m), 3.50-3.56 (4 H, m), 7.16 (2 H, d, J=8 Hz), 7.40 (1 H, d, J=8 Hz), 7.64-7.71 (4 H, m), 7.84 (1 H, d, J=8 Hz), 7.99 (2 H, s), 8.38 (1H, s), 12.03 (1 H, s). LCMS (10 cm_esci_bicarb) Rt 2.39 min; m/z 586/588/590 [M+H].

Example 122

(E)-N'-(3,5-dibromo-4-hydroxybenzylidene)-1H-indole-2-carbohydrazide (192)

$^1$H NMR δ (ppm) (DMSO-d$_6$): 7.11 (1H, t), 7.26 (1H, t), 7.36 (1H, s), 7.50 (1H, d), 7.71 (1H, d), 7.37 (2H, s), 8.33 (1H,

Example 123

(E)-3-chloro-N'-(3,5-dibromo-4-hydroxybenzylidene)benzohydrazide (193)

¹H NMR δ (ppm) (DMSO-d₆): 7.61 (1 H, t, J=7.87 Hz), 7.71 (1 H, d, J=8.26 Hz), 7.87-8.00 (4 H, m), 8.33 (1 H, s), 10.50 (1 H, s), 12.06 (1 H, s). LCMS (10 cm_esci_bicarb) Rt 2.47 min; m/z 431/433/435/437 [M+H].

Example 124

(E)-N'-(3,5-dibromo-4-hydroxybenzylidene)-2-(4-ethylphenoxy)acetohydrazide (194)

¹H NMR δ (ppm) (DMSO-d₆): 1.18 (3 H, t, J=7.57 Hz), 2.54-2.61 (2 H, m), 5.13 and 4.65 (2 H, two s), 6.86 (1 H, d, J=8.36 Hz), 6.93 (1 H, d, J=8.34 Hz), 7.16 (2 H, dd, J=14.81, 8.29 Hz), 7.91 (2 H, s), 8.22 and 7.93 (1 H, two s), 10.43 (1 H, s), 11.65 and 11.60 (1 H, two s). LCMS (10 cm_esci_bicarb) Rt 2.63 min; m/z 455/457/459 [M+H].

Example 125

(E)-3-chloro-N'-(3,5-dibromo-4-hydroxybenzylidene)-6-methylbenzo[b]thiophene-2-carbohydrazide (195)

¹H NMR δ (ppm) (378.2 K, DMSO-d₆): 2.54 (3 H, s), 7.46 (1 H, d), 7.86 (1 H, d), 7.90 (2 H, s), 8.27 (1 H, s), 11.64 (1 H, s). LCMS (10 cm_esci_bicarb) Rt 2.78 min; m/z 501/503/505/507 [M+H].

Example 126

(E)-ethyl 1-(2-(2,6-dibromo-4-((2-(3-phenoxybenzoyl)hydrazono)methyl)phenoxy)acetyl)piperidine-4-carboxylate (196)

¹H NMR δ (ppm) (DMSO-d₆): 1.23 (3 H, t, J=7.09 Hz), 1.35-1.91 (4 H, m), 2.61-3.40 (5 H, m), 3.29 (1 H, s), 3.91-4.31 (4 H, m), 4.75 (2 H, s), 7.12 (2 H, d, J=7.97 Hz), 7.24 (1 H, s), 7.28 (1 H, d, J=8.64 Hz), 7.48 (2 H, t, J=7.65 Hz), 7.60 (2 H, d, J=8.97 Hz), 7.74 (1 H, d, J=7.58 Hz), 8.06 (2 H, s), 8.39 (1 H, s), 12.13 (1 H, s). LCMS (10 cm_esci_bicarb) Rt 3.95 min; m/z 686/688/690 [M+H].

Example 127

(E)-N'-(3,5-dibromo-4-hydroxybenzylidene)-2-(4-(trifluoromethoxy)phenoxy)acetohydrazide (197)

¹H NMR δ (ppm) (DMSO-d₆): 4.71 and 5.21 (2 H, two s), 7.01-7.09 (2 H, m), 7.28-7.35 (2 H, m), 7.88-7.90 (2 H, m), 7.91 and 8.17 (1 H, two s), 10.43 (1 H, s), 11.60 and 11.70 (1 H, s). LCMS (10 cm_esci_bicarb) Rt 2.7 min; m/z 511/513/515 [M+H].

Example 128

(E)-N'-(3,5-dibromo-4-hydroxybenzylidene)-5-methyl-1-(4-methylphenyl)-1H-pyrazole-4-carbohydrazide (198)

¹H NMR δ (ppm) (DMSO-d₆): 2.43 (3 H, s), 2.54 (3 H, s), 7.36-7.49 (5 H, m), 7.93 (2 H, s), 8.12 and 8.24 (1 H, two s), 10.41 (1 H, br s), 11.63 (1 H, s). LCMS (10 cm_esci_bicarb) Rt 2.65 min; m/z 491/493/495 [M+H].

Example 129

(E)-N'-(3,5-dibromo-4-hydroxybenzylidene)-4-methyl-2-phenylpyrimidin-5-carbohydrazide (199)

¹H NMR δ (ppm) (DMSO-d₆): 2.52-2.55 (3 H, m), 7.56-7.61 (4 H, m), 7.99 and 8.03 (1H, two s), 8.22 (1 H, s), 8.46-8.50 (2 H, m), 8.99 and 8.90 (1 H, two s), 10.51 (1 H, s), 12.17 and 12.23 (1 H, two s). LCMS (10 cm_esci_bicarb) Rt 2.55 min; m/z 489/491/493 [M+H].

Example 130

(E)-N'-(3,5-dibromo-4-hydroxybenzylidene)-3-(trifluoromethyl)benzohydrazide (200)

¹H NMR δ (ppm) (DMSO-d₆): 7.83 (1 H, t, J=7.77 Hz), 7.95-8.05 (3 H, m), 8.26 (2 H, d, J=10.47 Hz), 8.35 (1 H, s), 12.16 (1 H, s). LCMS (10 cm_esci_bicarb) Rt 2.57 min; m/z 465/467/469 [M+H].

Example 131

(E)-2-(3-chlorophenylamino)-N'-(3,5-dibromo-4-hydroxybenzylidene)acetohydrazide (201)

¹H NMR δ (ppm) (DMSO-d₆): 3.85 and 4.28 (2 H, two d, J=5.60 Hz), 6.16 and 6.37 (1H, two s), 6.53-6.64 (2 H, m), 6.69 (1 H, s), 7.12 (1 H, q, J=7.95 Hz), 7.91 (2 H, d, J=5.30 Hz), 7.95 and 8.13 (1 H, two s), 10.5 (1 H, br s), 11.54 and 11.58 (1 H, two s). LCMS (10 cm_esci_bicarb) Rt 2.5 min; m/z 460/462/4645/466 [M+H].

Example 132

(E)-N-(3-(2-(3,5-dibromo-4-hydroxybenzylidene)hydrazinecarbonyl)phenyl)benzenesulfonamide (202)

¹H NMR δ (ppm) (DMSO-d₆): 7.33 (1 H, d, J=8.2 Hz), 7.41 (1 H, t, J=7.8 Hz), 7.54-7.67 (5 H, m), 7.82 (2 H, d, J=7.6 Hz), 7.92 (2 H, s), 8.29 (1 H, s), 10.51 (1 H, br s), 10.57 (1 H, s), 11.93 (1 H, s). LCMS (10 cm_apci_formic) Rt 3.32 min; m/z 552/554/556 [M+H].

Example 133

(E)-2-(4-chlorophenylamino)-N'-(4-hydroxy-3-(trifluoromethyl)benzylidene)acetohydrazide (203)

¹H NMR δ (ppm) (DMSO-d₆): 4.24 and 3.82 (2 H, two d), 6.22 and 5.99 (1 H, two t, Hz), 6.69-6.61 (2 H, m), 7.16-7.10 (3 H, m), 7.91-7.80 (2 H, m), 8.22 and 8.00 (1 H, two s), 10.43 (1 H, br s), 11.47 and 11.49 (1 H, two s). LCMS (10 cm_apci_formic) Rt 3.3 min; m/z 372/374 [M+H].

Example 134

(E)-N'-(3,5-dibromo-4-hydroxybenzylidene)-4-(2,5-dimethyl-1H-pyrrol-1-yl)benzohydrazide (204)

¹H NMR δ (ppm) (DMSO-d₆): 2.04 (6 H, s), 5.88 (2 H, s), 7.47 (2 H, d, J=8.7 Hz), 7.97 (2 H, s), 8.06 (2 H, d, J=8.09 Hz), 8.35 (1 H, s), 10.46 (1H, s, br), 12.09 (1 H, t, J=14.96 Hz). LCMS (10 cm_esci_bicarb) Rt 2.75 min; m/z 490/492/494 [M+H].

Example 135

(E)-2-(2,6-dibromo-4-((2-(3-phenoxybenzoyl)hydrazono)methyl)phenoxy)acetic acid (205)

$^1$H NMR δ (ppm) (DMSO-d$_6$): 4.61 (2 H, s), 7.12 (2 H, d, J=8.03 Hz), 7.21-7.31 (2 H, m), 7.48 (2 H, t, J=7.68 Hz), 7.59 (2 H, t, J=7.69 Hz), 7.74 (1 H, d, J=7.66 Hz), 8.05 (2 H, s), 8.39 (1 H, s), 12.13 (1 H, s), 13.40 (1 H, br s). LCMS (10 cm_esci_bicarb) Rt 2.64 min; m/z 547/549/551 [M+H].

Example 136

(E)-tert-butyl 1-(2-(3,5-dibromo-4-hydroxybenzylidene)hydrazinyl)-1-oxo-3-phenylpropan-2-ylcarbamate (206)

$^1$H NMR δ (ppm) (DMSO-d$_6$): 1.35 (9 H, s), 2.74-2.92 (1 H, m), 2.93-3.01 (2 H, m), 4.25 and 5.01 (1 H, two td, J=9.30, 3.68 Hz), 7.15-7.27 (1 H, m), 7.29-7.38 (4 H, m), 7.92 (1 H, d, J=4.89 Hz), 7.89 and 8.09 (1 H, two s), 10.39 (1 H, br s), 11.43 and 11.64 (1 H, two s). LCMS (10 cm_esci_bicarb) Rt 2.65 min; m/z 540/542/544 [M+H].

Example 137

(E)-N'-(3,5-dibromo-4-hydroxybenzylidene)-1-phenyl-5-(trifluoromethyl)-1H-pyrazole-4-carbohydrazide (207)

$^1$H NMR δ (ppm) (DMSO-d$_6$): 7.56-7.67 (5 H, m), 7.81 and 7.97 (2 H, two s), 8.07 and 8.30 (1 H, two s) 8.23 (1 H, s), 10.48 (1 H, s), 12.12 (1 H, s). LCMS (10 cm_esci_bicarb) Rt 2.55 min; m/z 531/533/535 [M+H].

Example 138

(E)-1-(4-chlorophenyl)-N'-(3,5-dibromo-4-hydroxybenzylidene)-5-propyl-1H-pyrazole-4-carbohydrazide (208)

$^1$H NMR δ (ppm) (DMSO-d$_6$): 0.79 (3 H, t, J=7.34 Hz), 1.41-1.54 (2 H, m), 2.98 (2 H, t, J=7.53 Hz), 7.59 (2 H, d, J=8.30 Hz), 7.68 (2 H, d, J=8.55 Hz), 7.93 (2 H, s), 8.27 (2 H, s), 10.43 (1 H, br s), 11.68 (1 H, s). LCMS (10 cm_esci_bicarb) Rt 2.8 min; m/z 539/541/543/545 [M+H].

Example 139

(E)-2-(7-chloroquinoline-4-ylthio)-N'-(3,5-dibromo-4-hydroxybenzylidene)acetohydrazide (209)

$^1$H NMR δ (ppm) (DMSO-d$_6$): 3.96, 4.15 and 4.59 (2 H, three s), 7.51-7.59 (1 H, m), 7.69-7.75 (1 H, m), 7.88-7.99 (2 H, m), 8.06-8.19 (2 H, m), 8.75-8.82 (1 H, m), 11.76 and 11.92 (1 H, two s). LCMS (10 cm_esci_bicarb) Rt 2.56 min; m/z 528/530/532/534 [M+H].

Example 140

(E)-N'-(3,5-dibromo-4-hydroxybenzylidene)-3-(4-(hydroxymethyl)phenoxy)benzohydrazide (210)

$^1$H NMR δ (ppm) (DMSO-d$_6$): 4.53 (2 H, d, J=4 Hz), 5.23 (1 H, m), 7.08 (2 H, d, J=8 Hz), 7.21-7.25 (1 H, m), 7.41 (2 H, d, J=8 Hz), 7.53-7.60 (2 H, m), 7.67-7.71 (1 H, m), 7.92 (2H, s), 8.32 (1 H, s), 11.95 (1 H, br s). LCMS (10 cm_apci_formic) Rt 3.3 min; m/z 519/521/523 [M+H].

Example 141

(E)-N'-(3,5-dibromo-4-hydroxybenzylidene)-5-((4,5-dichloro-1H-imidazol-1-yl)methyl)furan-2-carbohydrazide (211)

$^1$H NMR δ (ppm) (DMSO-d$_6$): 5.43 (2 H, s), 6.67 (1 H, s), 7.33 (1 H, s), 7.92 (2 H, s), 7.99 (1 H, s), 8.29 (1 H, s), 10.48 (1 H, br s), 11.87 (1 H, s). LCMS (10 cm_esci_bicarb) Rt 2.4 min; m/z 535/537/539/541 [M+H].

Example 142

(E)-4-chloro-N'-(3,5-dibromo-4-hydroxybenzylidene)benzohydrazide (212)

$^1$H NMR δ (ppm) (DMSO-d$_6$): 7.65 (2 H, d, J=8.26 Hz), 7.96 (4 H, d, J=9.42 Hz), 8.32 (1 H, s), 10.51 (1 H, s), 12.05 (1 H, s). LCMS (10 cm_esci_bicarb) Rt 2.47 min; m/z 431/433/435/437 [M+H].

Example 143

(E)-2-(6-bromonaphthalen-2-yloxy)-N'-(4-hydroxy-3,5-di(thiophen-3-yl)benzylidene)acetohydrazide (213)

$^1$H NMR δ (ppm) (DMSO-d$_6$): 4.82 and 5.33 (2H, two s), 7.50-7.55 (2H, m), 7.64-7.87 (11H, m), 8.07-8.16 (2H, m), 9.01 (1H, s), 11.65 (1H, s). LCMS (10 cm_apci_formic) Rt 4.45 min; m/z 563/565 [M+H].

Example 144

(E)-3-chloro-N'-(3,5-dibromo-4-hydroxybenzylidene)-4-methylthiophene-2-carbohydrazide (217)

$^1$H NMR δ (ppm) (DMSO-d$_6$): 2.24 (3 H, s), 7.70 (1 H, br m), 7.92 (2 H, s), 8.27 (1 H, br m), 10.49 (1 H, s), 11.82 (1 H, br m). LCMS (10 cm_esci_bicarb) Rt 2.47 min; m/z 451/453/455/457 [M+H].

Example 145

(E)-N'-(3,5-dibromo-4-hydroxybenzylidene)-3,5-bis(trifluoromethyl)benzohydrazide (219)

$^1$H NMR δ (ppm) (DMSO-d$_6$): 7.75 and 7.99 (2 H, two s), 8.03-8.58 (4 H, s), 10.54 (1H, s), 12.26 and 12.32 (1 H, two s). LCMS (10 cm_esci_bicarb) Rt 2.94 min; m/z 533/535/537 [M+H].

Example 146

(E)-2-(4-chlorophenylamino)-N'-(3,4,5-trifluorobenzylidene)acetohydrazide (228)

$^1$H NMR δ (ppm) (DMSO-d$_6$): 3.85 and 4.28 (2H, two s), 6.01 and 6.29 (1H, two m), 6.61-6.71 (2H, m), 7.12-7.16 (2H, m), 7.63-7.80 (2H, m), 7.98 and 8.24 (1H, two s), 11.75 (1H, s). LCMS (10 cm_apci_formic) Rt 3.75 min; m/z 342/344 [M+H].

Example 147

(E)-N'-(3,5-dibromo-4-hydroxybenzylidene)-4-methyl-2-phenylthiazole-5-carbohydrazide (238)

$^1$H NMR δ (ppm) (DMSO-d$_6$): 2.71 and 2.81 (3 H, two s), 7.57-7.60 (3 H, m), 7.94-8.28 (5 H, m), 10.51 (1 H, s), 11.98 (1 H, s). LCMS (10 cm_esci_bicarb) Rt 2.59 min; m/z 494/496/498 [M+H].

Example 148

(E)-N'-(3,5-dibromo-4-hydroxybenzylidene)-4-phenyl-1,2,3-thiadiazole-5-carbohydrazide (240)

$^1$H NMR δ (ppm) (DMSO-$d_6$): 12.52 and 12.47 (1 H, two s), 8.11 and 8.04 (1 H, two s), 7.98-7.89 (1 H, m), 7.81 (3 H, d, J=5.09 Hz), 7.62-7.49 (4 H, m). LCMS (10 cm_apci_formic) Rt 3.62 min; m/z 481/483/485 [M+H].

Example 149

(E)-N'-(3,5-dibromo-4-hydroxybenzylidene)-2-phenylthiazole-4-carbohydrazide (245)

$^1$H NMR δ (ppm) (DMSO-$d_6$): 7.56-7.63 (3 H, m), 7.93 (2 H, s), 8.13-8.16 (2 H, m), 8.52 (1 H, s), 8.54 (1 H, s), 10.48 (1 H, s), 11.89 (1 H, s). LCMS (10 cm_esci_bicarb) Rt 2.68 min; m/z 480/482/484 [M+H].

Example 150

(E)-2-(2-chlorophenoxy)-N'-(3,5-dibromo-4-hydroxybenzylidene)acetohydrazide (251)

$^1$H NMR δ (ppm) (DMSO-$d_6$): 4.80 and 5.33 (2 H, two s), 6.96-7.11 (2 H, m), 7.27-7.34 (1 H, m), 7.45-7.50 (1 H, m), 7.91-8.16 (3 H, m), 10.43 (1 H, br s), 11.69 and 11.71 (1 H, two s). LCMS (10 cm_esci_bicarb) Rt 2.5 min; m/z 461/463/465/467 [M+H].

Example 151

(E)-N'-(3,5-dibromo-4-hydroxybenzylidene)-2-(2,3-dichlorophenyl)thiazole-4-carbohydrazide (256)

$^1$H NMR δ (ppm) (DMSO-$d_6$): 7.63 (1 H, t, J=7.99 Hz), 7.87-7.94 (3 H, m), 8.45 (1 H, dd, J=7.96, 1.57 Hz), 8.51 (1 H, s), 8.74 (1 H, s), 10.52 (1 H, s), 11.98 (1 H, s). LCMS (10 cm_esci_bicarb) Rt 2.94 min; m/z 548/550/552/554 [M+H].

Example 152

(E)-2-(4-chloro-2-methylphenoxy)-N'-(3,5-dibromo-4-hydroxybenzylidene)acetohydrazide (291)

$^1$H NMR δ (ppm) (DMSO-$d_6$): 2.24 and 2.27 (3 H, two s), 4.71 and 5.23 (2 H, two s), 6.90 (1 H, m), 7.13-7.28 (2 H, m), 7.88-8.17 (3 H, m), 10.42 (1 H, s), 11.64 (1 H, s). LCMS (10 cm_esci_bicarb) Rt 2.71 min; m/z 475/477/479/481 [M+H].

Example 153

(E)-N'-((1H-indol-6-yl)methylene)-2-(4-chlorophenylamino)acetohydrazide (294)

$^1$H NMR δ (ppm) (DMSO-$d_6$): 3.83 and 4.28 (2H, two d), 6.02 and 6.26 (1H, two t), 6.51 (1H, s), 6.66-6.70 (2H, m), 7.15 (2H, t), 7.40-7.49 (2H, m), 7.62 (1H, t), 7.72 (1H, d), 8.13 and 8.33 (1H, two s), 11.31-11.41 (2H, m). LCMS (10 cm_apci_formic) Rt 3.35 min; m/z 327/329 [M+H].

Example 154

(E)-N'-(3,5-dibromo-4-hydroxybenzylidene)biphenyl-4-carbohydrazide (299)

$^1$H NMR δ (ppm) (DMSO-$d_6$): 7.41-7.46 (1 H, m), 7.50-7.54 (2 H, m), 7.78-8.03 (8 H, m), 8.33 (1 H, s), 10.47 (1 H, br s), 12.0 (1 H, s). LCMS (10 cm_esci_bicarb) Rt 2.67 min; m/z 473/475/477 [M+H].

Example 155

(E)-N'-(3,5-dibromo-4-hydroxybenzylidene)-2-phenylacetohydrazide (301)

$^1$H NMR δ (ppm) (DMSO-$d_6$): 3.57 and 4.00 (2H, two s), 7.23-7.38 (5H, m), 7.89-8.10 (3H, m), 10.42 (1H, br s), 11.43 and 11.71 (1H, two s). LCMS (10 cm_apci_formic) Rt 3.24 min; m/z 411/413/415 [M+H].

Example 156

(E)-2-(4-(1,3-dithiolan-2-yl)phenoxy)-N'-(3,5-dibromo-4-hydroxybenzylidene)acetohydrazide (312)

$^1$H NMR δ (ppm) (DMSO-$d_6$): 3.32-3.40 (2 H, m) 3.49-3.59 (2 H, m), 4.69 and 5.19 (2H, two s), 5.74 and 5.75 (1 H, two s), 6.90 and 6.96 (2 H, two d, J=8.5 Hz), 7.46 and 7.49 (2 H, two d, J=8.5 Hz), 7.90-8.21 (3 H, m), 10.41 (1 H, br s), 11.63 and 11.67 (1 H, two s). LCMS (10 cm_esci_bicarb) Rt 2.67 min; m/z 531/533/535 [M+H].

Example 157

(E)-N'-(3,5-dibromo-4-hydroxybenzylidene)benzo[b]thiophene-2-carbohydrazide (317)

$^1$H NMR δ (ppm) (DMSO-$d_6$): 7.48-7.57 (2 H, m), 7.98 (1 H, s), 8.04-8.12 (3 H, m), 8.28-8.45 (2 H, m), 10.52 (1 H, br s), 12.11 and 12.27 (1 H, two s). LCMS (10 cm_esci_bicarb) Rt 2.66 min; m/z 453/455/457 [M+H].

Example 158

(E)-2-(2-chlorophenylamino)-N'-(3,5-dibromo-4-hydroxybenzylidene)acetohydrazide (329)

$^1$H NMR δ (ppm) (DMSO-$d_6$): 4.37 and 3.96 (2 H, d, J=4.79 Hz), 5.74 and 5.57 (1 H, two s), 7.27-6.50 (4 H, m), 7.99-7.86 (3 H, m), 10.42 (1 H, br s), 11.65 and 11.64 (1 H, two s). LCMS (10 cm_esci_bicarb) Rt 2.54 min; m/z 460/462/464/466 [M+H].

Example 159

(E)-N'-(3-bromo-4-fluorobenzylidene)-2-(4-chlorophenylamino)acetohydrazide (343)

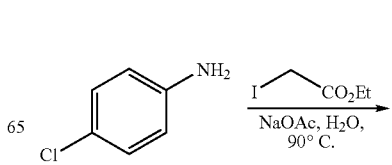

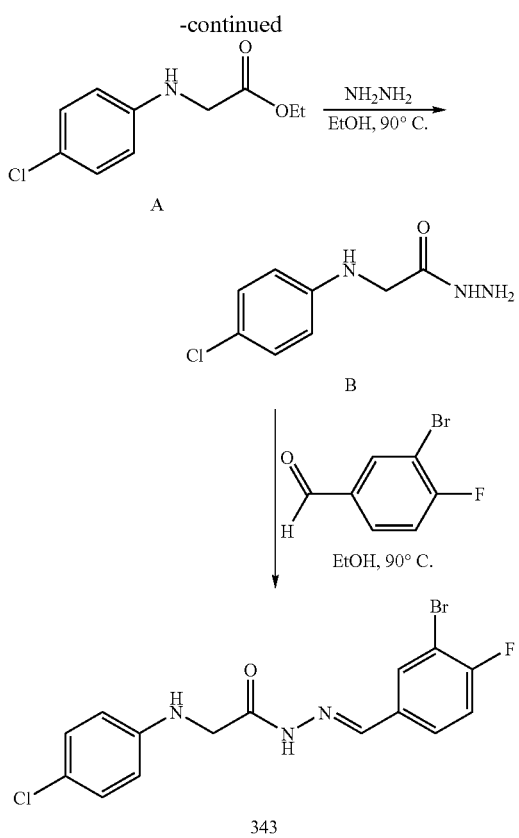

Ethyl 2-(4-chlorophenylamino)acetate (A)

4-Chloroaniline (15.5 g, 122 mmol), ethyl iodoacetate (14.4 mL, 122 mmol) and sodium acetate (20.0 g, 244 mmol) were stirred in water (24 mL) at 90° C. for 3 hours. After cooling to room temperature the precipitate was collected by filtration, washing with water (40 mL), to yield the title compound (25.6 g, 98%) as brown prisms. $^1$H NMR (400 MHz, CDCl$_3$) δ 1.29 (3H, t), 3.86 (2H, s), 4.22 (2H, q), 6.53 (2H, d), 7.14 (2H, d).

2-(4-Chlorophenylamino)acetohydrazide (B)

Ethyl 2-(4-chlorophenylamino)acetate (A) (25.6 g, 120 mmol) and hydrazine monohydrate (7.0 mL, 144 mmol) were heated to reflux in ethanol (120 mL) for 22 hours. After concentration in vacuo, the solid obtained was recrystallised from ethanol to yield the title compound (14.0 g, 59%) as a pale brown powder. $^1$H NMR (400 MHz, CDCl$_3$) δ 3.85 (2H, d), 4.18 (2H, br), 6.53 (2H, d), 7.16 (2H, d), 7.60 (1H, br).

(E)-N'-(3-bromo-4-fluorobenzylidene)-2-(4-chlorophenylamino)acetohydrazide (343)

2-(4-Chlorophenylamino)acetohydrazide (B) (101 mg, 0.51 mmol) and 3-bromo-4-fluorobenzaldehyde (104 mg, 0.51 mmol) were refluxed in ethanol (3 mL) for 15 hours. After cooling to room temperature the precipitate was collected by filtration, washed with ethanol (20 mL) and water (20 mL). Drying in vacuo yielded the title compound (129 mg, 66%) as a colorless powder. $^1$H NMR δ (ppm) (DMSO-d$_6$): 3.84 and 4.28 (2 H, two d), 6.01 and 6.25 (1 H, two br s), 6.62-6.69 (2 H, m), 7.12-7.17 (2H, m), 7.47-7.51 (1 H, m), 7.77-7.83 (1 H, m), 8.01 and 8.25 (1 H, two s), 8.05-8.12 (1H, m), 11.63 (1 H, two s). LCMS (10 cm_apci_formic) Rt 3.85 min; m/z 384/386/388 [M+H].

Example 160

(E)-N'-(3,5-dibromo-4-hydroxybenzylidene)-4H-thieno[3,2-c]chromene-2-carbohydrazide (344)

$^1$H NMR δ (ppm) (DMSO-d$_6$): 5.29 and 5.36 (2 H, two s), 6.95-7.11 (2 H, m), 7.22-7.31 (1 H, m), 7.40-7.57 (1 H, m), 7.80-8.30 (4 H, m), 12.01 and 12.06 (1 H, two s). LCMS (10 cm_esci_bicarb) Rt 2.71 min; m/z 507/509/511 [M+H].

Example 161

(E)-2-(4-chlorophenylamino)-N'-(4-fluoro-3-methylbenzylidene)acetohydrazide (362)

$^1$H NMR δ (ppm) (DMSO-d$_6$): 2.32 (3H, s), 3.84 and 4.27 (2H, two s), 6.02 and 6.26 (1H, two s), 6.67 (2H, m), 7.17 (2H, m), 7.25 (1H, m), 7.61 (2H, m), 8.00 and 8.23 (1H, two s), 11.48 and 11.56 (1H, two s). LCMS (10 cm_apci_formic) Rt 3.73 min; m/z 320/322 [M+H].

Example 162

(E)-2-(4-chlorophenylamino)-N'-(4-fluorobenzylidene)acetohydrazide (366)

$^1$H NMR δ (ppm) (DMSO-d$_6$): 3.83 and 4.26 (2 H, two d), 6.00 and 6.26 (1 H, two br s), 6.62-6.69 (2 H, m), 7.12-7.17 (2 H, m), 7.30-7.34 (2H, m), 7.76-7.85 (2 H, m), 8.04 and 8.28 (1H, two s), 11.49 and 11.53 (1 H, two s). LCMS (10 cm_apci_formic) Rt 3.53 min; m/z 306/308 [M+H].

Example 163

(E)-N'-(3,5-dibromo-4-hydroxybenzylidene)-5-methyl-4-phenyloxazole-2-carbohydrazide (393)

$^1$H NMR δ (ppm) (DMSO-d$_6$): 2.69 (3 H, s), 7.43 (1 H, t), 7.55 (2 H, t), 7.80 (2 H, d), 7.93 (2 H, s), 8.48 (1 H, s), 10.55 (1 H, s), 12.42 (1 H, s). LCMS (10 cm_esci_bicarb) Rt 2.63 min; m/z 478/480/482 [M+H].

Example 164

(E)-2-(4-chlorophenylsulfonyl)-N'-(3,5-dibromo-4-hydroxybenzylidene)acetohydrazide (430)

$^1$H NMR δ (ppm) (DMSO-d$_6$): 4.48 and 4.94 (2H, two s), 7.62-8.06 (7H, m), 10.47 (1H, br s), 11.75 and 11.84 (1H, two s). LCMS (10 cm_apci_formic) Rt 3.17 min; m/z 509/511/513/515 [M+H].

Example 165

(E)-N'-(3,5-dibromo-4-hydroxybenzylidene)-2-(3-phenoxyphenylamino)acetohydrazide (431)

$^1$H NMR δ (ppm) (DMSO-d$_6$): 3.81 and 4.24 (2H, two d), 6.00-6.45 (4H, m), 7.02 (2H, 2), 7.08-7.14 (2H, m), 7.36-7.40 (2H, m), 7.88-8.11 (3H, m), 10.42 (1H, s), 11.55 (1 H, s). LCMS (10 cm_apci_formic) Rt 3.82 min; m/z 518/520/522 [M+H].

Example 166

(3-bromo-4-chlorophenyl)(3-(3,5-dibromo-4-hydroxyphenyl)-4,5-dihydro-1H-pyrazol-1-yl)methanone (58)

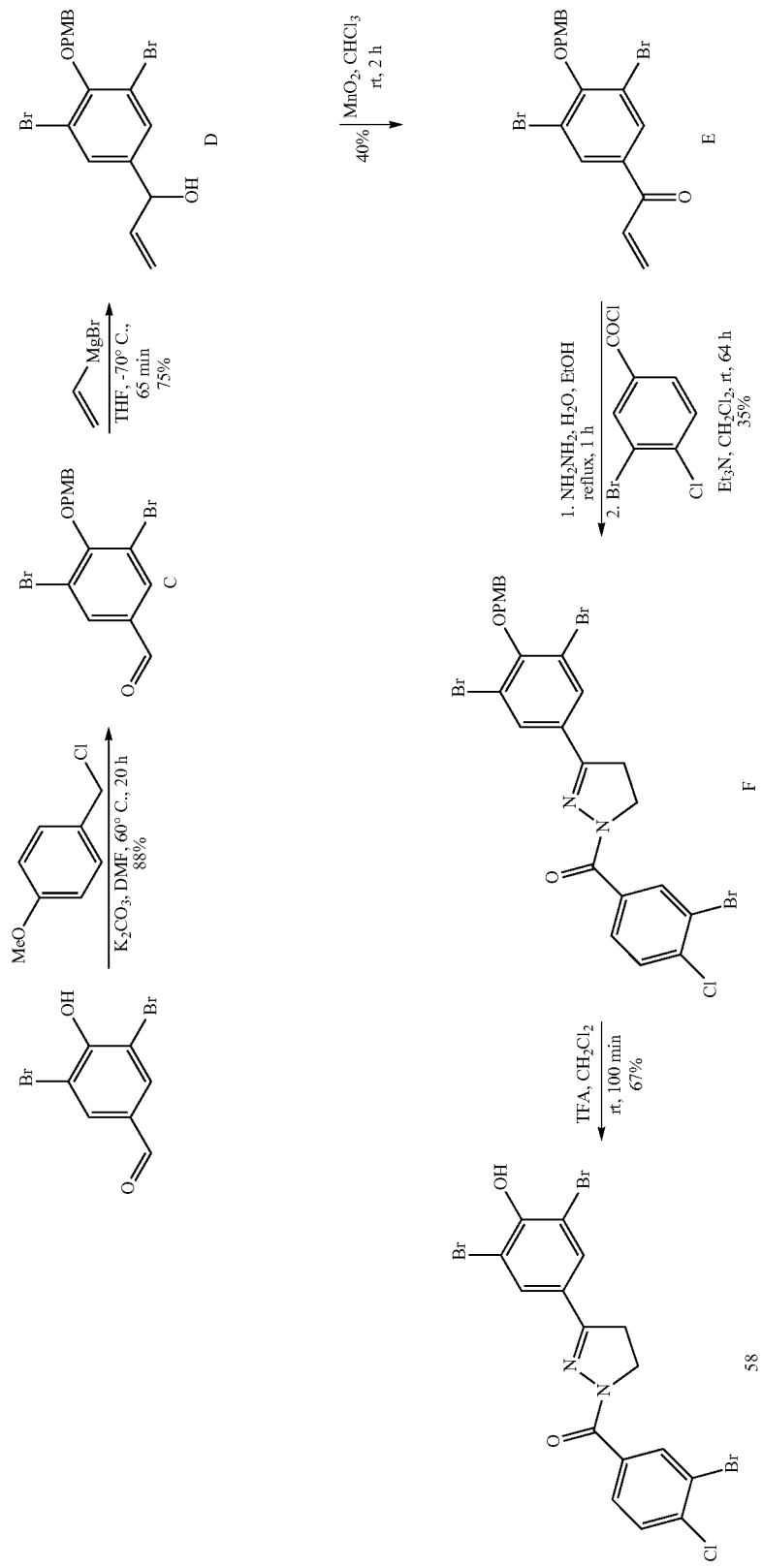

3,5-Dibromo-4-(4-methoxybenzyloxy)benzaldehyde (C)

To a stirred solution of 3,5-dibromo-4-hydroxybenzaldehyde (5.30 g, 18.9 mmol) in anhydrous DMF (15 mL) under nitrogen was added potassium carbonate (5.50 g, 19.9 mmol) and the mixture was stirred for 10-15 min during which time vigorous effervescence was observed. 4-methoxybenzyl chloride (2.70 mL, 19.9 mL) was then added and the mixture was heated at 60° C. for 20 h. The mixture was filtered and the filtrate was evaporated. The residual oil was then poured into water (100 mL) and the mixture was stirred for 1-2 h. The resulting solid was collected by filtration, washed with water and dried under vacuum at 60° C. to leave 6.63 g (88%) of the title compound as a pale brown solid. $^1$H NMR (DMSO-$d_6$) 3.82 (3 H, s), 5.06 (2 H, s), 7.02 (2 H, d), 7.53 (2 H, d), 8.24 (2 H, s), 9.95 (1 H, s).

1-(3,5-Dibromo-4-(4-methoxybenzyloxy)phenyl)prop-2-en-1-ol (D)

To a stirred solution of 3,5-dibromo-4-(4-methoxybenzyloxy)benzaldehyde (C) (3.04 g, 7.60 mmol) in anhydrous THF (40 mL) under nitrogen, cooled to −76° C., was added dropwise over 15 min vinylmagnesium bromide (1.0 M solution in THF, 11.4 mL, 11.4 mmol), keeping the internal temperature below −70° C. The mixture was stirred at <−70° C. for 65 min, and then quenched with saturated aqueous ammonium chloride solution (6 mL). The stirred mixture was allowed to warm to room temperature, and then partitioned between ethyl acetate (200 mL) and water (200 mL). The organic layer was washed with saturated aqueous sodium chloride (80 mL), dried ($Na_2SO_4$) and evaporated. The residue was purified by flash chromatography (silica gel, 15% EtOAc/pet. ether) to give 2.45 g (75%) of the title compound as a colourless oil. $^1$H NMR δ (ppm) (CDCl$_3$): 1.96 (1 H, d, J=3.75 Hz), 3.83 (3 H, s), 4.96 (2 H, s), 5.14 (1 H, t, J=4.58 Hz), 5.27 (1 H, d, J=10.29 Hz), 5.35-5.42 (1 H, m), 5.98 (1 H, ddd, J=17.08, 10.28, 6.28 Hz), 6.90-6.96 (2 H, m), 7.50-7.57 (4 H, m).

1-(3,5-Dibromo-4-(4-methoxybenzyloxy)phenyl)prop-2-en-1-one (E)

To a stirred solution of 1-(3,5-dibromo-4-(4-methoxybenzyloxy)phenyl)prop-2-en-1-ol (D) (2.45 g, 5.73 mmol) in chloroform (35 mL) under nitrogen was added manganese (IV) oxide (6.47 g, 74.4 mmol) and the mixture was stirred vigorously for 2 h. The mixture was filtered through glass fibre paper and the solid was washed with more chloroform (5×15 mL). The combined filtrates were evaporated and the residue was purified by flash chromatography (silica gel, 15% EtOAc/pet. ether) to afford 0.9804 g (40%) of the title compound as a white solid. $^1$H NMR δ (ppm) (CDCl$_3$): 3.84 (3 H, s), 5.04 (2 H, s), 5.99 (1 H, dd, J=10.56, 1.51 Hz), 6.47 (1 H, dd, J=17.06, 1.52 Hz), 6.91-6.97 (2 H, m), 7.07 (1 H, dd, J=17.06, 10.57 Hz), 7.52 (2 H, d, J=8.41 Hz), 8.12 (2 H, s).

(3-Bromo-4-chlorophenyl)(3-(3,5-dibromo-4-(4-methoxybenzyloxy)phenyl)-4,5-dihydro-1H-pyrazol-1-yl)methanone (F)

To a stirred mixture of 1-(3,5-dibromo-4-(4-methoxybenzyloxy)phenyl)prop-2-en-1-one (E) (0.1003 g, 0.235 mmol) in ethanol (2 mL) was added hydrazine monohydrate (19.4 μL, 0.400 mmol) and the mixture was heated at 85° C. for 1 h. After cooling, the mixture was partitioned between dichloromethane (15 mL) and water (10 mL). The aqueous layer was extracted further with dichloromethane (15 mL) and the combined organic extracts were washed with brine (10 mL), dried ($Na_2SO_4$), and nitrogen was bubbled through the solution for a few minutes. The solution was concentrated to 10 mL in vacuo with no heat and then added by syringe to a stirred mixture of 3-bromo-4-chlorobenzoyl chloride (59.8 mg, 0.236 mmol) in dichloromethane (1 mL) under nitrogen. Triethylamine (34.4 μL, 0.247 mmol) was then added dropwise and the resulting solution was stirred at room temperature for 64 h. The mixture was diluted with dichloromethane (10 mL) and successively washed with water (10 mL), 10% aqueous citric acid (10 mL), 1 N aqueous NaOH (10 mL), water (10 mL) and brine (10 mL). The remaining organic layer was dried ($Na_2SO_4$) and evaporated. The residue was purified by flash chromatography (silica gel, 40% EtOAc/pet. ether) to give 54.1 mg (35%) of the title compound as a yellow solid. $^1$H NMR δ (ppm) (CDCl$_3$): 3.23 (2 H, t, J=10.04 Hz), 3.83 (3 H, s), 4.26 (2 H, t, J=10.05 Hz), 5.02 (2 H, s), 6.93 (2 H, d, J=8.32 Hz), 7.51 (2 H, d, J=8.18 Hz), 7.55 (1 H, d, J=8.38 Hz), 7.83 (2 H, s), 7.86 (1 H, dd, J=8.43, 2.07 Hz), 8.28 (1 H, d, J=2.02 Hz).

(3-Bromo-4-chlorophenyl)(3-(3,5-dibromo-4-hydroxyphenyl)-4,5-dihydro-1H-pyrazol-1-yl)methanone (58)

To a stirred solution of (3-bromo-4-chlorophenyl)(3-(3,5-dibromo-4-(4-methoxybenzyloxy)phenyl)-4,5-dihydro-1H-pyrazol-1-yl)methanone (F) (51.8 mg, 0.0788 mmol) in anhydrous dichloromethane (5 ml) under nitrogen was added trifluoroacetic acid (0.1 mL) and the solution was stirred at room temperature for 1 h 40 min. The solvent was evaporated and more dichloromethane was added to the residue and evaporated. The residue was then recrystallised from EtOAc-$CH_2Cl_2$ and the resulting solid was collected by filtration, washed with 50% EtOAc/pet. ether and dried at 55° C. under vacuum to leave 28.2 mg (67%) of the title compound as a light-brown solid. $^1$H NMR δ (ppm) (DMSO-$d_6$): 4.13 (2 H, t, J=9.8 Hz), 7.81 (1 H, d, J=8.4 Hz), 7.86 (2 H, s), 7.86-7.93 (1 H, m), 8.24 (1 H, d, J=2.0 Hz), 10.62 (1 H, br s). LCMS (10 cm_apci_formic) Rt 4.29 min; m/z 535/537/539/541/543 [M+H].

Example 167

6-(3,5-dibromo-4-hydroxyphenyl)-2-(3-hydroxybenzyl)-4,5-dihydropyridazin-3(2H)-one (72)

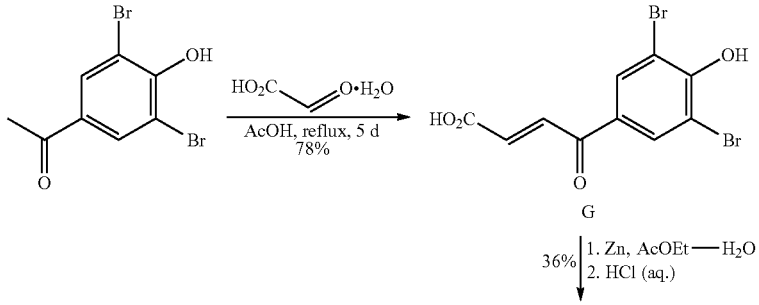

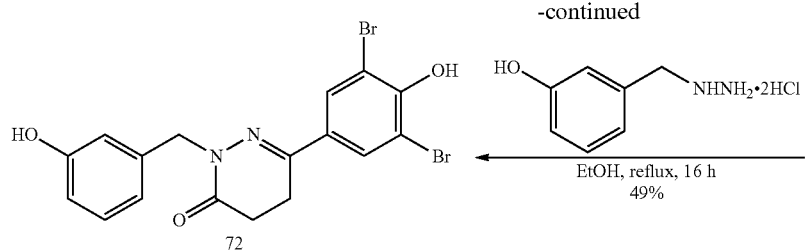 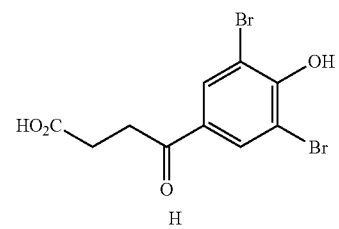

(E)-4-(3,5-Dibromo-4-hydroxyphenyl)-4-oxobut-2-enoic acid (G)

A mixture of 1-(3,5-dibromo-4-hydroxyphenyl)ethanone (5.0 g, 17.01 mmol) and glyoxylic acid monohydrate (1.566 g, 17.01 mmol) in acetic acid (10 mL) was stirred and heated at reflux for 5 days. After this time, the precipitate formed was collected and recrystallised from toluene. This gave the title compound as a brown solid (4.674 g, 78%). $^1$H NMR δ (ppm) (DMSO-$d_6$): 6.70 (1 H, d, J=15.45 Hz), 7.93 (1 H, d, J=15.46 Hz), 8.24 (2 H, s).

4-(3,5-Dibromo-4-hydroxyphenyl)-4-oxobutanoic acid (H)

To a stirred solution of (E)-4-(3,5-Dibromo-4-hydroxyphenyl)-4-oxobut-2-enoic acid (G) (2.852 g, 8.149 mmol) in ethyl acetate (27 mL) and water (3 mL) was added zinc power (5.7 g) portion wise until no further gas evolution was observed. At this point, the reaction mixture was diluted with diethyl ether (50 mL) and HCl (2 M solution, 8 mL) and the resulting mixture was filtered through a pad of Celite. After filtration, the organic solution was washed with HCl (2 M solution, 10 mL), followed by water (3×10 mL). The organic layer was then dried (MgSO$_4$) and concentrated in vacuo to give a brown solid. This was then triturated with cold ethanol to give the title compound as a pale brown solid (1.025 g, 36%). $^1$H NMR δ (ppm) (DMSO-$d_6$): 2.58 (2 H, t, J=6.12 Hz), 3.17-3.27 (2 H, m), 8.15 (2 H, s), 10.99 (1 H, s), 12.19 (1H, s)

6-(3,5-Dibromo-4-hydroxyphenyl)-2-(3-hydroxybenzyl)-4,5-dihydropyridazin-3(2H)-one (72)

A stirred mixture of 4-(3,5-dibromo-4-hydroxyphenyl)-4-oxobutanoic acid (H) (150 mg, 0.426 mmol) and 3-hydroxybenzylhydrazine dihydrochloride (135 mg, 0.639 mmol) in ethanol was heated to reflux. After heating for 16 h, the reaction mixture was cooled down and the precipitate formed was collected and dried in vacuo. This gave the title compound as a red solid (95 mg, 49%) $^1$H NMR δ (ppm) (DMSO-$d_6$): 2.59 (2 H, t), 3.01 (2 H, t, J=8.2 Hz), 4.88 (2H, s), 6.67 (1 H, d, J=8.2 Hz), 6.69-6.76 (2 H, m), 7.14 (1 H, t, J=7.8 Hz), 7.92 (2 H, s), 9.39 (1 H, s), 10.44 (1 H, s). LCMS (10 cm_apci_formic) Rt 3.33 min; m/z 453/455/457 [M+H].

Example 168

(E)-2-benzyl-3-(3,5-dibromo-4-hydroxybenzylidene-amino)quinazolin-4(3H)-one (126)

$^1$H NMR δ (ppm) (DMSO-$d_6$): 4.29 (2 H, s), 7.20-7.30 (5 H, m), 7.57-7.62 (1 H, m), 7.77 (1 H, d, J=8.2 Hz), 7.90 (1 H, ddd, J=8.2, 7.1, 1.6 Hz), 8.05 (2 H, s), 8.20 (1 H, dd, J=8.0, 1.5 Hz), 8.72 (1 H, s), 10.94 (1 H, br s). LCMS (10 cm_esci_bicarb) Rt 2.74 min; m/z 512/514/516 [M+H].

Example 169

(E)-3-(3,5-dibromo-4-hydroxybenzylidene amino)-2-isopropylquinazolin-4(3H)-one (179)

$^1$H NMR δ (ppm) (DMSO-$d_6$): 1.29 (3 H, d, J=4 Hz), 1.31 (3H, d, J=4 Hz), 3.43 (1 H, m), 7.57 (1 H, t, J=8 Hz), 7.73 (1 H, d, J=8 Hz), 7.87 (1 H, t, J=8 Hz), 8.18 (2 H, s), 8.19 (1 H, d, J=8 Hz), 8.88 (1 H, s), 11.0 (1 H, br s). LCMS (10 cm_esci_bicarb) Rt 2.82 min; m/z 464/466/468 [M+H].

Formulation Examples

Formulation Preparation 1

Hard gelatin capsules containing the following ingredients are prepared:

| Ingredients | Quantity (mg/capsule) |
| --- | --- |
| Active ingredient | 30.0 |
| Starch | 305.0 |
| Magnesium Stearate | 5.0 |

The above ingredients are mixed and filled into hard gelatin capsules in 340 mg quantities.

Formulation Preparation 2

A tablet formula is prepared using the ingredients below:

| Ingredients | Quantity (mg/tablet) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Biological Assays

Example 1

T84 Assay

Human colonic T84 cells are acquired from the European Collection of Cell Cultures (ECACC) and are grown in standard culture conditions as described by the supplier. On the day before assay 25,000 T84 cells per well are plated into standard black walled, clear bottom 384-well assay plates in standard growth medium consisting of DMEM:F12 with 10% FBS and incubated overnight. On the day of the assay the plates are washed using a standard assay buffer (HBSS with 10 mM Hepes) and incubated for 15 minutes in serum free cell culture medium before the addition of a commercially available membrane potential sensitive fluorescent dye (FLIPR Red membrane potential dye, Molecular Devices Corporation). T84 cells are incubated with the FLIPR Red membrane potential dye for 45 minutes in the presence and absence of test compound before being transferred to a commercially available fluorescence imaging plate reader (FLIPR384, Molecular Devices Corporation). Fluorescence levels are monitored continuously every second for 150 seconds; after an initial 10 second baseline, CFTR channel activity is stimulated through the addition of 10 μM Forskolin in the presence of 100 μM of the phosphodiesterase inhibitor iso-butyl-methylxanthine (IBMX). Addition of the forskolin leads to the activation of intracellular adenylyl cylase 1, elevating cAMP levels and results in the phosphorylation and opening of CFTR anion channels. CFTR channel opening causes chloride ion efflux and subsequent depolarization of the cells, which is measured by an increase in fluorescence. CFTR inhibitor compounds prevent cell depolarization and the associated increase in fluorescence.

Example 2

FRT Assay

Fisher Rat Thyroid (FRT) cells stably co-expressing wild-type human CFTR and a reporter protein such as green fluorescent protein (GFP) or a mutant such as the yellow fluorescent protein-based $Cl^{31}/I^-$ halide sensor e.g. YFP-H148Q can be cultured on 96-well plates as described in Gruenert (2004), supra or Ma et al. (2002) J. Clin. Invest. 110:1651-1658. Following a 48 hour incubation confluent FRT-CFTR-YFP-H148Q cells in 96-well plates are washed three times with phosphate buffered saline (PBS) and then CFTR halide conductance is activated by incubation for 5 minutes with a cocktail containing 5 μM, forskolin, 25 μM apigenin and 100 μM, isobutylmethyl-xanthine (IBMX). Test compounds at a final concentration of 10 μM and 20 μM are added five minutes prior to assay of iodide influx in which cells are exposed to a 100 mM inwardly-directed iodide gradient. Baseline YFP fluorescence is recorded for two seconds followed by 12 seconds of continuous recording of fluorescence after rapid addition of the $I^-$ containing solution to create a $I^-$ gradient. Initial rates of $I^-$ influx can be computed from the time course of decreasing fluorescence after the $I^-$ gradient as known to those skilled in the art and described in Yang et al. (2002) J. Biol. Chem.: 35079-35085.

Activity of the CFTR channel can also be measured directly using electrophysiological methods. An example protocol of for measuring CFTR current is described as whole cell patch clamp method. As an illustration, recordings are conducted at room temperature (~21° C.) using a HEKA EPC-10 amplifier. Electrodes are fabricated from 1.7 mm capillary glass with resistances between 2 and 3 MΩ using a Sutter P-97 puller. For recording the CFTR channels, the extracellular solution can contain (in mM) 150 NaCl, 1 $CaCl_2$, 1 $MgCl_2$, 10 glucose, 10 mannitol, and 10 TES (pH 7.4), and the intracellular (pipette) solution can contain 120 CsCl, $MgCl_2$, 10 TEA-Cl, 0.5 EGTA, 1 Mg-ATP and 10 HEPES (pH 7.3).

The CFTR channels are activated by forskoin (5 μM) in the extracellular solution. The cells are held at a potential of 0 mV and currents were recording by a voltage ramp protocol from −120 mV to +80 mV over 500 ms every 10 seconds. No leak subtraction was employed. Compounds are superfused to individual cells using a Biologic MEV-9/EVH-9 rapid perfusion system.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A compound represented by formula II:

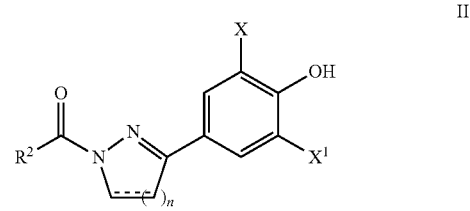

wherein:
$R^2$ is substituted aryl, substituted with 1 or 2 halo groups;
X and $X^1$ are independently halo;
═══ is a single or double bond; and
n is 1;
or a pharmaceutically acceptable salt thereof.

2. A compound represented by formula III:

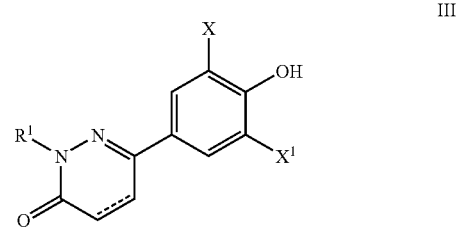

wherein:
$R^1$ is substituted alkyl, substituted with an aryl group that is optionally substituted with a hydroxy group;
X and $X^1$ are independently halo; and
═══ is a single or double bond;
or a pharmaceutically acceptable salt thereof.

3. A compound which is:
6-(3,5-dibromo-4-hydroxyphenyl)-2-(3-hydroxybenzyl)-4,5-dihydropyridazin-3(2H)-one or
(3-bromo-4-chlorophenyl)(3-(3,5-dibromo-4-hydroxyphenyl)-4,5-dihydro-1 H-pyrazol-1-yl)methanone, or
a pharmaceutically acceptable salt thereof.

4. A pharmaceutical composition comprising a therapeutically effective amount of a compound as defined in any one of claims 1, 2, and 3 and a pharmaceutically acceptable carrier.

5. A method for treating diarrhea in an animal in need thereof comprising administering to the animal an effective amount of the composition of claim 4, thereby treating diarrhea.

* * * * *